United States Patent
Bikker et al.

(10) Patent No.: US 6,528,535 B2
(45) Date of Patent: Mar. 4, 2003

(54) BICYCLIC INHIBITORS OF PROTEIN FARNESYL TRANSFERASE

(75) Inventors: Jack Bikker, Ann Arbor, MI (US); Ellen Myra Dobrusin, Ann Arbor, MI (US); Annette Marian Doherty, Paris (FR); Matthew Drowns, Waltham, MA (US); James Stanley Kaltenbronn, Ann Arbor, MI (US); Juergen Kleinschroth, Denzlingen (DE); Dennis Joseph McNamara, Ann Arbor, MI (US); John Quin, III, Ann Arbor, MI (US); Joseph Thomas Repine, Ann Arbor, MI (US); Marcin Stasiak, Kirkland, WA (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/910,967

(22) Filed: Jul. 23, 2001

(65) Prior Publication Data
US 2002/0006936 A1 Jan. 17, 2002

Related U.S. Application Data

(62) Division of application No. 09/500,606, filed on Apr. 28, 2000, now Pat. No. 6,265,422, which is a division of application No. 09/355,662, filed as application No. PCT/US98/03025 on Feb. 11, 1998, now Pat. No. 6,133,303.
(60) Provisional application No. 60/037,504, filed on Feb. 11, 1997.

(51) Int. Cl.[7] .................... A61K 31/415; A61K 31/425; C07D 233/30; C07D 233/68; C07D 277/04
(52) U.S. Cl. ....................... 514/398; 514/399; 514/402; 514/365; 514/424; 548/323.5; 548/342.5; 548/186; 548/225; 548/522
(58) Field of Search ............................ 548/323.5, 342.5, 548/186, 225, 522; 514/398, 399, 402, 365, 424

(56) References Cited

U.S. PATENT DOCUMENTS

| | | | |
|---|---|---|---|
| 3,660,385 A | 5/1972 | Albrecht et al. | 269/240 A |
| 3,671,520 A | 6/1972 | Albrecht et al. | 260/240 |
| 4,610,099 A | 9/1986 | Foguet et al. | 514/399 |
| 5,059,609 A | 10/1991 | Eggle et al. | 514/314 |
| 5,149,703 A | 9/1992 | Lau et al. | 514/311 |
| 5,434,177 A | 7/1995 | Riekkinen et al. | |
| 5,977,134 A | 11/1999 | Ciccarone et al. | |
| 6,127,390 A | 10/2000 | DeSolms et al. | |
| 6,127,396 A | 10/2000 | Cordi et al. | |
| 6,143,766 A | 11/2000 | Kaltenbronn et al. | |
| RE37,303 E * | 7/2001 | Schwartz et al. | |
| 6,403,581 B1 * | 6/2002 | Ayral-Kaloustian et al. | |
| 6,410,539 B1 * | 6/2002 | Arnould | |

FOREIGN PATENT DOCUMENTS

| | | |
|---|---|---|
| EP | 0 130 833 | 9/1985 |
| EP | 0 313 295 | 10/1988 |
| EP | 0 695 753 | 2/1996 |
| EP | 0 717 037 | 6/1996 |
| WO | 94/08996 | 4/1994 |
| WO | 95/33748 | 12/1995 |
| WO | 97/12874 | 4/1997 |
| WO | 97/17070 | 5/1997 |
| WO | 97/27854 | 8/1997 |
| WO | 97/36877 | 10/1997 |

OTHER PUBLICATIONS

Tewari, S. C., et al., *Indian J. Chem.*, "Studies in Antifertility Agents: Part XXI–I–Ethyl–2–(o–,m–& p–Hydroxybenzyl)–6–Hydroxy–3,4–Dihydronaphthalenes", 1979, vol. 17b, pp 282–285.

Rufer, C., et al., *J. Med. Chem.*, Chemotherpeutic Nitroheterocycles 18.2–(5–Nitro–2–Imidazolylmethylene)–1–Indanones,–1–Tetralones, and –acetophenones substituted by aminoalkaxy Groups, 1975, vol. 18:3, pp 253–258.

Schwender, C.F., *J. Med. Chem.*, "Derivatives of 3,4–Dihydro–1(2H)–naphthalenone as Beta–Adrenergic Blocking Agents. 3. Carbonyl–Containing Analogs of Bunolol", 1973, vol. 14:5, pp 585–588.

Albrecht, V. R., et al., *Drug Res.*, "Chemotherapeutische Nitroheterocyclen", 1971, vol. 21:1, pp. 127–131.

Brotherton, J., *Drug Res.*, "Biological Assay of Potential Trichomonacides in vitro Using a Computer Apparatus", 1978, vol. 28, pp. 1665–1672.

Chemical Abstract No. XP–002067021 "127:95240f Synethesis of 7–(imidazol–1–yl)alkyloxyflavones", 1997, vol. 127.

PCT International Search Report, PCT/US98/03025.

* cited by examiner

*Primary Examiner*—Deborah C. Lambkin
(74) *Attorney, Agent, or Firm*—Suzanne M. Harvey; Steven R. Eck

(57) ABSTRACT

The present invention provide compounds of Formula I

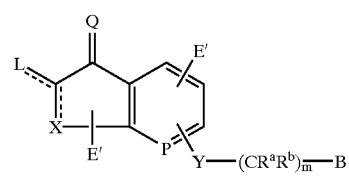

The present invention also provides a method of treating cancer and treating or preventing restenosis or atherosclerosis. Also provided by the present invention is a pharmaceutically acceptable composition containing a compound of Formula I.

18 Claims, No Drawings

BICYCLIC INHIBITORS OF PROTEIN FARNESYL TRANSFERASE

This application is a division of U.S. Ser. No. 09/560,606 filed Apr. 28, 2000, U.S. Pat. No. 6,265,422, which is a division of U.S. Ser. No. 09/355,662 filed May 2, 1999, U.S. Pat. No. 6,133,303 filed Aug. 2, 1999, which is a 371 of PCT/US98/03025 filed Feb. 11, 1998, and claims benefit of provisional application 60/037,504, filed Feb. 11, 1997.

FIELD OF THE INVENTION

The present invention relates to compounds that can be used to treat, prophylactically or otherwise, uncontrolled or abnormal proliferation of tissues. Specifically, the present invention relates to compounds that inhibit the farnesyl transferase enzyme, which has been determined to activate ras proteins that in turn activate cellular division and are implicated in cancer, restenosis, and atherosclerosis. a

BACKGROUND OF THE INVENTION

Ras protein (or p21) has been examined extensively because mutant forms are found in 20% of most types of human cancer and greater than 50% of colon and pancreatic carcinomas (Gibbs J. B., Cell, 1991;65:1, Cartwright T. et al., Chimica. Oggi., 1992;10:26). These mutant ras proteins are deficient in the capability for feedback regulation that is present in native ras, and this deficiency is associated with their oncogenic action since the ability to stimulate normal cell division cannot be controlled by the normal endogenous regulatory cofactors. The recent discovery that the transforming activity of mutant ras is critically dependent on post-translational modifications (Gibbs J. et al., Microbiol. Rev., 1989;53:171) has unveiled an important aspect of ras function and identified novel prospects for cancer therapy.

In addition to cancer, there are other conditions of uncontrolled cellular proliferation that may be related to excessive expression and/or function of native ras proteins. Post-surgical vascular restenosis and atherosclerosis are such conditions. The use of various surgical revascularization techniques such as saphenous vein bypass grafting, endarterectomy, and transluminal coronary angioplasty are often accompanied by complications due to uncontrolled growth of neointimal tissue, known as restenosis. The biochemical causes of restenosis are poorly understood and numerous growth factors and protooncogenes have been implicated (Naftilan A. J. et al., Hypertension, 1989;13:706 and J. Clin. Invest., 83:1419; Gibbons G H. et al., Hypertension, 1989;14:358; Satoh T. et al., Molec. Cell. Biol., 1993;13:3706). The fact that ras proteins are known to be involved in cell division processes makes them a candidate for intervention in many situations where cells are dividing uncontrollably. In direct analogy to the inhibition of mutant ras related cancer, blockade of ras dependent processes has the potential to reduce or eliminate the inappropriate tissue proliferation associated with restenosis or atherosclerosis, particularly in those instances where normal ras expression and/or function is exaggerated by growth stimulatory factors. See, for example, Kohl et al., Nature Med., 1995;1(8):792–748.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of post-translational processing steps that are signaled by a carboxyl terminal amino acid consensus sequence that is recognized by protein farnesyl transferase (PFT). This consensus sequence consists of a cysteine residue located four amino acids from the carboxyl terminus, followed by two lipophilic amino acids, and the C-terminal residue. The sulfhydryl group of the cysteine residue is alkylated by farnesyl pyrophosphate in a reaction that is catalyzed by protein farnesyl transferase. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicate that these post-translational modifications are essential for transforming activity. Replacement of the consensus sequence cysteine residue with other amino acids gives a ras protein that is no longer farnesylated, fails to migrate to the cell membrane and lacks the ability to stimulate cell proliferation (Hancock J. F. et al., Cell, 1989;57:1617; Schafer W R. et al., Science, 1989;245:379; Casey P. J., Proc. Natl. Acad. Sci. USA, 1989;86:8323).

Recently, protein farnesyl transferases (PFTs), also referred to as farnesyl proteintransferases (FPTs), have been identified and a specific PFT from rat brain was purified to homogeneity (Reiss Y et al., Bioch. Soc. Trans., 1992;20:487–88). The enzyme was characterized as a heterodimer composed of one alpha-subunit (49 KDa) and one beta-subunit (46 KDa), both of which are required for catalytic activity. High level expression of mammalian PFT in a baculovirus system and purification of the recombinant enzyme in active form has also been accomplished (Chen W -J. et al., J. Biol. Chem., 1993;268:9675).

In light of the foregoing, the discovery that the function of oncogenic ras proteins is critically dependent on their post-translational processing provides a means of cancer chemotherapy through inhibition of the processing enzymes. The identification and isolation of a protein farnesyl transferase that catalyzes the addition of a farnesyl group to ras proteins provides a promising target for such intervention. Ras farnesyl transferase inhibitors have been shown to have anticancer activity in several recent articles.

Ras inhibitor agents act by inhibiting farnesyl transferase, the enzyme responsible for the post-translational modification of the ras protein which helps to anchor the protein product of the ras gene to the cell membrane. The role of the ras mutation in transducing growth signals within cancer cells relies on the protein being in the cell membrane so with farnesyl transferase inhibited, the ras protein will stay in the cytosol and be unable to transmit growth signals: these facts are well-known in the literature.

A peptidomimetic inhibitor of farnesyl transferase B956 and its methyl ester B1086 at 100 mg/kg have been shown to inhibit tumor growth by EJ-1 human bladder carcinoma, HT1080 human fibrosarcoma and human colon carcinoma xenografts in nude mice (Nagasu T. et al., Cancer Res., 1995;55:5310–5314). Furthermore, inhibition of tumor growth by B956 has been shown to correlate with inhibition of ras posttranslational processing in the tumor. Other ras farnesyl transferase inhibitors have been shown to specifically prevent ras processing and membrane localization and are effective in reversing the transformed phenotype of mutant ras containing cells (Sepp-Lorenzino L. et al., Cancer Res., 1995;55:5302–5309).

In another report (Sun J. et al., Cancer Res., 1995;55:4243–4247), a ras farnesyl transferase inhibitor FTI276 has been shown to selectively block tumor growth in nude mice of a human lung carcinoma with K-ras mutation and p53 deletion. In yet another report, daily administration of a ras farnesyl transferase inhibitor L-744,832 caused tumor regression of mammary and salivary carcinomas in ras transgenic mice (Kohl et al., *Nature Med.*, 1995;1(8) :792–748). Thus, ras farnesyl transferase inhibitors have benefit in certain forms of cancer, particularly those dependent on oncogenic ras for their growth. However, it is well-known that human cancer is often manifested when several mutations in important genes occurs, one or more of which may be responsible for controlling growth and metastases. A single mutation may not be enough to sustain growth and only after two of three mutations occur, tumors can develop and grow. It is therefore difficult to determine which of these mutations may be primarily driving the growth in a particular type of cancer. Thus, ras farnesyl transferase inhibitors can have therapeutic utility in tumors not solely dependent on oncogenic forms of ras for their growth. For example, it has been shown that various ras FT-inhibitors have antiproliferative effects in vivo against tumor lines with either wild-type or mutant ras (Sepp-Lorenzino, supra.). In addition, there are several ras-related proteins that are prenylated. Proteins such as R-Ras2/TC21 are ras-related proteins that are prenylated in vivo by both farnesyl transferase and geranylgeranyl transferase I (Carboni et al., *Oncogene*, 1995;10: 1905–1913). Therefore, ras farnesyl transferase inhibitors could also block the prenylation of the above proteins and therefore would then be useful in inhibiting the growth of tumors driven by other oncogenes.

With regard to the restenosis and vascular proliferative diseases, it has been shown that inhibition of cellular ras prevents smooth muscle proliferation after vascular injury in vivo (Indolfi C. et al., *Nature Med.*, 1995;1(6):541–545). This report definitively supports a role for farnesyl transferase inhibitors in this disease, showing inhibition of accumulation and proliferation of vascular smooth muscle.

SUMMARY OF THE INVENTION

The present invention provides compounds having the Formula I

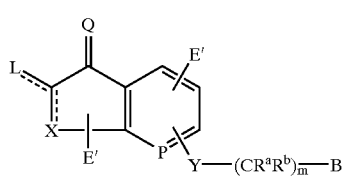

wherein Q is O, —NOR, —N—NRR, —NOCH$_2$CO$_2$R$^a$,

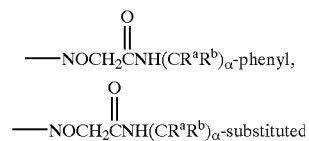

L is hydrogen,

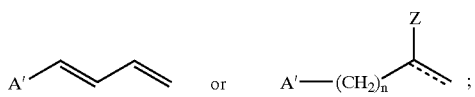

each R$^a$ or R$^b$ is independently hydrogen, C$_1$–C$_6$ alkyl, C$_2$–C$_6$ alkenyl, phenyl, or substituted phenyl, or R$^a$ and R$^b$ along with the carbon atom to which they are bonded form a C$_3$–C$_6$ cycloalkyl ring;

each R is independently hydrogen, C$_1$–C$_6$ alkyl, C$_3$–C$_6$ cycloalkyl, benzyl, C$_2$–C$_6$ alkenyl, phenyl, or substituted phenyl;

Each - - - is a bond or absent;

P is N,

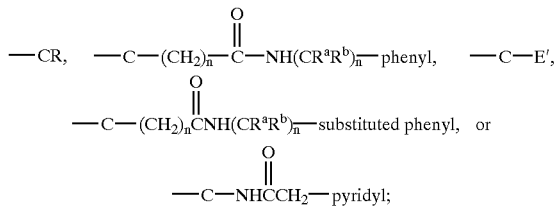

X is CH$_2$, CH$_2$O, CH$_2$S, CH$_2$SO, CH$_2$SO$_2$, CH$_2$NR, or

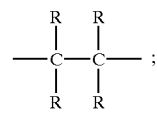

Z is hydrogen when L is

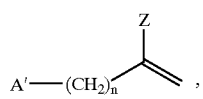

and

Z is —NRR, —R, —OR, —SR, —(CH$_2$)$_n$E, —O(CH$_2$)$_n$E, —NR(CH$_2$)$_n$E, —S(CH$_2$)$_n$E, —N$^1$-piperidinyl, —N$^1$-piperazinyl[N$^4$—R], —N-pyrrolidinyl, —N-morpholino, —N-thiomorpholino, —N-hexahydroazepine, or an amino acid having the structure

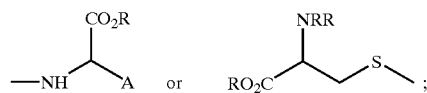

when L is

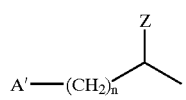

where A is a side chain of the amino acid glycine, alanine, valine, leucine, isoleucine, phenylalanine, proline, serine, threonine, tyrosine, asparagine, glutamine, lysine, arginine, tryptophan, histidine, cysteine, methionine, aspartic acid, or glutamic acid;

E is hydrogen, halogen, —CO$_2$R, —CONRR, —CN, —NO$_2$, C$_1$–C$_6$ perfluoroalkyl, C$_1$–C$_6$ perfluoroalkoxy, acetyl, —OR, —SR, —NRR, —N¹-piperidinyl, —N¹-piperazinyl[N⁴—R], —N-pyrrolidinyl, —N-morpholino, —N-thiomorpholino, —N-hexahydroazepine, aryl, heteroaryl, substituted aryl, or substituted heteroaryl;

each E' is independently hydrogen, halogen, —NO$_2$, —NRR, —R, —OR, —S(O)$_\alpha$R,

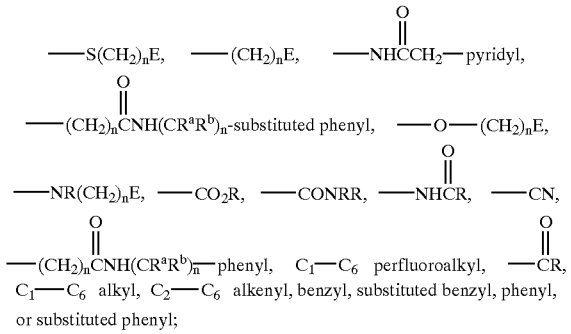

each n is independently 0 to 5 inclusive;
each $\alpha$ is independently 0, 1, or 2;
each m is independently 0, 2, 3, 4, or 5;
Y is CH$_2$, NR, O, SO, SO$_2$, or S;
A' is aryl, heteroaryl, substituted aryl, substituted heteroaryl, C$_1$–C$_6$ alkyl, C$_1$–C$_6$ substituted alkyl,

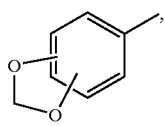

C$_3$–C$_6$ cycloalkyl or C$_3$–C$_6$ substituted cycloalkyl, provided any substituents are not —NO$_2$;

B is pyrrolyl, substituted pyrrolyl, imidazolyl, substituted imidazolyl, oxazolyl, substituted oxazolyl, thiazolyl, substituted thiazolyl,

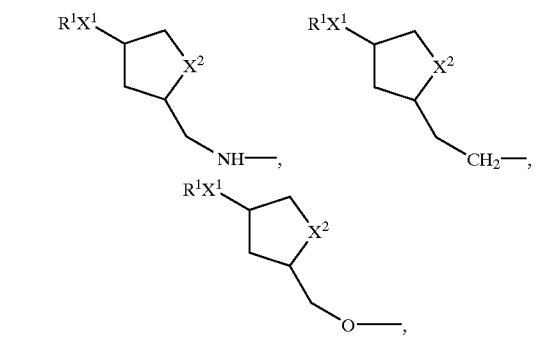

—NR$^1$—(CH$_2$)$_n$—(CHX$^3$)—(CH$_2$)$_n$—SR$^1$,
—S—(CH$_2$)$_n$—(CHX$^3$)—(CH$_2$)$_n$—SR$^1$, or
—(CH$_2$)$_n$—(CHX$^3$)—(CH$_2$)$_n$—SR$^1$;

X$^1$ is S or NR$^1$;
X$^2$ is NR$^1$ or CH$_2$;
R$^1$ is hydrogen or C$_1$–C$_6$ alkyl;
X$^3$ is hydrogen —NR$^1$R$^1$ or —C$_1$–C$_6$ alkyl, and the pharmaceutically acceptable salts, esters, amides, and prodrugs thereof, provided that the compound is not 5-(2-imidazole-1-yl-ethoxy)-indan-1-one.

In a preferred embodiment of the compounds of Formula I, Q is O.

In another preferred embodiment of the compounds of Formula I, X is —CH$_2$CH$_2$.

In another preferred embodiment of the compounds of Formula I, E' is hydrogen.

In another preferred embodiment of the compounds of Formula I, P is CH.

In another preferred embodiment of the compounds of Formula I, Y is O.

In another preferred embodiment of the compounds of Formula I, L is hydrogen.

In another preferred embodiment of the compounds of Formula I, B is imidazolyl or substituted imidazolyl.

In another preferred embodiment of the compounds of Formula I,

L is

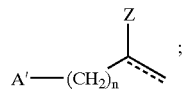

Z is hydrogen, and A' is phenyl, substituted phenyl, pyridyl, substituted pyridyl, thienyl, substituted thienyl, furyl, substituted furyl, naphthyl, or substituted naphthyl.

Also provided by the present invention are compounds having the Formula II

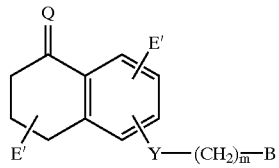

wherein Q is O, —NOR, —N—NRR, —NOCH$_2$CO$_2$R$^a$,

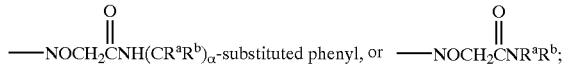

each R$^a$ or R$^b$ is independently hydrogen, C$_1$–C$_6$ alkyl, C$_2$–C$_6$ alkenyl, phenyl, or substituted phenyl, or R$^a$ and R$^b$ along with the carbon atom to which they are bonded form a C$_3$–C$_6$ cycloalkyl ring;

each R is independently hydrogen, C$_1$–C$_6$ alkyl, C$_2$–C$_6$ alkenyl, C$_1$–C$_6$ cycloalkyl, benzyl, C$_2$–C$_6$ alkenyl, phenyl, or substituted phenyl;

E is hydrogen, halogen, —CO$_2$R, —CONRR, —CN, —NO$_2$, C$_1$–C$_6$ perfluoroalkyl, C$_1$–C$_6$ perfluoroalkoxy, acetyl, —OR, —SR, —NRR, —N¹-piperidinyl, —N¹-piperazinyl[N⁴—R], —N-pyrrolidinyl, —N-morpholino, —N-thiomorpholino, —N-hexahydroazepine, aryl, heteroaryl, substituted aryl, or substituted heteroaryl; each E' is independently hydrogen, halogen, —NO$_2$, —NRR, —R, —OR, —S(O)$_\alpha$R, —S(CH$_2$)$_n$E, —(CH$_2$)$_n$E, —O—(CH$_2$)$_n$E, —NR(CH$_2$)$_n$E,

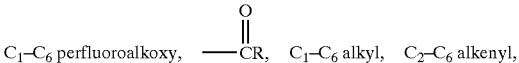

-continued

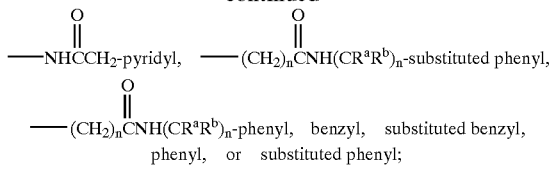
—NHCCH$_2$-pyridyl, —(CH$_2$)$_n$CNH(CR$^a$R$^b$)$_n$-substituted phenyl, —(CH$_2$)$_n$CNH(CR$^a$R$^b$)$_n$-phenyl, benzyl, substituted benzyl, phenyl, or substituted phenyl;

each n is independently 0 to 5 inclusive;
each α is independently 0, 1, or 2;
each m is independently 0, 2, 3, 4, or 5;
Y is CH$_2$, NR, O, SO, SO$_2$, or S;
B is pyrrolyl, substituted pyrrolyl, imidazolyl, substituted imidazolyl, oxazolyl, substituted oxazolyl, thiazolyl, substituted thiazolyl,

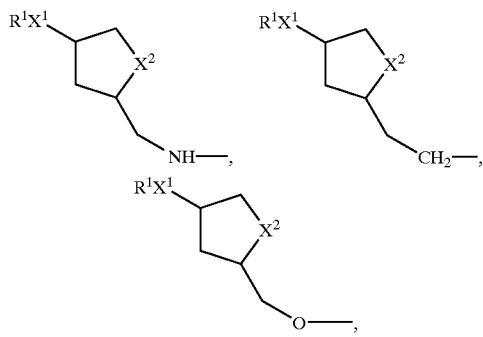

—NR$^1$—(CH$_2$)$_n$—(CHX$^3$)—(CH$_2$)$_n$—SR$^1$,
—S—(CH$_2$)$_n$—(CHX$^3$)—(CH$_2$)$_n$—SR$^1$, or
—(CH$_2$)$_n$—(CHX$^3$)—(CH$_2$)$_n$—SR$^1$;
X$^1$ is S or NR$^1$;
X$^2$ is NR$^1$ or CH$_2$;
R$^1$ is hydrogen or C$_1$–C$_6$ alkyl;
X$^3$ is hydrogen, —NR$^1$R$^1$, or —C$_1$–C$_6$ alkyl, and the pharmaceutically acceptable salts, esters, amides and prodrugs thereof In a preferred embodiment of the compounds of Formula II, Q is O.

In another preferred embodiment of the compounds of Formula II, E' is hydrogen.

In another preferred embodiment of the compounds of Formula II, Y is O.

In another preferred embodiment of the compounds of Formula II, B is imidazolyl or substituted imidazolyl.

Also provided by the present invention are compounds having the Formula III

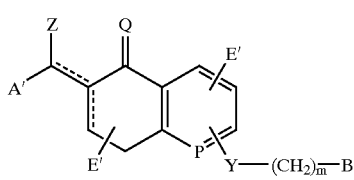

III wherein Q is O, —NOR, or —N—NRR;
Z is hydrogen when - - - is absent and Z is —NRR, —R, —OR, —SR, —(CH$_2$)$_n$E,
—O(CH$_2$)$_n$E, —NR(CH$_2$)$_n$E, —S(CH$_2$)$_n$E, —N$^1$-piperidinyl,
—N$^1$-piperazinyl[N$^4$—R], —N-pyrrolidinyl,
—N-morpholino,
—N-thiomorpholino, —N-hexahydroazepine, or an amino acid having the structure

where A is a side chain of the amino acid glycine, alanine, valine, leucine, isoleucine, phenylalanine, proline, serine, threonine, tyrosine, asparagine, glutamine, lysine, arginine, tryptophan, histidine, cysteine, methionine, aspartic acid, or glutamic acid;
when - - - is a bond;
each R$^a$ or R$^b$ is independently hydrogen, C$_1$–C$_6$ alkyl, C$_2$–C$_6$ alkenyl, phenyl, or substituted phenyl, or R$^a$ and R$^b$ along with the carbon atom to which they are bonded form a C$_3$–C$_6$ cycloalkyl ring;
each R is independently hydrogen, C$_1$–C$_6$ alkyl, C$_3$–C$_6$ cycloalkyl, benzyl, C$_2$–C$_6$ alkenyl, phenyl, or substituted phenyl;

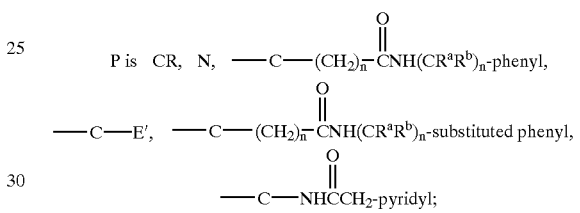

P is CR, N, —C—(CH$_2$)$_n$—CNH(CR$^a$R$^b$)$_n$-phenyl,
—C—E', —C—(CH$_2$)$_n$—CNH(CR$^a$R$^b$)$_n$-substituted phenyl, or
—C—NHCCH$_2$-pyridyl;

Each - - - is a bond or absent;
E is hydrogen, halogen, —CO$_2$R, —CONRR, —CN, —NO$_2$, C$_1$–C$_6$ perfluoroalkyl, C$_1$–C$_6$ perfluoroalkoxy, acetyl, —OR, —SR, —NRR, —N$^1$-piperidinyl, —N$^1$-piperazinyl[N$^4$—R], —N-pyrrolidinyl, —N-morpholino, —N-thiomorpholino, —N-hexahydroazepine, aryl, heteroaryl, substituted aryl, or substituted heteroaryl;
E' is hydrogen, halogen, —NO$_2$, —NRR, —R, —OR, —S(O)$_a$R, —S(CH$_2$)$_n$E, —(CH$_2$)$_n$E, —O—(CH$_2$)$_n$E, —NR(CH$_2$)$_n$E, —CO$_2$R, —CONRR,

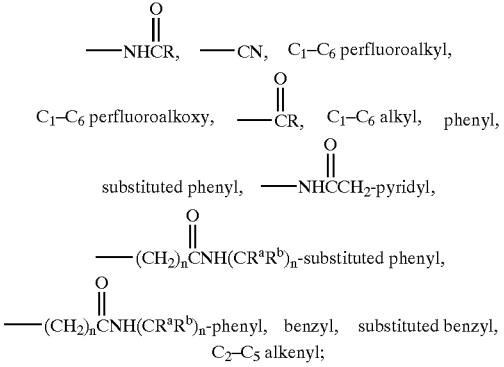

—NHCR, —CN, C$_1$–C$_6$ perfluoroalkyl,
C$_1$–C$_6$ perfluoroalkoxy, —CR, C$_1$–C$_6$ alkyl, phenyl,
substituted phenyl, —NHCCH$_2$-pyridyl,
—(CH$_2$)$_n$CNH(CR$^a$R$^b$)$_n$-substituted phenyl,
—(CH$_2$)$_n$CNH(CR$^a$R$^b$)$_n$-phenyl, benzyl, substituted benzyl, or C$_2$–C$_5$ alkenyl;

each n is independently 0 to 5 inclusive;
each a is independently 0, 1, or 2;
each m is independently 0, 2, 3, 4, or 5;
Y is CH$_2$, NR, O, or S;
A' is aryl, heteroaryl, substituted aryl or substituted heteroaryl, C$_3$–C$_6$ cycloalkyl or C$_3$–C$_6$ substituted cycloalkyl, provided that any substituents are not —NO$_2$;

B is pyrrolyl, substituted pyrrolyl, imidazolyl, substituted imidazolyl, oxazolyl, substituted oxazolyl, thiazolyl, substituted thiazolyl,

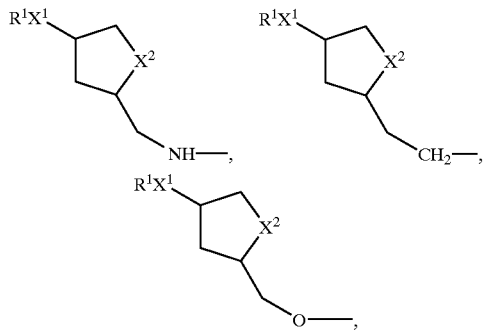

—NR$^1$—(CH$_2$)$_n$—(CHX$^3$)—(CH$_2$)$_n$—SR$^1$,
—S—(CH$_2$)$_n$—(CHX$^3$)—(CH$_2$)$_n$—SR$^1$, or
—(CH$_2$)$_n$—(CHX$^3$)—(CH$_2$)$_n$—SR$^1$;

X$^1$ is S or NR$^1$;
X$^2$ is NR$^1$ or CH$_2$;
R$^1$ is hydrogen or C$_1$–C$_6$ alkyl;
X$^3$ is hydrogen, —NR$^1$R$^1$ or —C$_1$–C$_6$ alkyl, and the pharmaceutically acceptable salts, esters, amides, and prodrugs thereof In a preferred embodiment of the compounds of Formula III, Q is O.

In a preferred embodiment of the compounds of Formula III, E' is hydrogen.

In a preferred embodiment of the compounds of Formula III, Y is O.

In a preferred embodiment of the compounds of Formula III, A' is phenyl, substituted phenyl, pyridyl, substituted pyridyl, thienyl, substituted thienyl, furyl, substituted furyl, naphthyl, or substituted naphthyl.

In a more preferred embodiment of the compound of Formula III, A' is phenyl, substituted phenyl, thienyl, substituted thienyl, furyl, or substituted furyl.

In a preferred embodiment of the compounds of Formula III, B is imidazolyl or substituted imidazolyl.

In a most preferred embodiment, the present invention provides the compounds:

6-(2-Imidazole-1-yl-ethoxy)-3,4-dihydro-2H-naphthalen-1-one;

6-[2-(2-Methyl-imidazole-1-yl)-ethoxy]-3,4-dihydro-2H-naphthalen-1-one;

6-(2-Imidazole-1-yl-ethoxy)-2-pyridin-2-ylmethylene-3,4-dihydro-2H-naphthalen-1-one;

6-(2-Imidazole-1-yl-ethoxy)-2-(4-methylsulfanyl-benzylidene)-3,4-dihydro-2H-naphthalen-1-one;

2-(4-Bromo-benzylidene)-6-(2-imiddazole-1-yl-ethoxy)-3,4-dihydro-2H-naphthalen-1-one;

6-(2-Imidazole-1-yl-ethoxy)-2-pyridin-4-ylmethylene-3,4-dihydro-2H-naphthalen-1-one;

6-(2-Iridazole-1-yl-ethoxy)-2-(4-nitro-benzylidene)-3,4-dihydro-2H-naphthalen-1-one;

2-[4-(2-Diethylamino-ethoxy)-benzylidene]-6-(2-imidazole-1-yl-ethoxy)-3,4-dihydro-2H-naphthalen-1-one;

2-Benzylidene-6-(2-imidazole-1-yl-ethoxy)-3,4-dihydro-2H-naphthalen-1-one;

6-(2-Imidazole-1-yl-ethoxy)-2-(4-methylsulfanyl-benzyl)-3,4-dihydro-2H-naphthalen-1-one;

6-(2-Imidazole-1-yl-ethoxy)-2-thiophen-3-ylmethylene-3,4-dihydro-2H-naphthalen-1-one;

4-[6-(2-Imidazole-1-yl-ethoxy)-1-oxo-3,4-dihydro-1H-naphthalen-2-ylidenemethyl]-benzoic acid;

2-(4-Bromo-benzyl)-6-(2-imidazole-1-yl-ethoxy)-3,4-dihydro-2H-naphthalen-1-one;

6-(2-Imidazole-1-yl-ethoxy)-2-thiophen-2-ylmethylene-3,4-dihydro-2H-naphthalen-1-one;

6-(2-Imidazole-1-yl-ethoxy)-2-naphthalen-1-ylmethylene-3,4-dihydro-2H-naphthalen-1-one;

2-Furan-2-ylmethylene-6-(2-imidazole-1-yl-ethoxy)-3,4-dihydro-2H-naphthalen-1-one;

2-(4-Bromo-thiophen-2-ylmethylene)-6-(2-imidazole-1-yl-ethoxy)-3,4-dihydro-2H-naphthalen-1-one;

2-(5-Chloro-thiophen-2-ylmethylene)-6-(2-imidazole-1-yl-ethoxy)-3,4-dihydro-2H-naphthalen-1-one;

6-(2-Imidazole-1-yl-ethoxy)-2-(5-methylsulfanyl-thiophen-2-ylmethylene)-3,4-dihydro-2H-naphthalen-1-one;

6-(2-Imidazole-1-yl-ethoxy)-2-(3-phenoxy-thiophen-2-ylmethylene)-3,4-dihydro-2H-naphthalen-1-one;

2-[2,2']Bithiophenyl-5-ylmethylene-6-(2-imidazole-1-yl-ethoxy)-3,4-dihydro-2H-naphthalen-1-one;

2-Furan-3-ylmethylene-6-(2-imidazole-1-yl-ethoxy)-3,4-dihydro-2H-naphthalen-1-one;

6-(2-Imidazole-1-yl-ethoxy)-2-(4-methoxy-benzylidene)-3,4-dihydro-2H-naphthalen-1-one;

6-(2-Imidazole-1-yl-ethoxy)-2-(4-amino-benzylidene)-3,4-dihydro-2H-naphthalen-1-one;

6-(2-Imidazole-1-yl-ethoxy)-2-(2-methoxy-benzylidene)-3,4-dihydro-2H-naphthalen-1-one;

6-(2-Imidazole-1-yl-ethoxy)-2-thiazol-2-ylmethylene-3,4-dihydro-2H-naphthalene-1-one;

6-[2-(1H-Imidazole-4-yl)-ethoxy]-3,4-dihydro-2H-naphthalen-1-one;

6-[2-(1H-Imidazole-4-yl)-ethoxy]-2-thiophen-3-ylmethylene-3,4-dihydro-2H-naphthalen-1-one;

6-[2-(1H-Imidazole-4-yl)-ethoxy]-2-thiophen-2-ylmethylene-3,4-dihydro-2H-naphthalen-1-one;

2-Benzylidene-6-[2-(1H-imidazole-4-yl)-ethoxy]-3,4-dihydro-2H-naphthalen-1-one;

6-[2-(1H-Imidazole-4-yl)-ethoxy]-2-(4-methylsulfanyl-benzylidene)-3,4-dihydro-2H-naphthalen-1-one;

6-[2-(1H-Imidazole-4-yl)-ethoxy]-2-(5-methylsulfanyl-thiophen-2-ylmethylene)-3,4-dihydro-2H-naphthalen-1-one;

4-{6-[2-(1H-Imidazole-4-yl)-ethoxy]-1-oxo-3,4-dihydro-1H-naphthalen-2-ylidenemethyl}-benzamide, monohydrochloride;

N,N-Diethyl-4-{6-[2-(1H-imidazole-4-yl)-ethoxy]-1-oxo-3,4-dihydro-1H-naphthalen-2-ylidenemethyl}-benzamide, monohydrochloride;

4-{6-[2-(1H-Imidazole-4-yl)-ethoxy]-1-oxo-3,4-dihydro-1H-naphthalen-2-ylidenemethyl}-benzoic acid, ditrifluoroacetate;

2-(5-Chloro-thiophen-2-ylmethylene)-6-[2-(1H-imidazole-4-yl)-ethoxy]-3,4-dihydro-2H-naphthalen-1-one, hydrochloride;

6-[2-(1H-Imidazole4-yl)-ethoxy]-2-(5-methyl-thiophen-2-ylmethylene)-3,4-dihydro-2H-naphthalen-1-one;

6-[2-(1H-Imidazole-4-yl)-ethoxy]-2-(3-methyl-thiophen-2-ylmethylene)-3,4-dihydro-2H-naphthalen-1-one;

6-[2-(1H-Imidazole-4-yl)-ethoxy]-2-(1-phenyl-ethylidene)-3,4-dihydro-2H-naphthalen-1-one;

2-Furan-2-ylmethylene-6-[2-(1H-imiddazole-4-yl)-ethoxy]-3,4-dihydro-2H-naphthalen-1-one;

2-(4-Bromo-benzylidene)-6-[2-(1H-imidazole-4-yl)-ethoxy]-3,4-dihydro-2H-naphthalen-1-one;

5-{6-[2-(1H-Imidazol-4-yl)-ethoxy]-1-oxo-3,4-dihydro-1H-naphthalen-2-ylidenemethyl}-thiophene-2-carboxylic acid;

6-[3-(1H-Imidazole-4-yl)-propoxy]-3,4-dihydro-2H-naphthalen-1-one;

2-(Hydroxy-thiazol-2-yl-methyl)-6-(2-imidazole-1-yl-ethoxy)-3,4-dihydro-2H-naphthalen-1-one;

(E,E)-6-(2-Imidazole-1-yl-ethoxy)-2-(3-phenyl-allylidene)-3,4-dihydro-2H-naphthalen-1-one;

2-[(E)-1–Cyclohexylmethylidene]-6-[2-(1H-1-imidazolyl)ethoxy]-1,2,3,4-tetrahydro-1-naphthalenone, hydrochloride;

6-[2-(1H-1-Imidazolyl)ethoxyl-7-methyl-2-[(E)-1-(2-thienyl)methylidene]-1,2,3,4-tetrahydro-1-naphthalenone;

6-[2-(1H-1-Imidazolyl)ethoxy]-5-methyl-1,2,3,4-tetrahydro-1-naphthalenone;

6-[2-(1H-1-Imidazolyl)ethoxy]-5-methyl-2-[(E)-1-(2-thienyl)methylidene]-1,2,3,4-tetrahydro-1-naphthalenone;

7-[2-(1H-1-Imidazolyl)ethoxy]-3-[(E)-1-(2-thienyl)methylidene]-1,2,3,4-tetrahydro-4-quinolinone;

7-[2-(1H-1-Imidazolyl)ethoxy]-4H-4-chromenone;

7-[2-(1H-1-Imidazolyl)ethoxy]-4-chromanone;

7-[2-(1H-1-Imidazolyl)ethoxy]-3-[(E)-1-(2-thienyl)methylidene]-4-chromanone;

6-[2-(1H-1-Imidazolyl)ethoxy]-1,2,3,4-tetrahydro-1-naphthalenone oxime;

[6-(2-Imidazol-1-yl-ethoxy)-3,4-dihydro-2H-naphthalen-1-ylideneaminooxy]-acetic acid;

2-[6-(2-Imidazol-1-yl-ethoxy)-3,4-dihydro-2H-naphthalen-1-ylideneaminooxy]-N-(2-methyl-2-phenyl-propyl)-acetamide;

2-[(E)-1-(3–Chlorophenyl)methylidene]-6-[2-(1H-1-imidazolyl)ethoxy]-1,2,3,4-tetrahydro-1-naphthalenone;

2-[(E)-1-(4–Chlorophenyl)methylidene]-6-[2-(1H-1-imidazolyl)ethoxy]-1,2,3,4-tetrahydro-1-naphthalenone;

2-[(E)-1-(1,3-Benzodioxol-5-yl)methylidene]-6-[2-(1H-1-imidazolyl)ethoxy]-1,2,3,4-tetrahydro-1-naphthalenone;

2-[(E)-1-(4-Fluorophenyl)methylidene]-6-[2-(1H-1-imidazolyl)ethoxy]-1,2,3,4-tetrahydro-1-naphthalenone;

2-[(E)-1-(2,3-Dichlorophenyl)methylidene]-6-[2-(1H-1-imidazolyl)ethoxy]-1,2,3,4-tetrahydro-1-naphthalenone;

2-[(E)-1-(2,6-Dichlorophenyl)methylidene]-6-[2-(1H-1-imidazolyl)ethoxy]-1,2,3,4-tetrahydro-1-naphthalenone;

2-[(E)-1-(3,4-Dichlorophenyl)methylidene]-6-[2-(1H-1-imidazolyl)ethoxy]-1,2,3,4-tetrahydro-1-naphthalenone;

2-[(E)-1-(3,5-Dichlorophenyl)methylidene]-6-[2-(1H-1-imidazolyl)ethoxy]-1,2,3,4-tetrahydro-1-naphthalenone;

2-[(E)-1-(2,5-Dimethoxyphenyl)methylidene]-6-[2-(1H-1-imidazolyl)ethoxy]-1,2,3,4-tetrahydro-1-naphthalenone;

2-[(E)-1-(2,3-Dimethoxyphenyl)methylidene]-6-[2-(1H-1-imidazolyl)ethoxy]-1,2,3,4-tetrahydro-1-naphthalenone;

6-[2-(1H-1-Imidazolyl)ethoxy]-2-(E)-1-[2-(trifluoromethyl)phenyl]methylidene -1,2,3,4-tetrahydro-1-naphthalenone;

6-[2-(1H-1-Imidazolyl)ethoxy]-2-[(E)-1-(2,4,6-trimethoxyphenyl)methylidene]-1,2,3,4-tetrahydro-1-naphthalenone;

6-[2-(1H-1-Imidazolyl)ethoxy]-2-[(E)-1-(2,3,4-trimethoxyphenyl)methylidene]-1,2,3,4-tetrahydro-1-naphthalenone;

6-[2-(1H-1-Imidazolyl)ethoxy]-2-[(E)-1-(4-iodophenyl)methylidene]-1,2,3,4-tetrahydro-1-naphthalenon;

2-(E)-1-[4-(Dimethylamino)phenyl]methylidene-6-[2-(1H-1-imidazolyl)ethoxy]-1,2,3,4-tetrahydro-1-naphthalenone;

2-(E)-1-[4-(tert-Butyl)phenyl]methylidene-6-[2-(1H-1-imidazolyl)ethoxy]-1,2,3,4-tetrahydro-1-naphthalenone;

6-[2-(1H-1-Imidazolyl)ethoxy]-2-[(E)-1-(3-methoxyphenyl)methylidene]-1,2,3,4-tetrahydro-1-naphthalenone;

6-[2-(1H-1-Imidazolyl)ethoxy]-2-[(E)-1-(3-methylphenyl)methylidene]-1,2,3,4-tetrahydro-1-naphthalenone;

2-(E)-1-[4-(Diethylamino)phenyl]methylidene-6-[2-(1H-1-imidazolyl)ethoxy]-1,2,3,4-tetrahydro-1-naphthalenone, di-trifluoroacetic acid salt;

7-[2-(1H-1-Imidazolyl)ethoxy]-2-phenyl-chromanone;

7-[2-(1H-1-Imidazolyl)ethoxy]-2-phenyl-4H-4-chromenone;

6-[2-(1H-1-Imidazolyl)propoxy]-1,2,3,4-tetrahydro-1-naphthalenone;

6-[2-(1H-1-Imidazolyl)propoxy]-2-[(E)-1-(2-thienyl)methylidene]-1,2,3,4-tetrahydro-1-naphthalenone;

6-[2-(1H-1-Imidazolyl)-1-phenylethoxy]-1,2,3,4-tetrahydro-1-naphthalenone;

6-(2-Imidazol-1-yl-1-phenyl-ethoxy)-2-thiophen-2-ylmethylene-3,4-dihydro-2H-naphthalen-1-one;

2-[6-(2-Imidazol-1-yl-ethoxy)-3,4-dihydro-2H-naphthalen-1-ylideneaminooxy]-N-(1-phenyl-cyclobutylmethyl)-acetamide; and 7-[2-(1H-Imidazolyl)ethoxy]-2,2-dimethyl-4-chromanone.

The present invention also provides a pharmaceutically acceptable composition that comprises a compound of Formula I, II, III, or IV The present invention also provides a method of treating or preventing restenosis, the method comprising administering to a patient having restenosis or at risk of having restenosis a therapeutically effective amount of Formula I, II, III, or IV The present invention also provides a method of treating cancer, the method comprising administering to a patient having cancer a therapeutically effective amount of a compound of Formula I, II, III, or IV In a preferred embodiment of the method of treating cancer, the cancer is lung, colon, pancreatic, thyroid, or bladder cancer.

The present invention also provides a method of treating atherosclerosis, the method comprising administering to a patient having atherosclerosis a therapeutically effective amount of a compound of Formula I, II, III, or IV Also provided is a method of treating or preventing restenosis or atherosclerosis or treating cancer, the method of comprising administering to a patient having restenosis or atherosclerosis, or at risk of having restenosis or atherosclerosis, or having cancer a therapeutically effective amount of a compound of Formula I

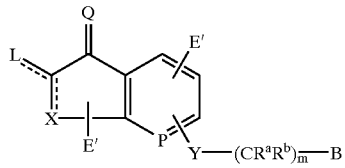

wherein Q is O, —NOR, —N—NRR, —NOCH$_2$CO$_2$R$^a$,

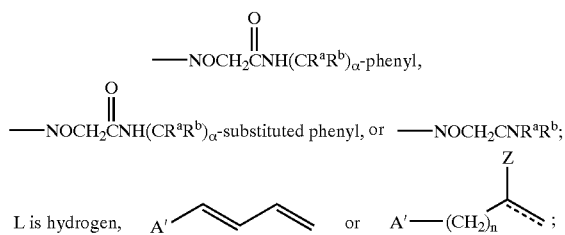

each R$^a$ or R$^b$ is independently hydrogen, C$_1$–C$_6$ alkyl, C$_2$–C$_6$ alkenyl, phenyl, or substituted phenyl, or R$^a$ and R$^b$ along with the carbon atom to which they are bonded form a C$_3$–C$_6$ cycloalkyl ring;

each R is independently hydrogen, C$_1$–C$_6$ alkyl, C$_3$–C$_6$ cycloalkyl, benzyl, C$_2$–C$_6$ alkenyl, phenyl, or substituted phenyl;

Each - - - is a bond or absent;

P is N

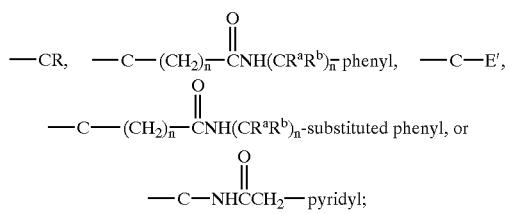

X is CH$_2$, CH$_2$O, CH$_2$S, CH$_2$SO, CH$_2$SO$_2$, CH$_2$NR, or

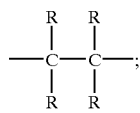

Z is hydrogen when L is

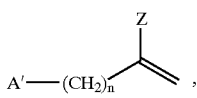

and

Z is —NRR, —R, —OR, —SR, —(CH$_2$)$_n$E, O(CH$_2$)$_n$E, —NR(CH$_2$)$_n$E, —S(CH$_2$)$_n$E, —N$^1$-piperidinyl, —N$^1$-piperazinyl[N$^4$—R], —N-pyrrolidinyl, —N-morpholino, —N-thiomorpholino, —N-hexahydroazepine, or an amino acid having the structure

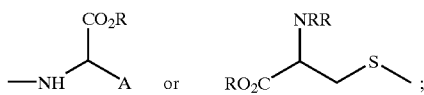

when L is

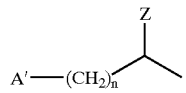

where A is a side chain of the amino acid glycine, alanine, valine, leucine, isoleucine, phenylalanine, proline, serine, threonine, tyrosine, asparagine, glutamine, lysine, arginine, tryptophan, histidine, cysteine, methionine, aspartic acid, or glutamic acid;

E is hydrogen, halogen, —CO$_2$R, —CONRR, —CN, —NO$_2$, C$_1$–C$_6$ perfluoroalkyl, C$_1$–C$_6$ perfluoroalkoxy, acetyl, —OR, —SR, —NRR, —N$^1$-piperidinyl, —N$^1$-piperazinyl[N$^4$—R], —N-pyrrolidinyl, —N-morpholino, —N-thiomorpholino, —N-hexahydroazepine, aryl, heteroaryl, substituted aryl, or substituted heteroaryl;

each E' is independently hydrogen, halogen, —NO$_2$, —NRR, —R, —OR, —S(O)$_a$(R,

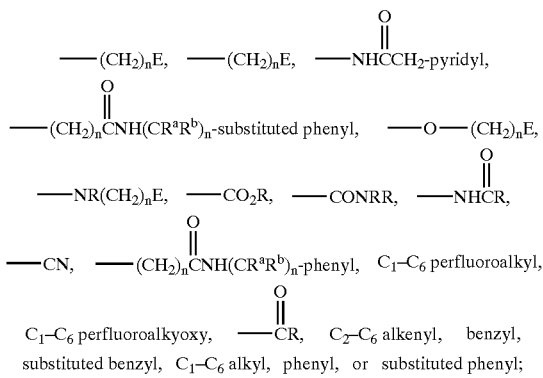

C$_1$–C$_6$ perfluoroalkyoxy, —CR, C$_2$–C$_6$ alkenyl, benzyl, substituted benzyl, C$_1$–C$_6$ alkyl, phenyl, or substituted phenyl;

each n is independently 0 to 5 inclusive;
each a is independently 0, 1, or 2;
each m is independently 0, 2, 3, 4, or 5;
Y is CH$_2$, NR, O, SO, SO$_2$, or S.;
A' is aryl, heteroaryl, substituted aryl or substituted heteroaryl, C$_1$–C$_6$ substituted alkyl,

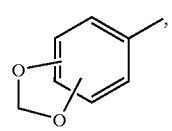

C$_3$–C$_6$ cycloalkyl or C$_3$–C$_6$ substituted cycloalkyl;

B is pyrrolyl, substituted pyrrolyl, imidazolyl, substituted imidazolyl, oxazolyl, substituted oxazolyl, thiazolyl, substituted thiazolyl,

15

[Structures shown: three pyrrolidine-type ring structures with $R^1X^1$ substituent and $X^2$ in ring, with -NH-, -CH$_2$-, and -O- linkers respectively]

—NR1—(CH$_2$)$_n$—(CHX$^3$)—(CH$_2$)$_n$—SR$^1$,
—S—(CH$_2$)$_n$—(CHX$^3$)—(CH$_2$)$_n$—SR$^1$, or
—(CH$_2$)$_n$—(CHX$^3$)—(CH$_2$)$_n$—SR$^1$;
X$^1$ is S or NR$^1$;
X$^2$ is NR$^1$ or CH$_2$;
R$^1$ is hydrogen or C$_1$-C$_6$ alkyl;
X$^3$ is hydrogen —NR$^1$R$^1$ or —C$_1$-C$_6$ alkyl, and the pharmaceutically acceptable salts, esters, amides, and prodrugs thereof Also provided are compounds having the Formula IV

IV

[Structure: bicyclic compound with Q, J, X, Y, E', (CR$^a$R$^b$)$_{\overline{m}}$—B substituents]

wherein
each J is independently C$_1$-C$_6$ alkyl;
Y is CH$_2$, NR, O, SO, SO$_2$, or S;
each m is independently 0, 2, 3, 4, or 5;
each R$^a$ or R$^b$ is independently hydrogen, C$_1$-C$_6$ alkyl, C$_2$-C$_6$ alkenyl, phenyl, substituted phenyl, or R$^a$ and R$^b$ together with the carbon atom to which they are bonded form a C$_3$-C$_6$ cycloalkyl ring;
B is pyrrolyl, substituted pyrrolyl, imidazolyl, substituted imidazolyl, oxazolyl, substituted oxazolyl, thiazolyl, substituted thiazolyl,

[Structures shown: three pyrrolidine-type ring structures with $R^1X^1$ substituent and $X^2$ in ring, with -NH-, -CH$_2$-, and -O- linkers respectively]

—NR$^1$—(CH$_2$)$_n$—(CHX$^3$)—(CH$_2$)$_n$—SR$^1$,
—S—(CH$_2$)$_n$—(CHX$^3$)—(CH$_2$)$_n$—SR$^1$, or
—(CH$_2$)$_n$—(CHX$^3$)—(CH$_2$)$_n$—SR$^1$;
X$^1$ is S or NR$^1$;
X$^2$ is NR$^1$ or CH$_2$;
R$^1$ is hydrogen or C$_1$-C$_6$ alkyl;

X$^3$ is hydrogen —NR$^1$R$^1$ or —C$_1$-C$_6$ alkyl;
X is CH$_2$ or —O—;
Q is O, —NOR, —N—NRR, —NOCH$_2$CO$_2$R$^a$, —NOCH$_2$C(O)NH(CR$^a$R$^b$)$_\alpha$-phenyl, —NOCH$_2$C(O)NH(CR$^a$R$^b$)$_\alpha$-substituted phenyl, or —NOCH$_2$C(O)NR$^a$R$^b$;

each R is independently hydrogen, C$_1$-C$_6$ alkyl, C$_3$-C$_6$ cycloalkyl, benzyl, C$_2$-C$_6$ alkenyl, phenyl, or substituted phenyl;
each E' is independently hydrogen, halogen, —NO$_2$, —NRR, —R, —OR, —S(O)$_\alpha$R, —S(CH$_2$)$_n$E, —(CH$_2$)$_n$E, —(CH$_2$)$_n$E, —NHC(O)CH$_2$—pyridyl, —(CH$_2$)$_n$C(O)NH(CR$^a$R$^b$)$_n$-substituted phenyl, —O—(CH$_2$)$_n$E, —NR(CH$_2$)$_n$E, —CO$_2$R, —CONRR, —NHC(O)R, —CN, —(CH$_2$)$_n$C(O)NH(CR$^a$R$^b$)$_{\overline{n}}$—phenyl, C$_1$-C$_6$ perfluoroalkyl, C$_1$-C$_6$ perfluoroalkoxy, —C(O)R, C$_2$-C$_6$ alkenyl, benzyl, substituted benzyl, substituted benzyl, C$_1$-C$_6$ alkyl, phenyl, or substituted phenyl;

each α is independently 0, 1, or 2;
each n is independently 0 to 5;
E is hydrogen, halogen, —CO$_2$R, —CONRR, —CN, —NO$_2$, C$_1$-C$_6$ perfluoroalkyl, C$_1$-C$_6$ perfluoroalkoxy, acetyl, —OR, —SR, —NRR, —N$^1$-piperidinyl, —N$^1$-piperazinyl[N$^4$—R], —N-pyrrolidinyl, —N-morpholino, —N-thiomorpholino, —N-hexahydroazepine, aryl, heteroaryl, substituted aryl, or substituted heteroaryl;
and the pharmaceutically acceptable salts, esters, amides, and prodrugs thereof Also provided is a pharmaceutically acceptable composition that comprises a compound of Formula IV Also provided is a method of treating or preventing restenosis or atherosclerosis, the method comprising administering to a patient having restenosis or atherosclerosis or at risk of having restenosis or atherosclerosis a therapeutically effective amount of a compound of Formula IV Also provided is a method of treating cancer, the method comprising administering to a patient having cancer a therapeutically effective amount of a compound of Formula IV

DETAILED DESCRIPTION OF THE INVENTION

The present invention provides compounds having the Formula I

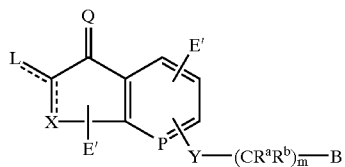

wherein Q is O, —NOR, —N—NRR, —NOCH$_2$CO$_2$R$^a$,

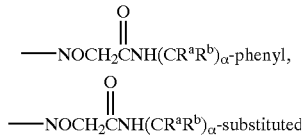

L is hydrogen,

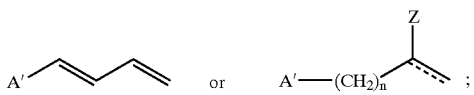

each R$^a$ or R$^b$ is independently hydrogen, C$_1$–C$_6$ alkyl, C$_2$–C$_6$ alkenyl, phenyl, or substituted phenyl, or R$^a$ and R$^b$ along with the carbon atom to which they are bonded form a C$_3$–C$_6$ cycloalkyl ring;

each R is independently hydrogen, C$_1$–C$_6$ alkyl, C$_3$–C$_6$ cycloalkyl, benzyl, C$_2$–C$_6$ alkenyl, phenyl, or substituted phenyl;

Each - - - is a bond or absent;

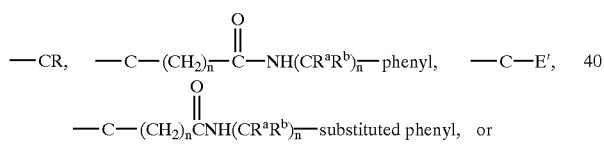

X is CH$_2$, CH$_2$O, CH$_2$S, CH$_2$SO, CH$_2$SO$_2$, CH$_2$NR, or

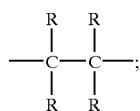

Z is hydrogen when L is

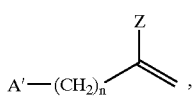

and

Z is —NMR, —R, —OR, —SR, —(CH$_2$)$_n$E, —O(CH$_2$)$_n$E, —NR(CH$_2$)$_n$E, —S(CH$_2$)$_n$E, —N$^1$-piperidinyl, —N$^1$-piperazinyl[N$^4$—R], —N-pyrrolidinyl, —N-morpholino, —N-thiomorpholino, —N-hexahydroazepine, or an amino acid having the structure

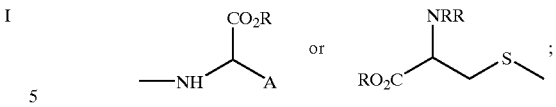

when L is

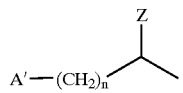

where A is a side chain of the amino acid glycine, alanine, valine, leucine, isoleucine, phenylalanine, proline, serine, threonine, tyrosine, asparagine, glutamine, lysine, arginine, tryptophan, histidine, cysteine, methionine, aspartic acid, or glutamic acid;

E is hydrogen, halogen, —CO$_2$R, —CONRR, —CN, —NO$_2$, C$_1$–C$_6$ perfluoroalkyl, C$_1$–C$_6$ perfluoroalkoxy, acetyl, —OR, —SR, —NRR, —N$^1$-piperidinyl, —N$^1$-piperazinyl[N$^4$—R], —N-pyrrolidinyl, —N-morpholino, —N-thiomorpholino, —N-hexahydroazepine, aryl, heteroaryl, substituted aryl, or substituted heteroaryl;

each E' is independently hydrogen, halogen, —NO$_2$, —NRR, —R, —OR, —S(O)$_\alpha$R,

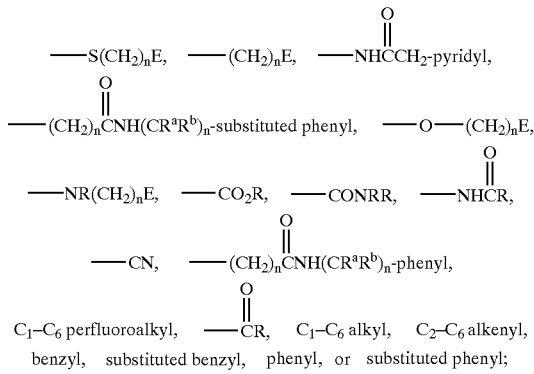

each n is independently 0 to 5 inclusive;
each α is independently 0, 1, or 2;
each a is independently 0, 2, 3, 4, or 5;
Y is CH$_2$, NR, O, SO, SO$_2$, or S;
A' is aryl, heteroaryl, substituted aryl, substituted heteroaryl, C$_1$–C$_6$ alkyl, C$_1$–C$_6$ substituted alkyl,

C$_3$–C6 cycloalkyl or C$_3$–C$_6$ substituted cycloalkyl, provided any substituents are not —NO$_2$;

B is pyrrolyl, substituted pyrrolyl, imidazolyl, substituted imidazolyl, oxazolyl, substituted oxazolyl, thiazolyl, substituted thiazolyl,

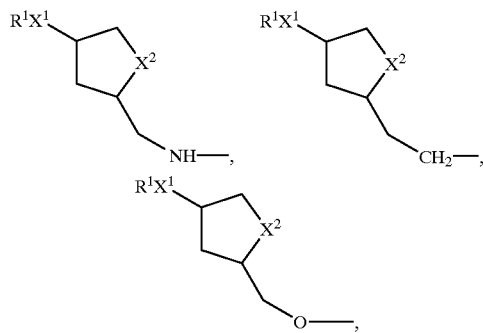

—NR$^1$—(CH$_2$)$_n$—(CHX$^3$)—(CH$_2$)$_n$—SR$^1$,
—S—(CH$_2$)$_n$—(CHX$^3$)—(CH$_2$)$_n$—SR$^1$, or
—(CH$_2$)$_n$—(CHX$^3$)—(CH$_2$)$_n$—SR$^1$;

$X^1$ is S or NR$^1$;
$X^2$ is NR$^1$ or CH$_2$;
$R^1$ is hydrogen or C$_1$–C$_6$ alkyl;
$X^3$ is hydrogen —NR$^1$R$^1$ or —C$_1$–C$_6$ alkyl, and the pharmaceutically acceptable salts, esters, amides, and prodrugs thereof, provided that the compound is not 5-(2-imidazole-1-yl-ethoxy)-indan-1-one.

Also provided by the present invention are compounds having the Formula II

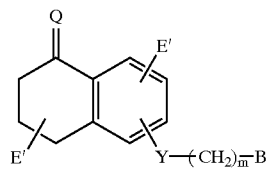

II wherein Q is O, —NOR, —N—NRR, —NOCH$_2$CO$_2$R$^a$,

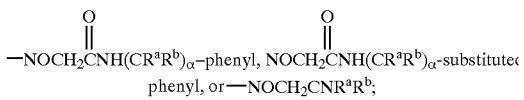

each R$^a$ or R$^b$ is independently hydrogen, C$_1$–C$_6$ alkyl, C$_2$–C$_6$ alkenyl, phenyl, or substituted phenyl, or R$^a$ and R$^b$ along with the carbon atom to which they are bonded form a C$_3$–C$_6$ cycloalkyl ring;

each R is independently hydrogen, C$_1$–C$_6$ alkyl, C$_2$–C$_6$ alkenyl, C$_1$–C$_6$ cycloalkyl, benzyl, C$_2$–C$_6$ alkenyl, phenyl, or substituted phenyl;

E is hydrogen, halogen, —CO$_2$R, —CONRR, —CN, —NO$_2$, C$_1$–C$_6$ perfluoroalkyl, C$_1$–C$_6$ perfluoroalkoxy, acetyl, —OR, —SR, —NRR, —N$^1$-piperidinyl, —N$^1$-piperazinyl[N$^4$—R], —N-pyrrolidinyl, —N-morpholino, —N-thiomorpholino, —N-hexahydroazepine, aryl, heteroaryl, substituted aryl, or substituted heteroaryl;

each E' is independently hydrogen, halogen, —NO$_2$, —NRR, —R, —OR,

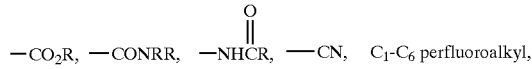

—CO$_2$R, —CONRR, —NHCR, —CN, C$_1$–C$_6$ perfluoroalkyl,

C$_1$–C$_6$ perfluoroalkoxy, —CR, C$_1$–C$_6$ alkyl, C$_2$–C$_6$ alkenyl,

—NHCCH$_2$-pyridyl, —(CH$_2$)$_n$CNH(CR$^a$R$^b$)$_n$-substituted phenyl,

—(CH$_2$)$_n$CNH(CR$^a$R$^b$)$_n$-phenyl, benzyl, substituted benzyl, phenyl, or substituted phenyl;

each n is independently 0 to 5 inclusive;
each α is independently 0, 1, or 2;
each m is independently 0, 2, 3, 4, or 5;
Y is CH$_2$, NR, O, SO, SO$_2$, or S;
B is pyrrolyl, substituted pyrrolyl, imidazolyl, substituted imidazolyl, oxazolyl, substituted oxazolyl, thiazolyl, substituted thiazolyl,

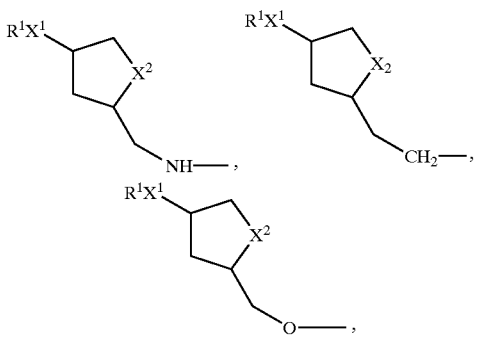

—NR$^1$—(CH$_2$)$_n$—(CHX$^3$)—(CH$_2$)$_n$—SR$^1$,
—S—(CH$_2$)$_n$—(CHX$^3$)—(CH$_2$)$_n$—SR$^1$, or
—(CH$_2$)$_n$—(CHX$^3$)—(CH$_2$)$_n$—SR$^1$;

$X^1$ is S or NR$^1$;
$X^2$ is NR$^1$ or CH$_2$;
$R^1$ is hydrogen or C$_1$–C$_6$ alkyl;
$X^3$ is hydrogen, —NR$^1$R$^1$, or —C$_1$–C$_6$ alkyl, and the pharmaceutically acceptable salts, esters, amides and prodrugs thereof Also provided by the present invention are compounds having the Formula III

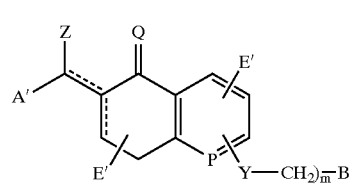

III wherein Q is O, —NOR, or —N—NRR;

Z is hydrogen when - - - is absent and Z is —NRR, —R, —OR, —SR, —(CH$_2$)$_n$E, —O(CH$_2$)$_n$E, —NR(CH$_2$)$_n$E, —S(CH$_2$)$_n$E, —N$^1$-piperidinyl, —N$^1$-piperazinyl[N$^4$—R], —N-pyrrolidinyl, —N-morpholino, —N-thiomorpholino, —N-hexahydroazepine, or an amino acid having the structure

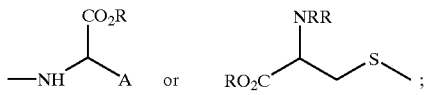

where A is a side chain of the amino acid glycine, alanine, valine, leucine, isoleucine, phenylalanine, proline, serine, threonine, tyrosine, asparagine, glutamine, lysine, arginine, tryptophan, histidine, cysteine, methionine, aspartic acid, or glutamic acid;
when - - - is a bond;
each $R^a$ or $R^b$ is independently hydrogen, $C_1$–$C_6$ alkyl, $C_2$–$C_6$ alkenyl, phenyl, or substituted phenyl, or $R^a$ and $R^b$ along with the carbon atom to which they are bonded form a $C_3$–$C_6$ cycloalkyl ring;
each R is independently hydrogen, $C_1$–$C_6$ alkyl, $C_3$–$C_6$ cycloalkyl, benzyl, $C_2$–$C_6$ alkenyl, phenyl, or substituted phenyl;

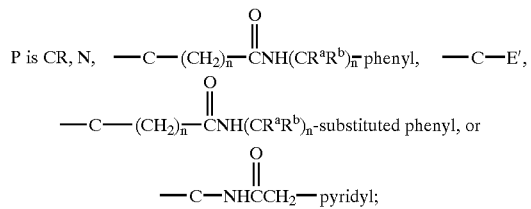

Each - - - is a bond or absent;
E is hydrogen, halogen, —$CO_2R$, —CONRR, —CN, —$NO_2$, $C_1$–$C_6$ perfluoroalkyl, $C_1$–$C_6$ perfluoroalkoxy, acetyl, —OR, —SR, —NRR, —$N^1$-piperidinyl, —$N^1$-piperazinyl[$N^4$—R], —N-pyrrolidinyl, —N-morpholino, —N-thiomorpholino, —N-hexahydroazepine, aryl, heteroaryl, substituted aryl, or substituted heteroaryl;
E' is hydrogen, halogen, —$NO_2$, —NRR, —R, —OR, —$S(O)_\alpha R$, —$S(CH_2)_nE$, —$(CH_2)_nE$, —O—$(CH_2)_nE$, —$NR(CH_2)_nE$, —$CO_2R$, —CONRR,

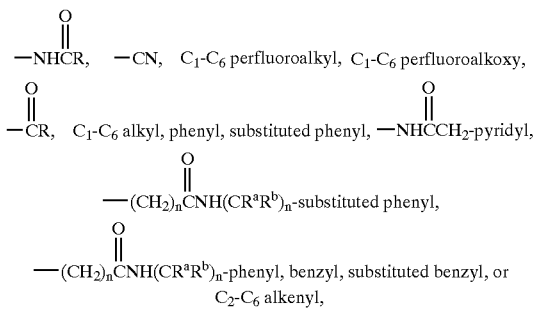

each n is independently 0 to 5 inclusive;
each α is independently 0, 1, or 2;
each m is independently 0, 2, 3, 4, or 5;
Y is $CH_2$, NR, O, or S;
A' is aryl, heteroaryl, substituted aryl or substituted heteroaryl, $C_3$–$C_6$ cycloalkyl or $C_3$–$C_6$ substituted cycloalkyl, provided that any substituents are not —$NO_2$;
B is pyrrolyl, substituted pyrrolyl, imidazolyl, substituted imidazolyl, oxazolyl, substituted oxazolyl, thiazolyl, substituted thiazolyl,

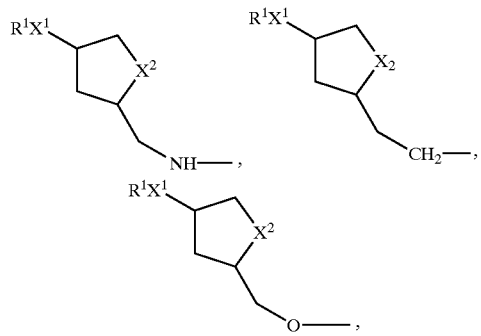

—$NR^1$—$(CH_2)_n$—$(CHX^3)$—$(CH_2)_n$—$SR^1$,
—$S(CH_2)_n$—$(CHX^3)$—$(CH_2)_n$—$SR^1$, or
—$(CH_2)_n$—$(CHX^3)$—$(CH_2)_n$—$SR^1$;
$X^1$ x is S or $NR^1$;
$X^2$ is $NR^1$ or $CH_2$;
$R^1$ is hydrogen or $C_1$–$C_6$ alkyl;
$X^3$ is hydrogen, —$NR^1R^1$ or —$C_1$–$C_6$ alkyl, and the pharmaceutically acceptable salts, esters, amides, and prodrugs thereof.

The present invention also provides compounds having the Formula IV

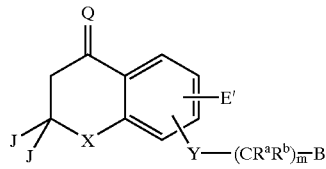

IV wherein
each J is independently $C_1$–$C_6$ alkyl;
Y is $CH_2$, NR, O, SO, $SO_2$, or S;
each m is independently 0, 2, 3, 4, or 5;
each $R^a$ or $R^b$ is independently hydrogen, $C_1$–$C_6$ alkyl, $C_2$–$C_6$ alkenyl, phenyl, substituted phenyl, or $R^a$ and $R^b$ together with the carbon atom to which they are bonded form a $C_3$–$C_6$ cycloalkyl ring;
B is pyrrolyl, substituted pyrrolyl, imidazolyl, substituted imidazolyl, oxazolyl, substituted oxazolyl, thiazolyl, substituted thiazolyl,

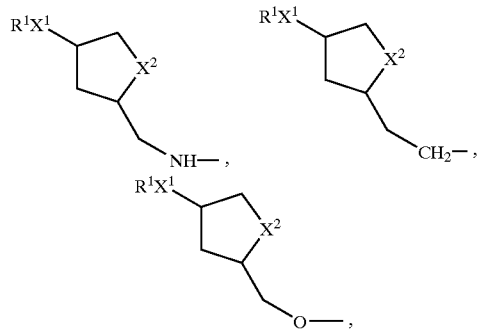

—$NR^1$—$(CH_2)_n$—$(CHX^3)$—$(CH_2)_n$—$SR^1$,
—S—$(CH_2)_n$—$(CHX^3)$—$(CH_2)_n$—$SR^1$, or
—$(CH_2)_n$—$(CHX^3)$—$(CH_2)_n$—$SR^1$;
$X^1$ is S or $NR^1$;
$X^2$ is $NR^1$ or $CH_2$;

$R^1$ is hydrogen or $C_1-C_6$ alkyl;
$X^3$ is hydrogen $-NR^1R^1$ or $-C_1-C_6$ alkyl;
X is $CH_2$ or $-O-$;
Q is O, $-NOR$, $-N-NRR$, $-NOCH_2CO_2R^a$,

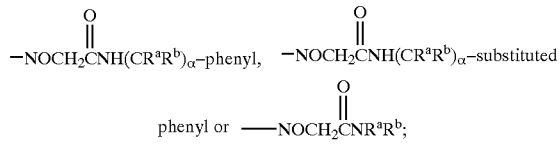

each R is independently hydrogen, $C_1-C_6$ alkyl, $C_3-C_6$ cycloalkyl, benzyl, $C_2-C_6$ alkenyl, phenyl, or substituted phenyl;
each E' is independently hydrogen, halogen, $-NO_2$, $-NRR$, $-R$, $-OR$, $-S(O)_aR$,

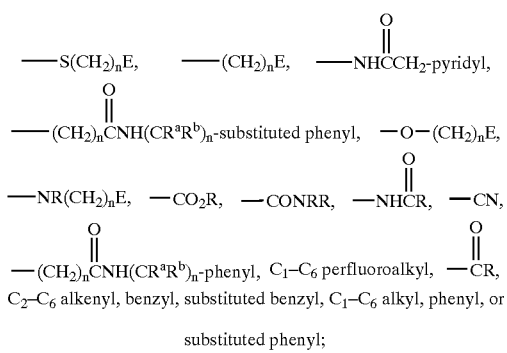

each a is independently 0, 1, or 2;
each n is independently 0 to 5;
E is hydrogen, halogen, $-CO_2R$, $-CONRR$, $-CN$, $-NO_2$, $C_1-C_6$ perfluoroalkyl, $C_1-C_6$ perfluoroalkoxy, acetyl, $-OR$, $-SR$, $-NRR$, $-N^1$-piperidinyl, $-N^1$-piperazinyl$[N^4-R]$, $-N$-pyrrolidinyl, $-N$-morpholino, $-N$-thiomorpholino, $-N$-hexahydroazepine, aryl, heteroaryl, substituted aryl, or substituted heteroaryl;
and the pharmaceutically acceptable, salts, esters, amides, and prodrugs thereof.

It is noted that the symbol - - - represents a bond or is absent.

In Formulas I and III, the symbol - - - is intended to signify a double bond either in the ring containing Q or exo to the ring. Preferably, the double bond is either exo to the ring or in the ring, but not both.

The term "alkyl" means a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents listed below for aryl.

The term "cycloalkyl" means a saturated hydrocarbon ring which contains from 3 to 7 carbon atoms, for example, cyclopropyl, cyclobutyl, cyclopentyl, cyclohexyl, adamantyl, and the like.

The term "aryl" means an aromatic ring which is a phenyl, 5-fluorenyl, 1-naphthyl, or 2-naphthyl group, unsubstituted or substituted by 1 to 3 substituents selected from alkyl, O-alkyl and S-alkyl, OH, SH, F, $-CN$, Cl, Br, I, $CF_3$, $NO_2$, $NH_2$, $NHCH_3$, $N(CH_3)_2$, NHCO-alkyl, $(CH_2)_mCO_2H$, $(CH_2)_mCO_2$-alkyl,

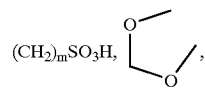

$-NH$ alkyl, $-N(alkyl)_2$, $-(CH_2)_mPO_3H_2$, $(CH_2)_mPO_3(alkyl)_2$, $(CH_2)_{m-k}SO_2NH_2$, and $(CH_2)_mSO_2NH$-alkyl wherein alkyl is defined as above and m is 0, 1, 2, or 3.

The term "heteroaryl" means an aromatic ring containing one or more heteroatoms. Examples of heteroaryl radicals include thienyl, furanyl, pyrrolyl, pyridyl, imidazoyl, or indolyl group, substituted or unsubstituted by 1 or 2 substituents from the group of substituents described above for aryl. Examples of heteroatoms include nitrogen, oxygen, sulfur, and phosphorus.

The symbol "-" means a bond.

The term "patient" means all animals including humans. Examples of patients include humans, cows, dogs, cats, goats, sheep, and pigs.

A "therapeutically effective amount" is an amount of a compound of the present invention that when administered to a patient ameliorates a symptom of restenosis, cancer, or atherosclerosis or prevents restenosis. A therapeutically effective amount of a compound of the present invention can be easily determined by one skilled in the art by administering a quantity of a compound to a patient and observing the result. In addition, those skilled in the art are familiar with identifying patients having cancer, restenosis, or atherosclerosis or who are at risk of having restenosis.

The term "cancer" includes, but is not limited to, the following cancers:
  breast;
  ovary;
  cervix;
  prostate,
  testis;
  esophagus;
  glioblastoma;
  neuroblastoma;
  stomach;
  skin, keratoacanthoma;
  lung, epidermoid carcinoma, large cell carcinoma, adenocarcinoma;
  bone;
  colon, adenocarcinoma, adenoma;
  pancreas, adenocarcinoma;
  thyroid, follicular carcinoma, undifferentiated carcinoma, papillary carcinoma;
  seminoma;
  melanoma;
  sarcoma;
  bladder carcinoma;
  liver carcinoma and biliary passages;
  kidney carcinoma;
  myeloid disorders;
  lymphoid disorders, Hodgkins, hairy cells;
  buccal cavity and pharynx (oral), lip, tongue, mouth, pharynx;
  small intestine;
  colon-rectum, large intestine, rectum;
  brain and central nervous system; and leukemia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate-mesylate, glucoheptonate, lactobionate and laurylsulphonate salts, and the like. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," *J. Pharm. Sci.,* 1977;66:1–19 which is incorporated herein by reference.) Examples of pharmaceutically acceptable, non-toxic esters of the compounds of this invention include $C_1-C_6$ alkyl esters wherein the alkyl group is a straight or branched chain. Acceptable esters also include $C_5-C_7$ cycloalkyl esters as well as arylalkyl esters such as, but not limited to benzyl. $C_1-C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1-C_6$ alkyl amines and secondary $C_1-C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1-C_3$ alkyl primary amines and $C_1-C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V Stella, "Pro-drugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are hereby incorporated by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3- butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

The compounds of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The examples presented below are intended to illustrate particular embodiments of the invention, and are not intended to limit the scope of the specification or the claims in any way.

PFT Inhibitory Activity

The protein:farnesyl transferase (PFT) or farnesyl protein transferase (FPT) inhibitory activity of compounds of the present invention were assayed in HEPES buffer (pH 7.4) containing 5 mM potassium phosphate and 20 $\mu$M $ZnCl_2$. The solution also contained 5 mM DTT (dithiothreitol), 5 mM $MgCl_2$, and 0.1% PEG 8000. Assays were performed in 96 well plates (Wallec) and employed solutions composed of varying concentrations of a compound of the present invention in 10% DMSO (dimethylsulfoxide). Upon addition of both substrates, radiolabeled farnesyl pyrophosphate ([$1^3$H], specific activity 15–30 Ci/mmol, final concentration 134 nM) and (biotinyl)-Ahe-Thr-Lys-Cys-Val-Ile-Met ([3aS[3a alpha, 4 beta, 6a alpha]-hexahydro-2-oxo-1H-thieno[3,4-d] imidazole-5-pentanoic acid]-[7-aminoheptanoic acid]-Thr-Lys-Cys-Val-Ile-Met) (Ahe is 7-aminoheptanoic acid, Thr is threonine, Lys is lysine, Cys is cysteine, Val is valine, Ile is isoleucine, and Met is methionine) (final concentration 0.2 $\mu$M), the enzyme reaction was started by addition of SF9 affinity purified rat FPT. After incubation at 30° C. for 30 minutes, the reaction was terminated by diluting the reaction 2.5-fold with a stop buffer containing 1.5 M magnesium acetate, 0.2 M $H_3PO_4$, 0.5% BSA (bovine serum albumin), and strepavidin beads (Amersham) at a concentration of 1.3 mg/mL. After allowing the plate to settle for 30 minutes at room temperature, radioactivity was quantitated on a micro-beta counter (Model 1450, Wallec). The assay was also carried out without 5 mM potassium phosphate.

The compounds of Formula I through IV may be prepared according to the synthetic strategies described below in Schemes 1 through 5.

As exemplified for tetralones of Formula I, imidazole derivatives can be prepared by alkylation of the phenol with a dihaloalkane or similar alkane bearing two leaving groups followed by reaction with an appropriate nucleophile such as sodium imidazolide.

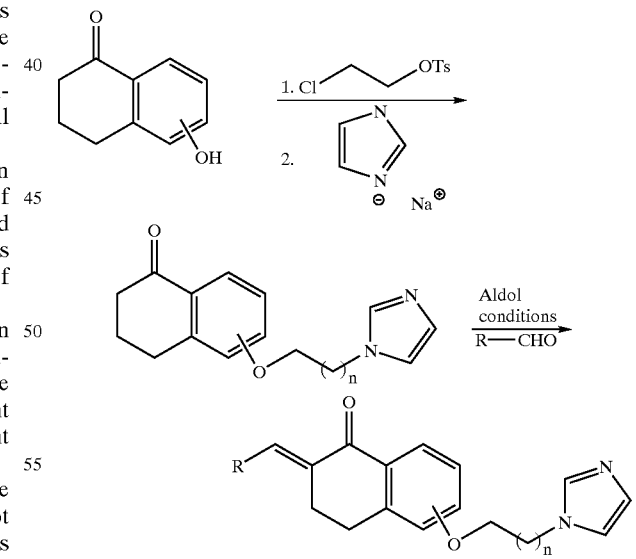

Scheme 1

Alternatively, as shown in Scheme 2, hydroxyalkylimidazoles can be coupled to the phenol under Mitsunobu conditions employing, for example, diethylazodicarboxylate and triphenylphosphine. Direct alkylation of the phenol with haloalkylimidazoles can also be employed.

Scheme 2

To obtain unsaturated compounds of Formula I, a ketone may be reacted with aldehydes under a variety of aldol conditions, for example KOH in EtOH, piperidine in acetic acid, or sulfuric acid in acetic acid.

The ketones can be alkylated to provide for the saturated compounds of Formula I according to Scheme 3. For example, enamines may be prepared by reaction with pyrrolidine under dehydrating conditions and subsequent alkylation with an alkyl halide. Alternatively, chiral or achiral hydrazides can be prepared by reaction of the ketone with achiral hydrazines (1,1-dimethyl-hydrazine, for example) or chiral hydrazines ((S) or (R)-1-amino-2-(methoxymethyl) pyrrolidine, for example) under dehydrating conditions and subsequent deprotonation with a strong base such as lithium diisopropyl amide (LDA) followed by an alkylating agent. Hydrolysis of the hydrazones can be achieved with aqueous acid or cleavage can be achieved with ozone treatment, as appropriate, according to known art.

Scheme 3

As an alternative to alkylation, reduction of the aldol products with hydrogen and an appropriate (chiral or achiral) catalyst or a hydride reagent such as potassium tri-sec-butylborohydride provide methods of obtaining the saturated analogs according to Scheme 4.

Scheme 4

The following abbreviations are used in the application.

HPLC High pressure liquid chromatography
CI-MS Chemical Ionization Mass Spectrometry
mp Melting point
rt Room temperature
TBF Tetrahydrofuran
APCI-MS Atmospheric pressure chemical ionization mass spectrometry
dec Decomposes
AcCN Acetonitrile
HOAc Acetic acid
$CHCl_3$ Chloroform
DCM Dichloromethane
DMF N,N'-Dimethylformamide
EtOAc Ethyl acetate
EtOH Ethanol
$Et_2O$ Diethyl ether
HCl Hydrochloric acid
$H_2O_2$ Hydrogen peroxide
$H_2SO_4$ Sulfuric acid
KOH Potassium hydroxide
MeCN Acetonitrile
MeOH Methanol NaH Sodium hydride
NaOH Sodium hydroxide
NaHCO$_3$ Sodium bicarbonate
iPrOH iso-Propanol
TFA Trifluoroacetic acid
Boc tertiary Butyloxycarbonyl
Ts Tosylate
Ph$_3$P Triphenylphosphine Melting points are uncorrected. Proton N ($^1$H-NMR) spectra were obtained at 400 MHz and are reported relative to tetramethylsilane (TMS). When indicated, analytical HPLC was performed on Vydac C18 peptide/protein columns eluting with gradients of water/acetonitrile containing 0.1% TFA. Flash chromatography was performed using Merck or ICN silica gel, 60A, 230–400 mesh. THF was distilled from Na/benzophenone and all other solvents were reagent grade and dried over 4A molecular sieves unless otherwise indicated.

EXAMPLE 1

6-(2-Imidazole-1-yl-ethoxy)-3,4-dihydro-2H-naphthalen-1-one

Step 1: 6-(β-Chloroethoxy)-1-tetralone

To a solution of 6-hydroxy tetralone (2.0 g, 12.3 mmol) in DMF (50 mL) was added dry cesium carbonate (8.02 g, 24.6 mmol). Neat 2-chloroethyl-p-toluensulfonate (3.49 g, 14.9 mmol) was added to this mixture and the reaction stirred at room temperature for 58 hours. The reaction was poured into 200 mL of water and to this mixture was added 10 mL of 1N NaOH followed by 200 mL of Et$_2$O. The mixture stirred at room temperature for 2 hours. The aqueous portion was separated and extracted with Et$_2$O (3×200 mL). The combined organic portions were washed successively with 1N NaOH (2×100 mL), water (2×100 mL), and brine, dried, filtered, and concentrated under vacuum to give 5.07 g of a faintly orange solid. The solid was dissolved in minimal DCM and chromatographed (silica gel, 190 g, DCM). The appropriate fractions were pooled and concentrated under vacuum to afford 2.65 g (96%) of a white crystalline solid:

$^1$H-NMR (CDCl$_3$): δ7.97 (1H, d, J=8.8 Hz), 6.79 (1H, dd, J=8.8 Hz, J=2.4 Hz), 6.69 (1H, br s), 4.26–4.23 (2H, m), 3.80–3.78 (2H, m), 2.88 (2H, t, J=6 Hz), 2.57 (2H, t, J=6 Hz), 2.11–2.05 (2H, m).

Step 2: 6-(2-Imidazole-1-yl-ethoxy)-3,4-dihydro-2H-naphthalen-1-one

A suspension of NaH (0.29 g, 7.2 mmol, 60% oil dispersion prewashed with dry hexanes) in 18 mL of dry DMF under a nitrogen flow was cooled to 0° C. and imidazole (0.49 g, 7.2 mmol) was added portionwise. The ice bath was removed and the reaction stirred at room temperature 20 minutes. The reaction was cooled to 0° C. and a solution of 6-(β-chloroethoxy)-1-tetralone (1.07 g, 4.8 mmol) in 12 mL of dry DMF was added over several minutes. The ice bath was removed and the reaction stirred at room temperature overnight. The reaction was partitioned between 20 mL of water and 200 mL of EtOAc. The organic portion was removed, and the aqueous portion was extracted with EtOAc (5×50 mL). The combined extracts were washed successively with water and brine, dried, filtered, and concentrated under vacuum to afford 1.6 g of crude product. Purification by flash chromatography (silica gel, 130 g, 8% MeOH in DCM) afforded 0.83 g (67%) of an off-white crystalline solid: CI-MS m/e 256 (M$^+$), 257 (M$^+$+1);

$^1$H-NMR (CDCl$_3$): δ7.96 (1H, dd, J=8.5 Hz, J=3.0 Hz), 7.61 (1H, s), 7.05 (1H, s), 7.00 (1H, s), 6.75 (1H, dd, J=8.8 Hz, J=3.0 Hz), 6.63 (1H, d, J=3.0 Hz), 4.34 (2K m), 4.23 (2H, m), 2.87 (2H, t, J=6.0 Hz), 2.57 (2H, t, J=6.0 Hz), 2.07 (2H, m).

EXAMPLE 2

6-[2-(2-Methyl-imidazole-1-yl)-ethoxy]-3,4-dihydro-2H-naphthalen-1-one

According to the method of Example 1, Step 2, 6-(β-chloroethoxy)-1-tetralone (0.208 g, 0.93 mmol) and 2-methylimidazole (0.137 g, 1.67 mmol) were reacted to provide the title compound (0.166 g, 66%) as a cream colored solid: CI-MS m/e 270 (M$^+$), 271 (M$^+$+1);

$^1$H-NMR (CDCl$_3$): δ7.94 (1H, d, J=8.0 Hz), 6.88 (2H, s), 6.72 (1H, dd, J=8.0 Hz, J=2.0 Hz), 6.60 (1H, d, J=2 Hz), 4.21 (4H, m), 2.85 (2H, t, J=6.0 Hz), 2.55 (2H, t, 3=6.0 Hz), 2.41 (3H, s), 2.05 (2H, m).

EXAMPLE 3

6-(2-Imidazole-1-yl-ethoxy)-2-pyridin-2-ylmethylene-3,4-dihydro-2H-naphthalen-1-one 2-Pyridine carboxaldehyde (0.202 g, 1.9 mmol) was added to a mixture of 6-(2-imidazole-1-yl-ethoxy)-3,4-dihydro-2H-naphthalen-1-one (1) (0.322 g, 1.2 mmol) in piperidine:acetic acid (30 μL:24 μL). The reaction mixture was heated in a 130° C. oil bath with efficient stirring for 1.5 hours. After cooling to room temperature, 2 mL of 1N HCl was added and the mixture stirred overnight. The mixture was made neutral with the addition of a saturated solution of NaHCO$_3$ and then extracted into DCM (3×50 mL). The pooled extracts were washed sequentially several times with water, then brine, dried, filtered, and concentrated in vacuo to leave a dark brown oil. Purification by flash chromatography (silica gel, 135 g, 7% MeOH in DCM) afforded 0.075 g of the title compound as a light tan solid.

EXAMPLE 4

6-(2-Imidazole-1-yl-ethoxy-2-(4-methylsulfanyl-benzylidene)-3,4-dihydro-2H-naphthalen-1-one 4-(Methylthio)benzaldehyde (0.114 g, 0.75 mmol) was added to a stirring solution of (1) (0.25 g, 0.98 mmol) in 2 mL 4% KOH in EtOH (wt/vol). The reaction stirred at room temperature for 2 hours and the resulting precipitate was collected and washed well with water and then cold iPrOH. The solid was dried in vacuo at 40° C. for 3 hours affording the title compound, 0.277 g (95%) as an off-white solid, mp 161–161.5° C.; CI-MS m/e 390 (M$^+$), 391 M$^+$+1);

$^1$H-NMR (CDCl$_3$): δ8.06 (1H, d, J=8.6 Hz), 7.75 (1H, s), 7.56 (1H, s), 7.33 (2H, d, J=8.3 Hz, Ph), 7.23 (2H, d, J=8.3 Hz, Ph), 7.05 (1H, s), 7.00 (1H, s), 6.81 (1H, dd, J=8.6 Hz, J=2.5 Hz) 6.64 (1H, d, J=2.5 Hz), 4.34 (2H, m), 4.25 (2H, m), 3.06 (2H, m), 2.86 (2H, m), 2.48 (3H, s). Elemental Analysis (C$_{23}$H$_{22}$S$_1$N$_2$O$_2$): Calculated: C, 70.74; H, 5.68; N, 7.17. Found: C, 70.36; H, 5.64; N, 7.11.

EXAMPLE 5

2-(4-Bromo-benzylidene)-6-(2-imidazole-1-yl-ethoxy)-3,4-dihydro-2H-naphthalen-1-one According to the method of Example 4, 6-(2-imidazole-1-yl-ethoxy)-3,4-dihydro-2H-naphthalen-1-one (0.40 g, 1.6 mmol) was reacted with 4-bromobenzaldehyde (0.433 g, 2.3 mmol) in 2 mL of 4% KOH in ethanol to afford 0.543 g (81%) of the title compound as a coarse white solid, mp 152–153° C.: CI-MS m/e 423, 425 (M⁺);

$^1$H-NMR (CDCl$_3$): δ8.06 (1H, d, J=8.5 Hz), 7.70 (1H, s), 7.56 (1H, s), 7.50 (2H, d, J=8.3 Hz, Ph), 7.24 (2H, d, J=8.3 Hz, Ph), 7.05 (1H, s), 7.00 (1H, s), 6.81 (1H, dd, J=2.4 Hz, J=8.5 Hz), 6.64 (1H, d, J=2.4 Hz), 4.34 (2H, m), 4.25 (2H, m), 3.02 (2H, m), 2.86 (2H, m). Elemental Analysis (C$_{22}$H$_{19}$N$_2$O$_2$Br)×0.22 H$_2$O: Calculated: C, 61.84; H, 4.59; N, 6.56. Found: C, 61.85; H, 4.53; N, 6.51.

EXAMPLE 6

6-(2-Imidazole-1-yl-ethoxy)-2-pyridin-4-ylmethylene-3,4-dihydro-2H-naphthalen-1-one 6-(2-Imidazole-1-yl-ethoxy)-3,4-dihydro-2H-naphthalen-1-one (0.50 g, 1.95 mmol) was reacted with 4-pyridinecarboxaldehyde (0.248 g, 2.3 mmol) in 2.5 mL of 4% KOH for 8 hours at room temperature. The reaction was diluted with water, the resulting mixture was filtered, and the filtrate was extracted into EtOAc. The combined extracts were evaporated to dryness, and the resulting yellow solid was purified twice by flash chromatography (silica gel, 120 g, 9% MeOH in DCM) to afford 0.146 g of a yellow oil which crystallized on standing. Recrystallization from minimal iPrOH afforded the title compound as a light yellow powder (0.041 g, 6%), mp 128.5–129° C., CI-MS m/e 345 (M⁺), 346 M⁺+1);

$^1$H-NMR (CDCl$_3$): δ8.62 (2H, d, J=6.1 Hz), 8.08 (1H, d, J=8.5 Hz), 7.66 (1H, s), 7.56 (1H, s), 7.24 (2H, d, J=6.1 Hz), 7.05 (1H, s), 7.00 (1H, s), 6.83 (1H, dd J=2.5 Hz, J=8.5 Hz), 6.65 (1H, d, J=2.5 Hz), 4.34 (2H, m), 4.26 (2H, m), 3.02 (2H, m), 2.88 (2H, m). Elemental Analysis (C$_{21}$H$_{19}$N$_3$O$_2$): Calculated: C, 72.11; H, 5.30; N, 12.02. Found: C, 71.95; H, 5.08; N, 11.91.

EXAMPLE 7

6-(2-Imidazole-1-yl-ethoxy)-2-(4-nitro-benzylidene)-3,4-dihydro-2H-naphthalen-1-one According to the method of Example 4, 6-(2-imidazole-1-yl-ethoxy)-3,4-dihydro-2H-naphthalen-1-one (0.19 g, 0.74 mmol) was reacted with 4-nitrobenzaldehyde (0.112 g, 0.74 mmol) in 1.5 mL of 4% KOH in ethanol for 3 hours at room temperature to afford 0.195 g (68%) of the title compound as a fine tan powder, mp 184–185° C.: CI-MS m/e 389 (M⁺), 390 M⁺+1);

$^1$H-NMR (CDCl$_3$): δ8.23 (2H, d, J=8.8 Hz, Ph), 8.08 (1H, d, J=8.8 Hz), 7.79 (1H, s), 7.78 (1H, s), 7.51 (2 d, J=8.8 Hz, Ph), 7.08 (1H, s), 7.04 (1H, s), 6.83 (1H, dd, J=8.8 Hz, J=2.4 Hz), 6.66 (1H, d, J=2.4 Hz), 4.39 (2H, m), 4.28 (2H, m), 3.03 (2H, m), 2.89 (2H, m). Elemental Analysis (C$_{22}$H$_{19}$N$_3$O$_4$): Calculated: C, 67.86; H, 4.92; N, 10.79. Found: C, 67.33; H, 4.60; N, 10.43.

EXAMPLE 8

2-[4-(2-Diethylamino-ethoxy)-benzylidene]-6-(2-imidazole-1-yl-ethoxy)-3,4-dihydro-2H-naphthalen-1-one 6-(2-Imidazole-1-yl-ethoxy)-3,4-dihydro-2H-naphthalen-1-one (0.505 g, 1.97 mmol) was reacted with 4-(diethylamino)ethoxy benzaldehyde (0.662 g, 3.0 mmol) in 2.5 mL of 4% KOH for 20 hours at room temperature. The reaction was diluted with brine, and the resulting mixture was extracted into DCM. The combined extracts were dried, filtered, and evaporated to dryness. The resulting oil was purified twice by flash chromatography (silica gel, 150 g, 10% MeOH in DCM) to afford 0.274 g (30%) of the title compound as a yellow oil: CI-MS m/e 459 (M⁺), 460 M⁺+1);

$^1$H-NMR (CDCl$_3$): δ8.05 (1H, d, J=8.7 Hz), 7.76 (1H, s), 7.56 (1H, s), 7.35 (2H, d, J=8.6 Hz, Ph), 7.04 (1H, s), 7.00 (1H, s), 6.90 (2H, d, J=8.6 Hz, Ph), 6.80 (1H, dd, J=8.7 Hz, J=2.4 Hz), 6.64 (1H, d, J=2.4 Hz), 4.33 (2H, t, J=6.1 Hz), 4.25 (2H, t, J=6.1 Hz), 4.06 (2H, t, J=6.4 Hz), 3.07 (2H, m), 2.88–2.83 (4H, m), 2.61 (4H, q, J=7.1 Hz), 1.05 (6H, t, J=7.1 Hz). Elemental Analysis (C$_{28}$H$_{33}$N$_3$O$_3$)×1.0 H$_2$O: Calculated: C, 70.41; H, 7.39; N, 8.80. Found: C, 70.54; H, 7.05; N, 8.61.

EXAMPLE 9

2-Benzylidene-6-(2-imidazole-1-yl-ethoxy)-3,4-dihydro-2H-naphthalen-1-one

According to the method of Example 8, 6-(2-imidazole-1-yl-ethoxy)-3,4-dihydro-2H-naphthalen-1-one (0.505 g, 1.97 mmol) was reacted with benzaldehyde (0.312 g, 2.94 mmol) in 3.0 mL of 4% KOH in EtOH overnight at room temperature to afford 0.596 g (88%) of the title compound as a cream-colored solid: CI-MS m/e 344 (M⁺), 345 M⁺+1);

$^1$H-NMR (CDCl$_3$): δ8.07 (1H, d, J=8.7 Hz), 7.80 (1H, s), 7.56 (1H, s), 7,39–7.31 (5H, m), 7.04 (1H, s), 7.00 (1H, s), 6.81 (1H, br d, J=8.7 Hz), 6.64 (1H, br s), 4.33 (2H, t, J=4.9 Hz), 4.25 (2H, t, J=4.9 Hz), 3.07 (2H, t, J=6 Hz), 2.86 (2H, t, J=6 Hz). Elemental Analysis (C$_{22}$H$_{20}$N$_2$O$_2$): Calculated: C, 76.72; H, 5.85; N, 8.13. Found: C, 70.54; H, 6.01; N, 7.95.

EXAMPLE 10

6-(2-Imidazole-1yl-ethoxy)-2-(4-methylsulfanyl-benzyl)-3,4-dihydro-2H-naphthalen-1-one Potassium tri-sec-butylborohydride, 1.0 M in THF (0.64 mL) was added to a solution of Compound (4) (0.250 g, 0.64 mmol) in 4.0 mL of dry THF at −78° C. under a nitrogen atmosphere. After 2 hours, the cooling bath was replaced with an ice bath and the reaction warmed to 0° C. at which time 10% NaOH (7.0 mL) and 30% H$_2$O$_2$ (5.0 mL) were added. The ice bath was permitted to melt. The reaction was diluted with water and extracted into DCM. The pooled organics were washed with water and brine, dried, filtered, and concentrated under vacuum. The resulting oil was purified by flash chromatography (silica gel, 56 g, 8% MeOH in DCM) to afford 0.100 g of a faintly yellow solid. Recrystallization of the solid from iPrOH afforded 0.026 g (10%) of the title compound as granular, cream-colored crystals, mp 114–117° C.: CI-MS m/e 392 (M⁺), 393 M⁺+1);

$^1$H-NMR (CDCl$_3$): δ7.99 (1H, d, J=8.4 Hz), 7.55 (1H, br s), 7.13 (4H, AB q, J=8.1 Hz, J=24.2 Hz), 7.04 (1H, br s), 6.99 (1H, br s), 6.76 (1H, br d, J=8.4 Hz), 6.59 (1H, br s), 4.32 (2H, m), 4.21 (2H, m), 3.38 (1H, br m), 2.65–2.53 (2H, m), 2.43 (3H, s), 2.04–2.00 (1H, m), 1.82–1.65 (1H, br m). Elemental Analysis (C$_{23}$H$_{24}$N$_2$SO$_2$)×0.24 H$_2$O×0.08 iPrOH: Calculated: C, 69.50; H, 6.30; N, 6.97. Found: C, 69.50; H, 6.15; N, 6.66.

EXAMPLE 11

6-(2-Imidazole-1yl-ethoxy)-2-thiophen-3-ylmethylene-3,4-dihydro-2H-naphthalen-1-one According to the method of Example 8, 6-(2-imidazole-1-yl-ethoxy)-3,4-dihydro-2H-naphthalen-1-one (0.250 g, 0.98 mmol) was reacted with 3-thiophene carboxaldehyde (0.166 g, 1.48 mmol) in 5.0 mL of 4% KOH in EtOH at room temperature to afford 0.265 g (77%) of the title compound as a cream-colored solid, mp 61–62° C.: CI-MS m/e 350 (M$^+$), 351 M$^+$+1);

$^1$H-NMR (CDCl$_3$): δ8.04 (1H, d, J=8.6 Hz), 7.77 (1H, s), 7.56 (1H, s), 7.45 (1H, m), 7.33 (1H, m), 7.24 (1H, m), 7.04 (1H, s), 7.00 (1H, s), 7.80 (1H, dd J=8.6 Hz, J=2.4 Hz), 6.64 (1H, d, J=2.4 Hz), 4.33 (2H, m), 4.24 (2H, m), 3.10 (2H, m), 2.89 (2H, m). Elemental Analysis (C$_{20}$H$_{18}$N$_2$SO$_2$)×0.5 H$_2$O: Calculated: C, 66.83; H, 5.33; N, 7.80. Found: C, 67.04; H, 4.94; N, 7.56.

EXAMPLE 12

4-[6-(2-Imidazole-1-yl-ethoxy)-1-oxo-3,4-dihydro-1H-naphthalen-2-ylidenemethyl]-benzoic acid 6-(2-Imidazole-1-yl-ethoxy)-3,4-dihydro-2H-naphthalen-1-one (0.400 g, 1.56 mmol) was reacted with 4-formyl benzoic acid (0.351 g, 2.34 mmol) in 5.0 mL of 4% KOH in EtOH and 1 mL of dioxane at room temperature for 6 days. The reaction was diluted with minimal water to achieve complete solution and then extracted with DCM. The resulting aqueous solution was acidified to pH 2 with 1N HCl. After standing at room temperature for 3 weeks, 0.061 g (10%) of the title compound was isolated by filtration as a fine cream powder, mp 267–267.5° C.: CI-MS m/e 388 (M$^+$), 389 M$^+$+1);

$^1$H-NMR (CDCl$_3$): δ7.94 (2H, d, J=8.3 Hz, Ph), 7.87 (1H, d, J=8.5 Hz), 7.64 (1H, br s), 7.62 (1H, br s), 7.56 (2H, d, J=8.3 Hz, Ph), 7.20 (1H, br s), 6.91 (1H, dd, J=2.4 Hz, J=8.5 Hz), 6.87 (1H, d, J=2.4 Hz), 6.84 (1H, s), 4.34–4.30 (4H, m), 3.00 (2H, m), 2.85 (2H, m). Elemental Analysis (C$_{20}$H$_{18}$N$_2$SO$_2$)×0.25 H$_2$O: Calculated: C, 70.31; H, 5.26; N, 7.13. Found: C, 70.14; H, 5.01; N, 6.91.

EXAMPLE 13

2-(4-Bromo-benzyl)-6-(2-imidazole-1-yl-ethoxy)-3,4-dihydro-2H-naphthalen-1-one To a mixture of dry sodium iodide (0.146 g, 0.97 mmol) and Compound 5 (0.200 g, 0.47 mmol) in AcCN 2.0 mL of dry at room temperature was added tetra-chlorosilane (0.11 mL, 0.97 mmol). After stirring for 5 hours at room temperature, the reaction was diluted with water and extracted into CHCl$_3$. The pooled extracts were decolorized by washing with a 10% solution of sodium thiosulfate. The resulting solution was washed with water, dried, filtered, and concentrated to afford 0.230 g of crude product which contained the title compound and its enolized tautomer (as observed by $^1$H-NMR). Purification by flash chromatography (silica gel, 40 g, 8% MeOH in DCM) afforded 0.066 g (33%) of the title compound as a dark peach solid, mp 129–130.5° C.: CI-MS m/e 424/426 (M$^+$), 425/427M$^+$+1).

Elemental Analysis (C$_{22}$H$_{21}$N$_2$BrO$_2$): Calculated: C, 62.13; H, 4.98; N, 6.59. Found: C, 61.87; H, 4.71; N, 6.39.

EXAMPLE 14

6-(2-Imidazole-1-yl-ethoxy)-2-thiophen-2-ylmethylene-3,4-dihydro-2H-naphthalen-1-one According to the method of Example 8, 6-(2-imidazole-1-yl-ethoxy)-3,4-dihydro-2H-naphthalen-1-one (0.400 g, 1.56 mmol) was reacted with 2-thiophene carboxaldehyde (0.264 g, 2.35 mmol) in 5.0 mL of 4% KOH in EtOH for 4.5 hours at room temperature to afford 0.369 g (67%) of the title compound as dark yellow crystals, mp 137–138° C.: CI-MS m/e 350 (M$^+$), 351 M$^+$+1);

$^1$H-NMR (CDCl$_3$): δ8.04 (1H, d, J=8.6 Hz), 7.98 (1H, s), 7.59 (1H, s), 7.47 (1H, d, J=4.9 Hz), 7.34 (1H, d, J=3.4 Hz), 7.10 (1H, m), 7.05 (1H, s), 7.01 (1H, s), 6.80 (1H, dd, J=8.6 Hz, J=2.4 Hz), 6.67 (1H, br s), 4.34 (2H, m), 4.25 (2H, m), 3.15 (2H, m), 2.94 (2H, m). Elemental Analysis (C$_{20}$H$_{18}$N$_2$SO$_2$)×0.17 H$_2$O: Calculated: C, 67.95; H, 5.23; N, 7.93. Found: C, 67.95; H, 5.28; N, 7.77.

EXAMPLE 15

6-(2-Imidazole-1-yl-ethoxy)-2-naphthalen-1-ylmethylene-3,4-dihydro-2H-naphthalen-1-one According to the method of Example 6, 6-(2-imidazole-1-yl-ethoxy)-3,4-dihydro-2H-naphthalen-1-one (0.475 g, 1.85 mmol) was reacted with 1-naphthaldehyde (0.448 g, 2.87 mmol) in 3.0 mL of 4% KOH in EtOH for 6 hours at room temperature to afford 0.639 g (88%) of the title compound as a bright yellow solid, mp 147–148° C.: CI-MS m/e 494 (M$^+$), 495 M$^+$+1);

$^1$H-NMR (CDCl$_3$): δ8.30 (1H, s), 8.14 (1H, d, J=8.5 Hz), 7.98–7.95 (1H, m), 7.87–7.82 (2H, m), 7.58 (1H, br s), 7.50–7.44 (3H, m), 7.37 (1H, m), 7.05 (1H, s), 7.01 (1H, s), 6.84 (1H, dd, J=8.5 Hz, J=2.2 Hz), 6.64 (1H, s), 4.34 (2H, m), 4.26 (2H, m), 2.92 (2H, m), 2.83 (2H, m). Elemental Analysis (C$_{26}$H$_{22}$N$_2$O$_2$)×0.64 H$_2$O: Calculated: C, 76.92; H, 5.78; N, 6.90. Found: C, 76.92; H, 5.51; N, 6.75.

EXAMPLE 16

2-Furan-2-ylmethylene-6-(2-imidazole-1-yl-ethoxy)-3,4-dihydro-2H-naphthalen-1-one According to the method of Example 6, 6-(2-imidazole-1-yl-ethoxy)-3,4-dihydro-2H-naphthalen-1-one (0.250 g, 0.98 mmol) was reacted with 2-furaldehyde (0.151 g, 1.57 mmol) in 3.0 mL of 4% KOH in EtOH for 15 hours at room temperature to afford 0.220 g (67%) of the title compound as a light tan solid, mp 109–110° C.: CI-MS m/e 334 (M$^+$), 335 M$^+$+1);

$^1$H-NMR (CDCl$_3$): δ8.03 (1H, d, J=8.8 Hz), 7.57 (1H, s), 7.51 (2H, s), 7.04 (1H, s), 7.00 (1H, s), 6.80 (1H, dd, J=8.8 Hz, J=2.5 Hz), 6.68–6.64 (2H, m), 6.47 (1H, m), 4.33 (2H, m), 4.24 (2H, m), 3.27 (2H, m), 2.91 (2H, m). Elemental Analysis (C$_{20}$H$_{18}$N$_2$O$_3$)×0.2 H$_2$O: Calculated: C, 71.07; H, 5.49; N, 8.29. Found: C, 71.13; H, 5.71; N, 8.13.

EXAMPLE 17

2-(4-Bromo-thiophen-2-ylmethylene)-6-(2-imidazole-1-yl-ethoxy)-3,4-dihydro-2H-naphthalen-1-one According to the method of Example 4, 6-(2-imidazole-1-yl-ethoxy)-3,4-dihydro-2H-naphthalen-1-one (0.252 g, 0.98 mmol) was reacted with 4-bromothiophene-2-carboxaldehyde (0.282 g, 1.5 mmol) in 5 mL of 4% KOH in EtOH to afford 0.181 g (43%) of the title compound as a light tan powder, mp 164–166° C.: CI-MS m/e 428, 430 (M$^+$); 429, 431 M$^+$+1);

$^1$H-NMR (CDCl$_3$): δ8.03 (1H, d, J=8.8 Hz), 7.82 (1H, s), 7.58 (1H, s), 7.33 (1H, s), 7.20 (1H, s), 7.05 (1H, s), 7.01 (1H, s), 6.80 (1H, dd, J=8.8 Hz, J=2.4 Hz), 6.66 (1H, d, J=2.2 Hz), 4.34 (2H, m), 4.25 (2H, m), 3.10 (2H, m), 2.93 (2H, m). Elemental Analysis (C$_{20}$H$_{17}$BrN$_2$SO$_2$)×0.61 H$_2$O: Calculated: C, 54.55; H, 4.17; N, 6.36. Found: C, 54.55; H, 4.07; N, 6.34.

EXAMPLE 18

2-(5-Chloro-thiophen-2-ylmethylene)-6-(2-imidazole-1-yl-ethoxy)-3,4-dihydro-2H-naphthalen-1-one According to the method of Example 4, 6-(2-imidazole-1-yl-ethoxy)-3,4-dihydro-2H-naphthalen-1-one (0.25 g, 0.98 mmol) was reacted with 5-chlorothiophene-2-carboxaldehyde (0.215 g, 1.47 mmol) in 5 mL of 4% KOH in EtOH to afford 0.293 g (77%) of the title compound as a coarse cream solid, mp 143–144° C.: APCI-MS m/e 385.5 M$^+$+1);
$^1$H-NMR (CDCl$_3$): δ8.03 (1H, d, J=8.5 Hz), 7.81 (1H, s), 7.65 (1H, s), 7.10 (1H, d, J=3.9 Hz), 7.06 (1H, s), 7.02 (1H, s), 6.91 (1H, d, J=3.9 Hz), 6.80 (1H, m), 3.05 (2H, m), 2.93 (2H, m). Elemental Analysis (C$_{20}$H$_{17}$ClN$_2$SO$_2$)×0.14 H$_2$O× 0.02 iPrOH: Calculated: C, 62.00; H, 4.52; N, 7.21. Found: C, 62.00; H, 4.19; N, 7.03.

EXAMPLE 19

6-(2-Imidazole-1-yl-ethoxy)-2-(5-methylsulfanyl-thiophen-2-ylmethylene)-3,4-dihydro-2H-naphthalen-1-one According to the method of Example 4, 6-(2-imidazole-1-yl-ethoxy)-3,4-dihydro-2H-naphthalen-1-one (0.25 g, 0.98 mmol) was reacted with 5-(methylthio)thiophene-2-carboxaldehyde (0.233 g, 1.47 mmol) in 4 mL of 4% KOH in EtOH for 2 hours at room temperature to afford 0.293 g (36%) of the title compound as a dark yellow powder, mp 102–104° C.: APCI-MS m/e 397.5 M$^+$+1).
Elemental Analysis (C$_{21}$H$_{20}$N$_2$S$_2$O$_2$)×0.65 H$_2$O×0.12 EtOH: Calculated: C, 61.66; H, 5.36; N, 6.77. Found: C, 61.66; H, 5.00; N, 6.71.

EXAMPLE 20

6-(2-Imidazole-1-yl-ethoxy)-2-(3-phenoxy-thiophen-2-ylmethylene)-3,4-dihydro-2H-naphthalen-1-one According to the method of Example 4, 6-(2-imidazole-1-yl-ethoxy)-3,4-dihydro-2H-naphthalen-1-one (0.25 g, 0.98 mmol) was reacted with 3-phenoxythiophene-2-carboxaldehyde (0.300 g, 1.47 mmol) in 4 mL of 4% KOH in EtOH for 3 hours at room temperature to afford 0.331 g (76%) of the title compound as an off-white solid, mp 135–137° C.: APCI-MS m/e 443.5 M$^+$+1).
Elemental Analysis (C$_{26}$H$_{22}$N$_2$SO$_3$)×0.21 H$_2$O: Calculated: C, 69.97; H, 5.06; N, 6.28. Found: C, 69.96; H, 4.68; N, 6.03.

EXAMPLE 21

2-[2,2']Bithiophenyl-5-ylmethylene-6-(2-imidazole-1-yl-ethoxy)-3,4-dihydro-2H-naphthalen-1-one According to the method of Example 4, 6-(2-imidazole-1-yl-ethoxy)-3,4-dihydro-2H-naphthalen-1-one (0.200 g, 0.78 mmol) was reacted with 2,2'-bisthiophene-5-carboxaldehyde (0.233 g, 1.2 mmol) in 4 mL of 4% KOH in EtOH at room temperature overnight to afford 0.284 g (84%) of the title compound as a yellow solid, mp 180–181° C.: APCI-MS mi/e 433.4 M$^+$+1).
Elemental Analysis (C$_{24}$H$_{20}$N$_2$O$_2$S$_2$)×0.40 H$_2$O: Calculated: C, 65.55; H, 4.77; N, 6.37. Found: C, 65.55; H, 4.65; N, 6.19.

EXAMPLE 22

6-(2-Imidazole-1-yl-ethoxy)-2-(5-nitro-thiophen-2-ylmethylene)-3,4-dihydro-2H-naphthalen-1-one 6-(2-Imidazole-1-yl-ethoxy)-3,4-dihydro-2H-naphthalen-1-one (0.200 g, 0.78 mmol) was reacted with 5-nitrothiophene-2-carboxaldehyde (0.123 g, 0.78 mmol) in a mixture of HOAc (1 mL) and concentrated H$_2$SO$_4$ (0.100 mL) at room temperature overnight. The reaction was diluted with water, and the resulting precipitate was collected, washed well with water, and dried in vacuo at 60° C. to afford 0.296 g (80%) of the title compound as a brown powder, mp >240° C.: APCI-MS m/e 396.1 M$^+$+1).
Elemental Analysis (C$_{20}$H$_{17}$N$_3$SO$_4$)×1.39 H$_2$O×0.53 H$_2$SO$_4$: Calculated: C, 50.84; H, 4.45; N, 8.89; S, 10.38. Found: C, 50.84; H, 4.39; N, 8.82; S, 10.37.

EXAMPLE 23

2-Furan-3-ylmethylene-6-(2-imidazole-1-yl-ethoxy)-3,4-dihydro-2H-naphthalen-1-one According to the method of Example 8, 6-(2-imidazole-1-yl-ethoxy)-3,4-dihydro-2H-naphthalen-1-one (0.20 g, 0.78 mmol) was reacted with 3-furaldehyde (0.083 g, 0.86 mmol) in 2 mL of 4% KOH in EtOH for 48 hours at room temperature to afford 0.182 g (70%) of the title compound, mp 116–117° C.: APCI-MS m/e 335.3 M$^+$+1).
Analysis Calculated for (C$_{20}$H$_{18}$N$_2$O$_3$)×0.27 H$_2$O: C, 70.81; H, 5.51; N, 8.26. Found: C, 70.78; H, 5.42; N, 8.14.

EXAMPLE 24

6-(2-Imidazole-1-yl-ethoxy)-2-(4-methoxy-benzylidene)-3,4-dihydro-2H-naphthalen-1-one According to the method of Example 4, 6-(2-imidazole-1-yl-ethoxy)-3,4-dihydro-2H-naphthalen-1-one (0.200 g, 0.78 mmol) was reacted with p-anisaldehyde (0.117 g, 0.87 mmol) in 2 mL of 4% KOH in EtOH at room temperature overnight to afford 0.248 g (84%) of the title compound, mp 132–133° C.: APCI-MS m/e 375 M$^+$+1).
Elemental Analysis (C$_{23}$H$_{22}$N$_2$O$_3$)×0.18 H$_2$O: Calculated: C, 73.14; H, 5.97; N, 7.42. Found: C, 73.14; H, 5.88; N, 7.30.

EXAMPLE 25

6-(2-Imidazol-1-yl-ethoxy)-2-(2-methoxy-benzylidene)-3,4-dihydro-2H-naphthalen-1-one 6-(2-Imidazole-1-yl-ethoxy)-3,4-dihydro-2H-naphthalen-1-one (0.200 g, 0.78 mmol) was reacted with o-anisaldehyde (0.117 g, 0.87 mmol) in 2 mL of 4% KOH in EtOH at room temperature overnight. The reaction was diluted with water to induce the precipitation of a red gum. The aqueous layer was decanted, and the remaining residue was concentrated several times from EtOH and then chromatographed (SiO$_2$, 30 g, 8% MeOH in DCM) to afford 0.249 g (84%) of the title compound as a yellow foam: APCI-MS m/e 375.3 M$^+$+1).
Elemental Analysis (C$_{23}$H$_{22}$N$_2$O$_3$)×0.47 H$_2$O. Calculated: C, 72.15; H, 6.04; N, 7.32. Found: C, 72.16; H, 5.77; N, 7.17.

EXAMPLE 26

6-(2-Imidazole-1-yl-ethoxy)-2-thiazol-2-ylmethylene-3,4-dihydro-2H-naphthalen-1-one Step 1: 2-(Hydroxy-thiazol-2-yl-methyl)-6-(2-imidazole-1-yl-ethoxy)-3,4-dihydro-2H-naphthalen-1-one 6-(2-Imidazole-1-yl-ethoxy)-3,4-dihydro-2H-naphthalen-1-one (0.200 g, 0.78 mmol) was reacted with 2-formylthiazole (0.107 g, 0.94 mmol) in a mixture of HOAc (1 mL) and concentrated $H_2SO_4$ (0.100 mL) at room temperature overnight. The resulting biphasic reaction mixture was diluted with water and then extracted with EtOAc. The aqueous portion was made to pH 10 with 50% NaOH and extracted with EtOAc (3×50 mL). The pooled organic extracts were washed well with water, dried, filtered, and concentrated to afford 0.215 g (74%) of the title compound as a golden oil: APCI-MS m/e 370.2 M$^+$+1).

Step 2: 6-(2-Imidazole-1-yl-ethoxy)-2-thiazol-2-ylmethylene-3,4-dihydro-2H-naphthalen-1-one Conversion of the product from Step 1 to the title compound is achieved by treatment with trifluoroacetic anhydride.

EXAMPLE 27

6-[2-(1H-Imidazole4-yl)-ethoxy]-3,4-dihydro-2H-naphthalen-1-one, monohydrochloride 6-Hydroxytetralone (1.46 g, 9.01 mmol) was dissolved in a mixture of 15 mL AcCN and 8 mL DMF, and solid potassium carbonate (4.98 g, 36 mmol) was added followed by a solution of 4-(2-bromoethyl)-1H-imidazole hydrobromide (2.05 g, 8.01 mmol) in a mixture of 15 mL AcCN and 3 mL DMF. After stirring for 24 hours at room temperature, the reaction was concentrated in vacuo to remove the solvents, and the resulting residue was diluted with water and extracted into EtOAc. The pooled organics were washed sequentially with a saturated solution of $NaHCO_3$, water, and brine and concentrated in vacuo to afford 1.57 g of crude product. Purification by flash chromatography (silica gel, 235 g, 5% MeOH in DCM) gave a yellow oil. The oil was taken up in 7 mL DCM, and the product was precipitated as a salt by the addition of 1.5 mL of 8N HCl in iPrOH. The solid was collected, washed with iPrOH, triterated with $Et_2O$, and dried in vacuo to afford 0.826 g (33%) of the title compound;

$^1$H-NMR (DMSO-d$_6$): δ8.97 (1H, d, J=1 Hz), 7.75 (1H, m), 7.46 (1H, d, J=1 Hz), 6.85 (2H, m), 4.28 (2H, m), 3.08 (2H, m), 2.84 (2H, m), 2.46 (2H, m), 1.94 (2H, m). Elemental Analysis ($C_{15}H_{16}N_2O_2$)×1.0 HCl×1.22 $H_2O$: Calculated: C, 57.31; H, 6.23; N, 8.91; Cl, 11.16. Found: C, 57.27; H, 6.14; N, 8.88; Cl, 11.41.

EXAMPLE 28

6-[2-(1H-Imidazole-4-yl)-ethoxy]-2-thiophen-3-ylmethylene-3,4-dihydro-2H-naphthalen-1-one According to the method of Example 32, Step 2, 4-[2-(5-oxo-5,6,7,8-tetrahydro-naphthalen-2-yloxy)-ethyl]-imidazole-1-carboxylic acid tert-butyl ester (0.270 g, 0.76 mmol) was reacted with thiophene-3-carboxaldehyde (0.128 g, 1.14 mmol) in 5 mL of 4% KOH in EtOH for 22 hours to afford, after chromatography (silica gel, 50 g; 8% MeOH in DCM), 0.167 g (59%) of the title compound as a dull yellow powder, mp 94–96° C.: CI-MS m/e 351 (M$^+$+1).

Elemental Analysis ($C_{20}H_{18}N_2SO_2$)×0.29 DCM×0.21 $H_2O$: Calculated: C, 64.33; H, 5.06; N, 7.39. Found: C, 64.41; H, 5.09; N, 7.11.

EXAMPLE 29

6-[2-(1H-Imidazole-4-yl)-ethoxy]-2-thiophen-2-ylmethylene-3,4-dihydro-2H-naphthalen-1-one According to the method of Example 32, Step 2, 4-[2-(5-oxo-5,6,7,8-tetrahydro-naphthalen-2-yloxy)-ethyl]-imidazole-1-carboxylic acid tert-butyl ester (0.356,g, 1.0 mmol) was reacted with thiophene-2-carboxaldehyde (0.174 g, 1.55 mmol) in 5 mL of 4% KOH in EtOH for 24 hours to afford, after chromatography (silica gel, 60 g; 8% MeOH in DCM), 0.154 g (40%) of the title compound as a red glassy solid, mp 60–63° C.: CI-MS m/e 351 (M$^+$+1).

Elemental Analysis ($C_{20}H_{18}N_2SO_2$)×0.45 DCM×0.06 $H_2O$: Calculated: C, 63.02; H, 4.92; N, 7.19. Found: C, 63.01; H, 4.91; N, 7.03.

EXAMPLE 30

2-Benzylidene-6-[2-(1H-imidazole-4-yl)-ethoxy]-3,4-dihydro-2H-naphthalen-1-one

Step 1: 4-[2-(5-Oxo-5,6.7.8-tetrahydro-naphthalen-2-yloxy)-ethyl]-imidazole-1-carboxylic acid tert-butyl ester A solution of 1-N-Boc-4-(2-hydroxyethyl)imidazole (1.06 g, 5.0 mmol), 6-hydroxytetralone (0.811 g, 5.0 mmol), and triphenylphosphine (1.44 g, 5.5 mmol) in 10 mL of freshly distilled THF was cooled in an ice bath for 10 minutes and then treated with neat diethyl azodicarboxylate (0.87 mL, 5.5 mmol) added via syringe through a rubber septum. The ice bath was permitted to melt and the reaction continued at room temperature for 5 hours. The solvent was removed in vacuo and the residue was chromatographed (silica gel, 500 g; 1:1, EtOAc:hexanes), and the pure fractions were pooled to afford 0.61 g (33%) of the title compound as a clear, colorless, viscous oil: CI-MS m/e 357 (M$^+$+1).

Step 2: 2-Benzylidene-6-[2-(1H-imidazole-4-yl)-ethoxy]-3,4-dihydro-2H-naphthalen-1-one According to the method of Example 6, the product of Step 1 (0.271 g, 0.76 mmol) was reacted with benzaldehyde (0.121 g, 1.14 mmol) in 5 mL of 4% KOH in EtOH for 3 hours at room temperature to afford 0.125 g (46%) of the title compound as a foam which solidified on standing to give a yellow solid, mp 53–56° C.: CI-MS m/e 345 (M$^+$+1).

Elemental Analysis ($C_{20}H_{24}N_2O_2$)×0.13 DCM: Calculated: C, 74.78; H, 5.75; N, 7.88. Found: C, 74.92; H, 5.62; N, 7.72.

EXAMPLE 31

6-[2-(1H-Imidazole-4-yl)-ethoxy]-2-(4-methylsulfanyl-benzylidene)-3,4-dihydro-2H-naphthalen-1-one 6-[2-(1H-Imidazole-4-yl)-ethoxy]-3,4-dihydro-2H-naphthalen-1-one (29) (0.18 g, 0.70 mmol) was dissolved in 5 mL of 4% KOH in EtOH (wt/vol) and treated with 4-(methylthio)benzaldehyde (0.172 g, 1.13 mmol). After stirring for 22 hours at room temperature, the reaction was diluted with water and extracted into EtOAc. The pooled organics were washed sequentially with water and brine, dried, filtered, and concentrated in vacuo to afford 0.39 g of crude product. Purification by flash chromatography (silica gel, 60 g, 8% MeOH in DCM) afforded 0.174 g (64%) of a bright yellow foam which solidified, mp 65–70° C.: CI-MS m/e 390 (M$^+$), 391 (M$^+$+1).

Elemental Analysis ($C_{23}H_{22}N_2O_2S$)×0.10 DCM: Calculated: C, 69.54; H. 5.61; N, 7.02. Found: C, 69.65; H, 5.42; N, 7.00.

EXAMPLE 32

6-[2-(1H-Imidazole-4-yl)-ethoxy]-2-(5-methylsulfanyl-thiophen-2-ylmethylene)-3,4-dihydro-2H-naphthalen-1-one, monohydrochloride According to the method of Example 33, 6-[2-(1H-imidazole-4-yl)-ethoxy]-3,4-dihydro-2H-naphthalen- -one, monohydrochloride (0.313 g, 1.07 mmol) was reacted with (5-methylthio)thiophene-2-carboxaldehyde (0.178 g, 1.13 mmol) in 5 mL of 4% KOH in EtOH overnight. After workup and purification, the product obtained from chromatography (silica gel, 10% MeOH in DCM) was taken up in minimal DCM and then precipitated upon the addition of 8N HCl in iPrOH. The solid was collected, washed with iPrOH, triterated with Et$_2$O, recrystallized from EtOH/Et$_2$O, and dried in vacuo to afford 0.262 g (52%), mp 168–169° C.: CI-MS m/e 397 (M$^+$+1).

Elemental Analysis (C$_{21}$H$_{20}$N$_2$O$_2$S$_2$)×1.03 HCl×2.13 H$_2$O: Calculated: C, 53.39; H, 5.40; N, 5.93; Cl, 7.73. Found: C, 53,43, H, 5.33; N, 5.81; Cl, 7.50.

EXAMPLE 33

4-{6-[2-(1H-Imidazole-4-yl)-ethoxy]-1-oxo-3,4-dihydro-1H-naphthalen-2-ylidenemethyl}-benzamide, monohydrochloride According to the method of Example 34, 6-[2-(1H-imidazole-4-yl)-ethoxy]-3,4-dihydro-2H-naphthalen-1-one, monohydrochloride (0.313 g, 1.07 mmol) was reacted with benzamide-4-carboxaldehyde (0.178 g, 1.13 mmol) in 5 mL of 4% KOH in EtOH overnight to afford 0.197 (42%) of the title compound as an off-white powder, mp dec. >230° C.: CI-MS m/e 388 (M$^+$+1).

Elemental Analysis (C$_{23}$H$_{21}$N$_3$O$_3$)×1.06 HCl×0.72 H$_2$O: Calculated: C, 62.92; H, 5.39; N, 9.57; Cl, 8.56. Found: C, 63.01; H, 5.18; N, 9.47; Cl, 8.44.

EXAMPLE 34

N,N-Diethyl-4-{6-[2-(1H-imidazole-4-yl)-ethoxy]-1-oxo-3,4-dihydro-1H-naphthalen-2-ylidenemethyl}-benzamide, monohydrochloride According to the method of Example 34, 6-[2-(1H-midazole-4-yl)-ethoxy]-3,4-dihydro-2H-naphthalen-1-one, monohydrochloride (0.313 g, 1.07 mmol) was reacted with N,N-diethylbenzamide-4-carboxaldehyde (0.231 g, 1.13 mmol) in 5 mL of 4% KOH in EtOH overnight to afford 0.277 (53%) of the title compound as a light yellow powder, mp 211–213° C.: CI-MS m/e 444 (M$^+$+1).

Elemental Analysis (C$_{27}$H$_{29}$N$_3$O$_3$)×0.97 HCl×0.68 H$_2$O: Calculated: C, 66.03; H, 6.43; N, 8.56; Cl, 7.00. Found: C, 66.00; H, 6.33; N, 8.47; Cl, 6.98.

EXAMPLE 35

4-{6-[2-(1H-Imidazole-4-yl)-ethoxy]-1-oxo-3,4-dihydro-1H-naphthalen-2-ylidenemethyl}-benzoic acid, ditrifluoroacetate According to the method of Example 34, 6-[2-(1H-imidazole-4-yl)-ethoxy]-3,4-dihydro-2H-naphthalen-1-one, monohydrochloride (0.313 g, 1.07 mmol) was reacted with 4-formyl benzoic acid, ethyl ester (0.200 g, 1.12 mmol) in 5 mL of 4% KOH in EtOH overnight, and the resulting solid was purified by preparative HPLC (C18, 0.1% TFA in H$_2$O: 0.1% TFA in AcCN; gradient 80:20 to 20:80) to afford 0.237 g (35%) of the title compound as a cream-colored powder, mp dec. 202–204° C.: APCI-MS m/e 389 (M$^+$+1).

EXAMPLE 36

2-(5-Chloro-thiophen-2-ylmethylene)-6-[2-(1H-imidazole-4-yl)-ethoxy]-3,4-dihydro-2H-naphthalen-1-one, hydrochloride According to the method of Example 34, 6-[2-(1H-imidazole-4-yl)-ethoxy]-3,4-dihydro-2H-naphthalen-1-one, monohydrochloride (0.313 g, 1.07 mmol) was reacted with 5-chloro-2-thiophene carboxaldehyde (0.165 g, 1.13 mmol) in 5 mL of 4% KOH in EtOH overnight to afford 0.272 g (60%) of the title compound as a dull yellow powder, mp dec. >210° C.: CI-MS m/e 385, 387 (M$^+$—Cl).

Elemental Analysis (C$_{20}$H$_{17}$N$_2$ClSO$_2$)×0.99 HCl×1.71 H$_2$O: Calculated: C, 53.17; H, 4.78; N, 6.20; Cl, 7.77. Found: C, 53.03; H, 4.47; N, 6.13; Cl, 7.82.

EXAMPLE 37

6-[2-(1H-Imidazole-4-yl)-ethoxy]-2-(5-methyl-thiophen-2-ylmethylene)-3,4-dihydro-2H-naphthalen-1-one According to the method of Example 34, 6-[2-(1H-imidazole-4-yl)-ethoxy]-3,4-dihydro-2H-naphthalen-1-one, monohydrochloride (0.313 g, 1.07 mmol) was reacted with 5-methyl-2-thiophene carboxaldehyde (0.142 g, 1.13 mmol) in 5 mL of 4% KOH in EtOH overnight to afford 0.207 g (44%) of the title compound as a bright orange solid, mp 69–70° C.: CI-MS m/e 364 (M$^+$), 365 (M$^+$+1).

Elemental Analysis (C$_{21}$H$_{20}$N$_2$SO$_2$)×1.0 HCl×2.11 H$_2$O: Calculated: C, 57.46; H, 5.79; N, 6.38; Cl, 8.08. Found: C, 57.24; H, 5.50; N, 6.18; Cl, 7.95.

EXAMPLE 38

5-{6-[2-(1H-Imidazol-4-yl)-ethoxy]-1-oxo-3,4-dihydro-1H-naphthalen-2-ylidenemethyl}-thiophene-2-carboxylic acid According to the method of Example 34, 6-[2-(1H-imidazole-4-yl)-ethoxy]-3,4-dihydro-2H-naphthalen-1-one, monohydrochloride (0.220 g, 0.75 mmol) was reacted with 5-carboxymethyl-2-thiophene carboxaldehyde (0.191 g, 1.12 mmol) in 5 mL of 4% KOH in EtOH overnight, and the resulting solid was purified by preparative HPLC (C18, 0.1% TFA in H$_2$O:0.1% TFA in AcCN; gradient 80:20 to 20:80) to afford 0.302 g (75%) of the title compound as a light tan powder, mp dec. >200° C.: APCI-MS m/e 395 (M$^+$+1).

Elemental Analysis (C$_{21}$H$_{18}$N$_2$SO$_4$)×1.0 TFA×1.46 H$_2$O: Calculated: C, 51.59; H, 4.12; N, 5.23; F, 10.74. Found: C, 51.80; H, 3.73; N, 5.26; F, 10.49.

EXAMPLE 39

6-[2-(1H-Imidazole-4-yl)-ethoxy]-2-(3-methyl-thiophen-2-ylmethylene)-3,4-dihydro-2H-naphthalen-1-one According to the method of Example 4, 6-[2-(1H-imidazole-4-yl)-ethoxy]-3,4-dihydro-2H-naphthalen-1-one, monohydrochloride (0.146 g, 0.50 mmol) was reacted with 3-methyl-thiophene-2-carboxaldehyde (0.095 g, 0.50 mmol) in 5 mL of 4% KOH in EtOH to afford 0.115 g (63%) of the title compound as a coarse cream powder, mp 191–193° C.: CI-MS m/e 365 (M$^+$).

EXAMPLE 40

6-[2-(1H-Imidazole-4-yl)-ethoxy]-2-(1-phenyl-ethylidene)-3,4-dihydro-2H-naphthalen-1-one Step 1: 1,6-Bis-trimethylsilanyloxy-3,4-dihyrdo-naphthalene To a solution of 6-hydroxytetralone (0.972 g, 6.0 mmol) in 10 mL of freshly distilled AcCN at room temperature was added sequentially dry NaI (2.25 g, 15 mmol), TEA (2.10 mL, 15 mmol), and chlorotrimethylsilane (1.92 mL, 15 mmol). After stirring for 1 hour, the reaction was quenched with the addition of a cold solution of saturated ammonium chloride and the reaction was extracted into $Et_2O$ (2×100 mL). The combined extracts were washed with ice cold water and then dried, filtered, and concentrated in vacuo to afford 1.53 g of the title compound as a colorless oil which was used for further reaction without purification.

Step 2: 6-Hydroxy-2-(1-phenyl-ethylidene)-3,4-dihydro-2H-naphthalen-1-one

Under a nitrogen atmosphere, a solution of the compound obtained from Step 1 and $SnCl_4$ (0.70 mL, 6 mmol) in 4 mL dry DCM was prepared in Flask A and stirred for 15 minutes at room temperature. Phenylacetylene (0.404 g, 4 mmol) and $Bu_3N$ (0.96 mL, 4 mmol) in dry AcCN was added to an AcCN (10 mL) solution of $SnCl_4$ (0.46 mL, 4.18 mmol) in Flask B, and the mixture was stirred for 10 minutes at room temperature. The contents of Flask A were transferred to Flask B. The reaction mixture was stirred at reflux for 1 hour and then poured over ice-cold saturated aqueous $NH_4Cl$. EtOAc was added, and the organic extract was separated and washed with 0.5N HCl. The organic portion was then poured into 0.5N KOH and filtered to remove a fine precipitate. The organic portion was separated from the filtrate, and the aqueous KOH portion was extracted with EtOAc. The pooled organic extracts were washed with 0.5N HCl then water, dried, filtered, and concentrated to leave 0.410 g of crude product. Chromatography ($SiO_2$, 60 g, 20% EtOAc in hexanes) afforded 0.186 g (12%) of the title compound as a crystalline solid, CI-MS m/e 265 ($M^++1$).

Step 3: 6-[2-(1H-Imidazole-4-yl)-ethoxy]-2-(1-phenyl-ethylidene)-3,4-dihydro-2H-naphthalen-1-one The product obtained from Step 2 (0.180 g, 0.68 mmol) was dissolved in 5 mL of dry DMF and treated with $K_2CO_3$ (0.376 g, 2.72 mmol) and 4-(2-bromoethyl)imidazole hydrobromide (0.192 g, 0.75 mmol). After stirring overnight at room temperature, the reaction was diluted with water and extracted with EtOAc. The pooled extracts were washed well with aqueous 0.5N KOH, water and brine, and then dried, filtered, and concentrated. Purification of the residue ($SiO_2$, 5% MeOH in DCM) afforded 0.120 g (49%) of the title compound as a light yellow foam. Conversion of this product to its HCl salt according to the method of Example 34 afforded 0.063 g of a light yellow powder, mp 170–172° C.: CI-MS m/e 359 ($M^++1$).

Elemental Analysis ($C_{23}H_{22}N_2O_2$)×0.25 $H_2O$×1.0 HCl: Calculated: C, 69.17; H. 5.93; N, 7.01. Found: C, 69.48; H, 6.03; N, 7.03.

EXAMPLE 41

2-Furan-2-ylmethylene-6-[2-(1H-imidazole-4-yl)-ethoxy]-3,4-dihydro-2H-naphthalen-1-one According to the method of Example 32, 4-[2-(5-oxo-5,6,7,8-tetrahydro-naphthalen-2-yloxy)-ethyl]-imidazole-1-carboxylic acid tert-butyl ester (0.270 g, 0.75 mmol) was reacted with 2-furylaldehyde (0.095 mL, 1.14 mmol) in 5 mL of 4% KOH in EtOH overnight to afford 0.190 g (76%) of the title compound as a foam which solidified on standing to give a dark red powder, mp 57–60° C.: CI-MS m/e 335 ($M^++1$).

Elemental Analysis ($C_{20}H_{18}N_2O_3$)×0.13 DCM: Calculated: C, 70.00; H, 5.33; N, 8.11. Found: C, 69.91; H, 5.27; N, 8.01.

EXAMPLE 42

2-(4-Bromo-benzylidene)-6-[2-(1H-imidazole-4-yl)-ethoxy]-3,4-dihydro-2H-naphthalen-1-one According to the method of Example 32, 4-[2-(5-oxo-5,6,7,8-tetrahydro-naphthalen-2-yloxy)-ethyl]-imidazole-1-carboxylic acid tert-butyl ester (0.278 g, 0.78 mmol) was reacted with p-bromobenzaldehyde (0.217 g, 1.17 mmol) in 5 mL of 4% KOH in EtOH overnight to afford 0.173 g (51%) of the title compound as a dark cream-colored powder, mp 176–178° C.: CI-MS m/e 423, 425 $M^++1$).

Elemental Analysis ($C_{22}H_{19}N_2O_2$)×0.16 DCM: Calculated: C, 60.92; H,L 4.46; N, 6.41. Found: C, 60.89; H, 4.33; N, 6.31.

EXAMPLE 43

6-[3-(1H-Imidazole-4-yl)-propoxy]-3,4-dihydro-2H-naphthalen-1-one, hydrochloride Step 1: 6-[3-(1-Trityl-1H-imidazole-4-yl)-propoxy]-3,4-dihydro-2H-naphthalen-1-one According to the method of Example 32, Step 1, 3-[1-(triphenylmethyl)-1H-imidazole-4-yl]propanol (see for example, *J. Med. Chem.*, 1996;39: 1220–1226) (2.58 g, 7 mmol) was coupled to 6-hydroxy tetralone (1.30 g, 7 mmol) with diethylazodicarboxylate (1.26 mL, 8 mmol) and triphenylphosphine (2.10 g, 8 mmol) in 10 mL of dry THF to afford, after chromatography ($SiO_2$, 50% EtOAc in hexanes), 2.73 g of a 1:1 mixture of the title compound and $Ph_3PO$ as determined by HPLC analysis (C18, 0.1% TFA in $H_2O$:0.1% TFA in AcCN gradient 80:20 to 20:80): title compound, retention time=15.87 minutes (48.2%); $Ph_3PO$, retention time=13.12 minutes (50.1%). CI-MS m/e 279 ($Ph_3PO$), 513 ($M^++1$).

Step 2: 6-[3-(1H-Imidazole-4-yl)-propoxy]-3,4-dihydro-2H-naphthalen-1-one, hydrochloride The product obtained from Step 1 (1.20 g) was heated under reflux in a mixture of 10 mL EtOH and 2N HCl (20 mL) for 1 hour, cooled to room temperature, and evaporated to dryness in vacuo. The residue was suspended in water and the mixture stirred for 1 hour, filtered, and the filtrate was evaporated several times from EtOH. The resulting solid was recrystallized from EtOH/water to afford 0.576 g of the title compound, mp 153–155° C.: CI-MS m/e 271 ($M^++1$).

Elemental Analysis ($C_{16}H_{18}N_2O_2$)×1.0 HCl×1.0 $H_2O$.

EXAMPLE 44

(E,E)-6-(2-Imidazol-1-yl-ethoxy)-2-(3-phenyl-allylidene)-3,4-dihydro-2H-naphthalen-1-one A solution of 0.2 g (0.8 mmol) of 6-[2-(1H-1-imidazolyl)ethoxy]-1,2,3,4-tetrahydro-1-naphthalenone in 2 mL of 4% KOH in EtOH was treated with 0.1 mL (0.8 mmol) of cinnamaldehyde and stirred at room temperature overnight. The mixture was diluted with $H_2O$ and the solid collected. Recrystallization from MeOH/$H_2O$ gave 197 mg (68.2% yield) of the pure product as a yellow solid, mp 198–200° C. The structure was confirmed by NMR and mass spectroscopy. MS m/z 371 (m+$H^+$).

Calculated for $C_{24}H_{22}N_2O_2$×0.2 $H_2O$ (MW 374.04): C, 77.06; H, 6.04; N, 7.49. Found: C, 76.81; H, 5.82; N, 7.42.

EXAMPLE 45

2-[(E)-1-Cyclohexylmethylidene]-6-[2-(1H-1-imidazolyl)ethoxy]-1,2,3,4-tetrahydro-1-naphthalenone, hydrochloride A solution of 0.2 g (0.8 mmol) of 6-[2-(1H-1-imidazolyl)ethoxy]-1,2,3,4-tetrahydro-1-naphthalenone in 2 mL of 4%

KOH in EtOH was treated with 0.1 mL (0.8 mmol) of cyclohexylaldehyde and the solution allowed to stir at room temperature for 3 days. The solution was diluted with $CH_2Cl_2$ and the layers separated. The $CH_2Cl_2$ was washed with saturated NaCl and dried over $MgSO_4$. The $CH_2Cl_2$ was treated with HCl gas and the solvent removed. The residue was taken up in $H_2O$ and freeze-dried. There was obtained 35 mg (10% yield) of a hygroscopic solid. The structure was confirmed by mass spectroscopy. MS m/z 351 (m+H$^+$).

EXAMPLE 46

6-[2-(1H-1-Imidazolyl)ethoxy]-7-methyl-2-[(E)-1-(2-thienyl)methylidene]-1,2,3,4-tetrahydro-1-naphthalenone Step 1: 3-Methoxy-4-methylbenzyl bromide A solution of 18.3 g (0.12 mol) of 3-methoxy-4-methylbenzyl alcohol in 150 mL of $Et_2O$ was treated with 23.8 g (0.12 mol) of $BaCO_3$ and the mixture cooled in ice. This was treated dropwise with 5.8 mL (0.06 mol) of $PBr_3$. After stirring at 0° C. for 15 minutes, the mixture was allowed to stir at room temperature overnight. The mixture was filtered and the solid washed with $Et_2O$. The $Et_2O$ was washed with saturated $NaHCO_3$, then with saturated NaCl. Drying over $MgSO_4$ and removal of the solvent under reduced pressure left 24.17 g (93.5% yield) of the product as an oil. The structure was confirmed by NMR spectroscopy.

Step 2: Dimethyl 2-(3-methoxy-4-methylbenzyl)malonate

A solution of 2.6 g (0.1124 g-atom) of Na in 50 mL of MeOH was treated with 12.9 mL (0.1124 mol) of dimethyl malonate and allowed to stir for 45 minutes. This was then treated dropwise with 24.17 g (0.1124 mol) of 3-methoxy-4-methylbenzyl bromide and the solution heated at reflux overnight. The solvent was removed under reduced pressure and the residue taken up in EtOAc. This was washed with 6% HCl, $H_2O$, saturated $NaHCO_3$, and saturated NaCl. Drying over $MgSO_4$ and removal of the solvent under reduced pressure gave 28.54 g (95.5% yield) of the product as a pale yellow oil. The structure was confirmed by NMR spectroscopy.

Step 3: 3-(3-Methoxy-4-methylphenyl)propanoic acid

A solution of 25.84 g (0.1072 mol) of dimethyl 2-(3-methoxy-4-methylbenzyl)malonate in 150 mL of MeOH was treated with a solution of 20 g (0.5 mol) of NaOH in 100 mL of $H_2O$ and heated at reflux overnight. The solution was concentrated under reduced pressure and the residue taken up in $H_2O$ and washed with $Et_2O$. The solution was acidified to Congo Red end point with dilute HCl and the solution extracted with $Et_2O$. The $Et_2O$ was washed with saturated NaCl and dried over $MgSO_4$. Removal of the solvent under reduced pressure gave 25.6 g of an oil. This was taken up in 125 mL of dioxane and heated at reflux overnight. Removal of the solvent under reduced pressure gave 20.5 g of the crude product. Chromatography on silica gel, eluting with $CHCl_3$/MeOH (98/2) gave 8.65 g (41.6% yield) of the product as a white solid, mp 80–82° C. The structure was confirmed by NMR and mass spectroscopy. MS m/z 195 (M+H$^+$).

Step 4: 3-(3-Methoxy-4-methylphenyl)-1-propanol

A suspension of 3.3 g (98.1 mmol) of lithium aluminum hydride in 40 mL THF was treated dropwise with a solution of 8.65 g (44.5 mmol) of 3-(3-methoxy-4-methylphenyl)propanoic acid in 125 mL of THF. After stirring at room temperature for 0.5 hour, the mixture was heated at reflux for 2 hours. The mixture was cautiously acidified with 1N $H_2SO_4$, then extracted with EtOAc. The EtOAc was washed with 1N $H_2SO_4$, $H_2O$, saturated $NaHCO_3$, and saturated NaCl. Drying over $MgSO_4$ and removal of the solvent under reduced pressure left 7.33 g (91.6% yield) of the product as a clear oil. The structure was confirmed by NMR and mass spectroscopy. MS m/z 181 (M+H$^+$).

Step 5: 4-(3-Bromopropyl)-2-methoxy-1-methylbenzene

Under $N_2$, a solution of 7.33 g (40.7 mmol) of 3-(3-methoxy-4-methylphenyl)-1-propanol in 200 mL of $CH_2Cl_2$ was treated with 10.67 g (40.7 mmol) of triphenylphosphine followed in portions by 7.3 g (40.7 mmol) of recrystallized N-bromosuccinimide. The solution was stirred at room temperature for 2 hours, then filtered through flash silica gel. Removal of the solvent under reduced pressure left 8.68 g (87.9% yield) of the product as a clear oil. The structure was confirmed by NMR spectroscopy.

Step 6: 3-(3-Methoxy-4-methylphenyl)propyl cyanide

A solution of 8.68 g (35.7 mmol) of 4-(3-bromopropyl)-2-methoxy-1-methylbenzene in 50 mL of acetone and 50 mL of EtOH was treated with a solution of 2.8 g (42.8 mmol) of KCN in 20 mL of $H_2O$ and heated at reflux overnight. The solvent was removed under reduced pressure and the residue taken up in EtOAc and washed with $H_2O$, then saturated NaCl. Drying over $MgSO_4$ and removal of the solvent under reduced pressure left 6.75 g (100% yield) of the product as an oil. The structure was confirmed by NMR and IR spectroscopy.

Step 7: 4-(3-Methoxy-4-methylphenyl)butanoic acid

A solution of 6.75 g (35.7 mmol) of 3-(3-methoxy-4-methylphenyl)propyl cyanide in 75 mL of EtOH was treated with a solution of 8.0 g (0.2 mol) of NaOH in 40 mL of $H_2O$ and heated at reflux overnight. The solvent was removed under reduced pressure and the residue taken up in $H_2O$. After washing with $Et_2O$, the aqueous solution was acidified to the Congo Red end point with dilute HCl. A white solid separated which was collected and dried. There was obtained 5.6 g (75.5% yield) of the product, mp 69–70° C. The structure was confirmed by NMR and mass spectroscopy. MS m/z 209 (M+H$^+$).

Step 8: 6-Methoxy-7-methyl-1,2,3,4-tetrahydro-1-naphthalenone

A solution of 5.6 g (26.9 mmol) of 4-(3-methoxy-4-methylphenyl)butanoic acid in 100 mL of $CH_2Cl_2$ was cooled in ice and treated dropwise with 25 mL of trifluoroacetic anhydride. After stirring at 0° C. for 1 hour, the solution was diluted with $Et_2O$ and washed twice with 5% NaOH, then with saturated NaCl. Drying over $MgSO_4$ and removal of the solvent under reduced pressure left the crude product. Chromatography on silica gel, eluting with $CH_2Cl_2$ gave 2.79 g (54.7% yield) of the product as a white solid, mp 104–107° C. The structure was confirmed by NMR and mass spectroscopy. MS m/z 191 (M+H$^+$).

Step 9: 6-Hydroxy-7-methyl-1.2,3,4-tetrahydro-1-naphthalenone

A solution of 2.79 g (14.7 mmol) of 6-methoxy-7-methyl-1,2,3,4-tetrahydro-1-naphthalenone in 150 mL of $CH_2Cl_2$ was cooled in ice and treated with 20 mL (0.22 mol) of $BBr_3$. After stirring at 0° C. for 0.5 hour, the solution was stirred at room temperature overnight. The solution was poured into ice water and extracted with $Et_2O$. The $Et_2O$ was extracted twice with 5% NaOH and the NaOH washed with $Et_2O$. The NaOH solution was acidified to the Congo Red end point with dilute HCl, then extracted with $Et_2O$. The $Et_2O$ was washed with saturated NaCl and dried over $MgSO_4$. Removal of the solvent under reduced pressure left the crude product. This was taken up in acetone and treated with charcoal. Filtering through Celite and removal of the solvent under reduced pressure left 2.08 g (80.6% yield) of the product as a brown solid. The structure was confirmed by NMR and mass spectroscopy. MS m/z 177 (M+H$^+$).

Step 10: 6-[2-(1H-1-Imidazolyl)ethoxy]-7-methyl-1,2,3,4-tetrahydro-1-naphthalenone Under $N_2$, a solution of 2.08 g (11.8 mmol) of 6-hydroxy-7-methyl-1,2,3,4-tetrahydro-1-naphthalenone in 25 mL of THF was treated with 1.46 g (13.9 mmol) of 2-(1H-1-imidazolyl)-1-ethanol and 3.1 g (11.8 mmol) of triphenylphosphine. The solution was cooled in ice and treated with a solution of 1.9 mL (11.8 mmol) of diethyl azodicarboxylate in 5 mL of THF. The solution was allowed to stir at room temperature overnight. The mixture was diluted with EtOAc and washed twice with $H_2O$, twice with saturated $NaHCO_3$, then with saturated NaCl. Drying over $MgSO_4$ and removal of the solvent under pressure left the crude product. Chromatography on silica gel, eluting with $CHCl_3$/MeOH (95/5) gave the product which was recrystallized from EtOAc/hexane to give 1.05 g (32.9% yield) of the product as a tan solid, mp 118–120° C. The structure was confirmed by NMR and mass spectroscopy. MS m/z 271 (M+H$^+$).

Step 11: 6-[2-(1H-1-Imidazolyl)ethoxy]-7-methyl-2-[(E)-1-(2-thienyl)methylidene]-1,2,3,4-tetrahydro-1-naphthalenone A solution of 0.2 g (0.7 mmol) of 6-[2-(1H-1-imidazolyl) ethoxy]-7-methyl-1,2,3,4-tetrahydro-1-naphthalenone in 2 mL of 4% KOH in EtOH was treated with 0.1 mL (0.7 mmol) of 2-thiophene-aldehyde and let stirring at room temperature overnight. The mixture was diluted with $H_2O$ and the solid collected. Recrystallization from MeOH/$H_2O$ gave 165 mg (61.3% yield) of the product as a yellow solid, mp 150–151° C. The structure was confirmed by NMR and mass spectroscopy. MS m/z 365 (M+H$^+$).

Calculated for $C_{21}H_{20}N_2O_2 \times 0.4\ H_2O$ (MW 371.59): C, 67.87; H, 5.64; N, 7.54. Found: C, 67.82; H, 5.48; N, 7.51.

EXAMPLE 47

6-[2-(1H-1-Imidazolyl)ethoxy]-5-methyl-1,2,3,4-tetrahydro-1-naphthalenone

Step 1: 3-Hydroxy-2-methylbenzoic acid

A solution of 20.6 g (0.125 mol) of methyl 3-amino-2-methylbenzoate in 150 mL of HOAc and 25 mL of conc. $H_2SO_4$ was cooled in ice and diazotized by the dropwise addition of a solution of 8.7 g (0.125 mol) of $NaNO_2$ in 50 mL of $H_2O$. After stirring for 15 minutes, the diazonium solution was added dropwise to a boiling solution of 200 mL of 50% $H_2SO_4$, and the refluxing continued for 15 minutes after the addition was complete. The mixture was diluted with $H_2O$ and extracted twice with $Et_2O$. The $Et_2O$ was washed 5 times with $H_2O$, then with saturated NaCl. Drying over $MgSO_4$ and removal of the solvent under reduced pressure left 17.98 g (94.4% yield) of the product as a tan solid, mp 137–140° C. The structure was confirmed by NMR spectroscopy.

Step 2: Methyl 3-hydroxy-2-methylbenzoate

A solution of 17.98 g (0.118 mol) of 3-hydroxy-2-methylbenzoic acid in 200 L of MeOH was treated with 2.0 mL of conc. $H_2SO_4$ and heated at reflux overnight. The solution was concentrated under reduced pressure and diluted with $H_2O$. The product was collected and recrystallized from MeOH/$H_2O$ to give 12.85 g (65.6% yield) of a tan solid, mp 74–75° C. The structure was confirmed by NMR and mass spectroscopy. MS m/z 167 (M+H$^+$).

Step 3: Methyl 3-methoxy-2-methylbenzoate

A solution of 13.98 g (0.0841 mol) of methyl 3-hydroxy-2-methylbenzoate in 120 mL of DMF was cooled in ice and treated dropwise with 200 mL (0.1 mol) of a 0.5 M solution of KHMDS in toluene. After stirring for 10 minutes, 7.8 mL (0.126 mol) of methyl iodide was added and the solution allowed to stir at room temperature overnight. The solution was diluted with EtOAc and washed twice with 6% HCl, 3 times with $H_2O$, 10% $NaHSO_3$, then saturated NaCl. Drying over $MgSO_4$ and removal of the solvent under reduced pressure left 14.22 g (93.8% yield) of the product as a golden oil. The structure was confirmed by NMR and mass spectroscopy. MS m/z 181 (M+H$^+$).

Step 4: (3-Methoxy-2-methylphenyl)methanol

A suspension of 4.5 g (0.118 mol) of lithium aluminum hydride in 100 mL of THF was treated dropwise with a solution of 14.22 g (78.9 mmol) of methyl 3-methoxy-2-methylbenzoate in 120 mL of THF. The mixture was heated at reflux for 2.5 hours, then cautiously decomposed with 1N$H_2SO_4$. The mixture was extracted with EtOAc, and the EtOAc washed with dilute HCl, $H_2O$, saturated $NaHCO_3$, and saturated NaCl. Drying over $MgSO_4$ and removal of the solvent under reduced pressure left 11.5 g (95.8% yield) of the product as a tan solid, mp 63–64° C. The structure was confirmed by NMR and mass spectroscopy MS n/z 153 (M+H$^+$).

Step 5: 1-(Bromomethyl)-3-methoxy-2-methylbenzene

Following the procedure of Example 46, Step 1, but using 11.5 g (75.6 mmol) of (3-methoxy-2-methylphenyl) methanol, there was obtained 15.96 g (98.3% yield) of the product as a golden oil. The structure was confirmed by spectroscopy.

Step 6: Dimethyl 2-(3-methoxy-2-methylbenzyl)malonate

Following the procedure of Example 46, Step 2, but using 15.96 g (72.4 mmol) of 1-(bromomethyl)-3-methoxy-2-methylbenzene, there was obtained 19.0 g (96.2% yield) of the product as an oil that crystallized on standing. The structure was confirmed by NMR and mass spectroscopy. MS m/z 267 (M+H$^+$).

Step 7: 3-(3-Methoxy-2-methylphenyl)propanoic acid

Following the procedure of Example 46, Step 3, but using 19.0 g (71.4 mmol) of dimethyl 2-(3-methoxy-2- methylbenzyl)malonate, there was obtained 10.33 g (74.6% yield) of the product as a white solid, mp 143–147° C. The structure was confirmed by NMR and mass spectroscopy. MS m/z 195 (M+H$^+$).

Step 8: 3-(3-Methoxy-2-methylphenyl)-1-propanol

Following the procedure of Example 46, Step 4, but using 10.33 g (53.2 mmol) of 3-(3-methoxy-2-methylphenyl) propanoic acid, there was obtained 9.48 g (99% yield) of the product as a clear oil. The structure was confirmed by NMR and mass spectroscopy. MS m/z 181 (M+H$^+$).

Step 9: 1-(3-Bromopropyl)-3-methoxy-2-methylbenzene

Following the procedure of Example 46, Step 5, but using 9.48 g (52.6 mmol) of 3-(3-methoxy-2-methylphenyl)-1-propanol, there was obtained 12.78 g (100% yield) of the product as an oil. The structure was confirmed by NMR spectroscopy.

Step 10: 3-(3-Methoxy-2-methylphenyl)propyl cyanide

Following the procedure of Example 46, Step 6, but using 12.78 g (52.6 mmol) of 1-(3-bromopropyl)-3-methoxy-2-methylbenzene, there was obtained 9.94 g (100% yield) of the product as an oil. The structure was confirmed by NMR and mass spectroscopy. MS m/z 190 (M+H$^+$).

Step 11: 4-(3-Methoxy-2-methylphenyl)butanoic acid

Following the procedure of Example 46, Step 7, but using 9.94 g (52.5 mmol) of 3-(3-methoxy-2-methylphenyl)propyl cyanide, there was obtained 8.41 g (77% yield) of the product as a white solid, mp 105–107° C. The structure was confirmed by NMR and mass spectroscopy. MS m/z 209 (M+H$^+$).

Step 12: 6-Methoxy-5-methyl-1,2,3,4-tetrahydro-1-naphthalenone

Following the procedure of Example 46, Step 8, but using 8.41 g (40.4 mmol) of 4-(3-methoxy-2-methylphenyl) butanoic acid, there was obtained 7.29 g (94.9% yield) of the product as a pink solid, mp 103–105° C. The structure was confirmed by No and mass spectroscopy. MS m/z 191 (M+H$^+$).

Step 13: 6-Hydroxy-5-methyl-1,2,3,4-tetrahydro-1-naphthalenone

Following the procedure of Example 46, Step 9, but using 7.29 g (38.3 mmol) of 6-methoxy-5-methyl-1,2,3,4-tetrahydro-1-napthalenone, there was obtained 4.26 g (63.1% yield) of the product as a brown solid, mp 195–197° C. The structure was confirmed by NMR and mass spectroscopy. MS m/z 177 (M+H$^+$).

Step 14: 6-[2-(1H-1-Imidazolyl)ethoxy]-5-methyl-1,2,3,4-tetrahydro-1-naphthalenone Following the procedure of Example 46, Step 10, but using 4.26 g (24.4 mmol) of 6-hydroxy-5-methyl-1,2,3,4-tetrahydro-1-naphthalenone, there was obtained 3.13 g (47.9% yield) of the product as a pale, yellow oil which crystallized on standing. Trituration with hexane gave a white solid, mp 110–112° C. The structure was confirmed by No and mass spectroscopy. MS m/z 271 (M+H$^+$).

Calculated for $C_{16}H_{18}N_2O_2 \times 0.2\ H_2O$ (MW 270.32): C, 70.15; H, 6.77; N, 10.23. Found: C, 70.18; H, 6.55; N, 10.16.

EXAMPLE 48

6-[2-(1H-1-Imidazolyl)ethoxy]-5-methyl-2-[(E)-1-(2-thienyl)methylidene]-1,2,3,4-tetrahydro-1-naphthalenone Following the procedure of Example 46, Step 11, but using 0.27 g (1.0 mmol) of 6-[2-(1H-1-imidazolyl)ethoxy]-5-methyl-1,2,3,4-tetrahydro-1-naphthalenone, there was obtained 227 mg (63.1% yield) of the product as a pale yellow solid, mp 182–184° C. The structure was confirmed by NMR and mass spectroscopy. MS m/z 365 (M+H$^+$).

Calculated for $C_{21}H_{20}N_2O_2S$ (MW 364.39): C, 69.22; H, 5.53; N, 7.69. Found: C, 69.04; H, 5.47; N, 7.62.

EXAMPLE 49

7-[2-(1H-1-Imidazolyl)ethoxy]-3-[(E)-1-(2-thienyl) methylidene]-1,2,3,4-tetrahydro-4-quinolinone Step 1: 7-Hydroxy-1,2,3,4-tetrahydro-4-quinolinone A solution of 1.1 g (6.2 mmol) of 7-methoxy-1,2,3,4-tetrahydro-4-quinolinone (*Rec. Trav. Chim.*, 1963;82:39) in 35 mL of $CH_2Cl_2$ was cooled in ice and treated with 5.0 mL of $BBr_3$. After stirring at 0° C. for 0.5 hour, the solution was allowed to stir at room temperature overnight. The solution was poured into ice water and made basic with 50% NaOH. After extracting with $Et_2O$, the pH was brought to 5.5 with dilute HCl, and the solution extracted twice with EtOAc. The EtOAc was washed with saturated NaCl and dried over $MgSO_4$. Removal of the solvent under reduced pressure gave 0.5 g (49.5% yield) of the product as an orange solid. The structure was confirmed by NMR and mass spectroscopy. MS m/z 164 (M+H$^+$).

Step 2: 7-[2-(1H-1-Imidazolyl)ethoxy]-1,2,3,4-tetrahydro-4-quinolinone

Under $N_2$, a solution of 0.8 g (5.0 mmol) of 7-hydroxy-1,2,3,4-tetrahydro-4-quinolinone in 20 mL of THF was treated with 0.62 g (5.5 mmol) of 2-(1H-1-imidazolyl)-1-ethanol and 1.13 (5.0 mmol) of tripenylphosphine. The mixture was warmed to effect solution, then allowed to cool to room temperature. This was then treated over 10 minutes with 0.8 mL (5.0 mmol) of diethyl azodicarboxylate. Some solid formed and the mixture was allowed to stir at room temperature for 3 days. The mixture was diluted with EtOAc and filtered. The filtrate was washed twice with $H_2O$, saturated $NaHCO_3$, then with saturated NaCl. Drying over MgSO4 and removal of the solvent under reduced pressure left the crude product. Chromatography on silica gel, eluting with $CHCl_3$/MeOH (90/10), gave 150 mg (11.8% yield) of the product as a golden oil. The structure was confirmed by mass spectroscopy. MS m/z 258 (M+H$^+$).

Step 3: 7-[2-(1H-1-Imidazolyl)ethoxy]-3-[(E)-1-(2-thienyl)methylidene]-1,2,3,4-tetrahydro-4-quinolinone A solution of 0.15 g (0.6 mmol) of 7-[2-(1H-1-imidazolyl) ethoxy]-1,2,3,4-tetrahydro-4-quinolinone in 2.0 mL of a 4% solution of KOH in EtOH was treated with 0.1 mL (0.8 mmol) of 2-thiophenealdehyde and allowed to stir at room temperature overnight. The solution was diluted with $H_2O$ and the precipitated solid collected. Resuspension in $H_2O$ and filtering gave 60 mg (28.6% yield) of the pure product as a pink solid, mp 211–213° C. The structure was confirmed by NMR and mass spectroscopy. MS m/z 352 (M+H$^+$).

Calculated for $C_{19}H_{17}N_3O_2S \cdot 0.4\ H_2O$ (MW 358.56): C, 63.64; H, 5.00; N, 11.72. Found: C, 63.54; H. 4 83; N, 11.47.

EXAMPLE 50

7-[2-(1H-1-Imidazolyl)ethoxy]-4H-4-chromenone

Under $N_2$, a solution of 0.75 g (4.6 mmol) of 7-hydroxy-4H-4-chromenone (*J. Med. Chem.* 1991;34:248) in 20 mL of THF was treated with 1.21 g (4.6 mmol) of triphenylphosphine and 0.5 g (5.1 mmol) of 2-(1H-1-imidazolyl)-1-ethanol and the solution cooled in ice. This was then treated over 10 minutes with 0.72 mL (4.6 mmol) of diethyl azodicarboxylate, and the solution stirred at room temperature overnight. The solution was diluted with EtOAc, washed twice with $H_2O$, twice with saturated $NaHCO_3$, and then with saturated NaCl. Drying over $MgSO_4$ and removal of the solvent under reduced pressure gave the crude product. Chromatography on silica gel, eluting with a gradient of $CH_2Cl_2$ to $CH_2Cl_2$/MeOH (96/4) gave 0.12 g (10% yield) of the product as a pink solid, mp 131–133° C. The structure was confirmed by NMR and mass spectroscopy. MS m/z 257 (M+H$^+$).

Calculated for $C_{14}H_{12}N_2O_3 \times 0.08\ CH_2Cl_2$ (MW 262.76): C, 64.34; H, 4.66; N, 10.66. Found: C, 64.34; H, 4.72; N, 10.66.

EXAMPLE 51

7-[2-(1H-1-Imidazolyl)ethoxy]-4-chromanone

Under $N_2$, a solution of 2.0 g (0.012 mol) of 7-hydroxy-4-chromanone (*J. Org. Chem.*, 1994;59:1216) in 25 mL of THF was treated with 1.29 g (0.013 mol) of 2-(1H-1-imidazolyl)-1-ethanol and 3.15 g (0.012 mol) of triphenylphosphine. The solution was cooled in ice and treated over 10 minutes with a solution of 1.89 mL (0.012 mol) of diethyl azodicarboxylate in 5.0 mL of THF. After stirring at room temperature for 3 days, the solution was diluted with EtOAc and washed with saturated NaCl. Drying over $MgSO_4$ and removal of the solvent under reduced pressure left the crude product. Chromatography on silica gel, eluting with a gradient of $CHCl_3$ to $CHCl_3$/MeOH (96/4) gave the product which was recrystallized from EtOAc/hexane to give 0.92 g (29.7% yield) of a white solid, mp 128–130° C. The structure was confirmed by NMR and mass spectroscopy. MS m/z 259 (M+H$^+$).

Calculated for $C_{14}H_{14}N_2O_3$ (MW 258.27): C, 65.11; H, 5.46; N, 10.85. Found: C, 64.76; H, 5.45; N, 10.71.

EXAMPLE 52

7-[2-(1H-1-Imidazolyl)ethoxy]-3-[(E)-1-(2-thienyl) methylidene]4-chromanone

A solution of 0.25 g (0.97 mmol) of 7-[2-(1H-1-imidazolyl)ethoxy]-4-chromanone in 1.0 mL of HOAc containing 0.1 mL of conc. $H_2SO_4$ was treated with 0.1 mL (0.97 mmol) of 2-thiophenealdehyde and the solution stirred at room temperature overnight. The solution was diluted with $H_2O$ and washed with EtOAc. The aqueous phase was made basic with dilute NaOH causing a solid to separate. This was collected and dried giving 0.23 g (67.6% yield) of the product as a brown solid. The structure was confirmed by NMR and mass spectroscopy. MS m/z 353 (M+H$^+$).

Calculated for $C_{19}H_{16}N_2O_3S \times 0.3\ H_2O$ (MW 357.74): C, 63.79; H, 4.68; N, 7.83. Found: C, 63.73; H, 4.31; N, 7.65.

EXAMPLE 53

6-[2-(1H-1-Imidazolyl)ethoxyl]-1,2,3,4-tetrahydro-1-naphthalenone oxime

A solution of 1.0 g (3.9 mmol) of 6-[2-(1H-1-imidazolyl)ethoxy]-1,2,3,4-tetrahydro-1-naphthalenone in 10 mL of pyridine was treated with 0.41 g (5.9 mmol) of hydroxylamine×HCl and the solution heated at reflux overnight. The solution was diluted with $H_2O$ and the product collected and dried. There was obtained 0.88 g (83% yield) of the product as a white solid, mp 177–179° C. The structure was confirmed by NMR and mass spectroscopy. MS m/z 272 (M+H$^+$).

Calculated for $C_{15}H_{17}N_3O_2$ (MW 271.31): C, 66.40; H, 6.32; N, 15.49. Found: C, 66.06; H, 6.23; N, 15.41.

EXAMPLE 54

[6-(2-Imidazol-1-yl-ethoxy)-3,4-dihydro-2H-naphthalen-1-ylideneaminooxy]-acetic acid A solution of 1.0 g (3.9 mmol) of 6-[2-(1H-1-imidazolyl)ethoxy]-1,2,3,4-tetrahydro-1-naphthalenone in 10 mL of pyridine was treated with 1.02 g (9.3 mmol) of carboxymethoxyamine×0.5 HCl and the solution heated at reflux for 2 days. The solution was diluted with $H_2O$ and extracted with EtOAc. On standing, the aqueous phase deposited a solid which was collected and dried. There was obtained 0.56 g (43% yield) of the product as a white solid, mp 193–195° C. The structure was confirmed by NMR and mass spectroscopy. MS m/z 330 (M+H$^+$).

Calculated for $C_{17}H_{19}N_3O_4 \times 0.2\ H_2O$ (MW 332.95): C, 61.32; H, 5.87; N, 12.62. Found: C, 61.38; H, 5.61; N, 12.63.

EXAMPLE 55

2-[6-(2-Imidazol-1-yl-ethoxy)-3,4-dihydro-2H-naphthalen-1-ylideneaminooxy]-N-(2-methyl-2-phenyl-propyl)-acetamide A solution of 0.28 g (0.85 mmol) of [6-(2-imidazolyl-1-yl-ethoxy)-3,4-dihydro-2H-naphthalen-1-ylideneaminooxy]-acetic acid in 20 mL of EtOAc and 10 mL of DMF was treated with 0.13 g (9.3 mmol) of HOBT and 0.17 g (9.3 mmol) of 2-methyl-2-phenyl-1-propanamine× HCl. $Et_3N$ (0.13 mL, 9.3 mmol) was then added followed by 0.19 g (9.3 mmol) of dicyclohexylcarbodiimide, and the mixture stirred at room temperature for 3 days. The mixture was diluted with EtOAc, filtered, and the filtrate washed 3 times with $H_2O$, then twice with saturated $NaHCO_3$, then with saturated NaCl. Drying over $MgSO_4$ and removal of the solvent under reduced pressure gave the crude product. Chromatography on silica gel, eluting with a gradient of $CH_2Cl_2$ to $CH_2Cl_2$/MeOH (96/4) gave 0.34 g (87% yield) of the product as a white solid foam. The structure was confirmed by NMR and mass spectroscopy. MS m/z 461 (M+H$^+$).

Calculated for $C_{27}H_{32}N_4O_3 \times 0.1\ CH_2Cl_2$ (MW 469.05): C, 69.39; H, 6.92; N, 11.95. Found: C, 69.38; H, 6.99; N,11.67.

EXAMPLES 56–74

Examples 56–74 were prepared as part of a parallel synthesis array. A solution of 0.15 g (0.59 mmol) of 6-[2-(1H-1-imidazolyl)ethoxy]-1,2,3,4-tetrahydro-1-naphthalenone in 2 mL of a 4% KOH in EtOH solution was treated with 0.95 equivalents of the appropriate aromatic aldehyde and shaken overnight. Those samples where a solid was present were diluted with $H_2O$ and the solid collected and dried. Those samples where a solution was present were mixed with 2 mL of $CH_2Cl_2$ and shaken. The $CH_2Cl_2$ layer was separated and dried in a stream of $N_2$. The purity of the samples was determined by HPLC and the structures confirmed by mass spectroscopy.

EXAMPLE 56

2-[(E)-1-(2-Chlorophenyl)methylidene]-6-[2-(1H-1-imidazolyl)ethoxy]-1,2,3,4-tetrahydro-1-naphthalenone MS m/z 379 (M+H$^+$), purity 94.8%.

EXAMPLE 57

2-[(E)-1-(3-Chlorophenyl)methylidene]-6-[2-(1H-1-imidazolyl)ethoxy]-1,2,3,4-tetrahydro-1-naphthalenone MS m/z 379 (M+H$^+$), purity 84.1%.

EXAMPLE 58

2-[(E)-1-(4-Chlorophenyl)methylidene]-6-[2-(1H-1-imidazolyl)ethoxy]-1,2,3,4-tetrahydro-1-naphthalenone MS m/z 379 (M+H$^+$), purity 99.0%.

EXAMPLE 59

2-[(E)-1-(1,3-Benzodioxol-5-yl)methylidene]-6-[2-(1H-1-imidazolyl)ethoxy]-1,2,3,4-tetrahydro-1-naphthalenone MS m/z 389 (M+H$^+$), purity 78.1%.

EXAMPLE 60

2-[(E)-1-(4-Fluorophenyl)methylidene]-6-[2-(1H-1-imidazolyl)ethoxy]-1,2,3,4-tetrahydro-1-naphthalenone MS m/z 363 (M+H$^+$), purity 79.7%.

EXAMPLE 61

2-[(E)-1-(2,3-Dichlorophenyl)methylidene]-6-[2-(1H-1-imidazolyl)ethoxy]-1,2,3,4-tetrahydro-1-naphthalenone MS m/z 413 (M+H$^+$), purity 90.1%.

EXAMPLE 62

2-[(E)-1-(2,6-Dichlorophenyl)methylidene]-6-[2-(1H-1-imidazolyl)ethoxy]-1,2,3,4-tetrahydro-1-naphthalenone MS m/z 413 (M+H$^+$), purity 96.3%.

EXAMPLE 63

2-[(E)-1-(3,4-Dichlorophenyl)methylidene]-6-[2-(1H-1-imidazolyl)ethoxy]-1,2,3,4-tetrahydro-1-naphthalenone MS m/z 413 (M+H$^+$), purity 99.4%.

EXAMPLE 64

2-[(E)-1-(3,5-Dichlorophenyl)methylidene]-6-[2-(1H-1-imidazolyl)ethoxy]-1,2,3,4tetrahydro-1-naphthalenone MS m/z 413 (M+H$^+$), purity 52.9%.

EXAMPLE 65

2-[(E)-1(2,5-Dimethoxphenyl)methylidene]-6-[2-(1H1-imidazolylethoxy-]1,2,3,4tetrahydro-1-naphthalenone MS m/z 405 (M+H$^+$), purity 84.0%.

EXAMPLE 66

2-[(E)-1-(2,3-Dimethoxyphenyl)methylidene]-6-[2-(1H-1-imidazolyl)ethoxy]-1,2,3,4-tetrahydro-1-naphthalenone MS m/z 405 (M+H$^+$), purity 84.2%.

EXAMPLE 67

6-[2-(1H-1-Imidazolyl)ethoxy]-2-(E)-1-[2-(trifluoromethyl)phenyl]methylidene-1,2,3,4-tetrahydro-1-naphthalenone MS m/z 413 (M+H$^+$), purity 71.3%

EXAMPLE 68

6-[2-(1H-1-Imidazolyl)ethoxy]-2-[(E)-1-(2,4,6-trimethoxyphenyl)methylidene]-1,2,3,4-tetrahydro-1-naphthalenone MS m/z 435 (M+H$^+$), purity 81.0%.

EXAMPLE 69

6-[2-(1H-1-Imidazolyl)ethoxy]-2-[(E)-1-(2,3,4-trimethoxyphenyl)methylidene]-1,2,3,4-tetrahydro-1-naphthalenone MS m/z 435 (M+H$^+$), purity 93.3%

EXAMPLE 70

6-[2-(1H-1-Imidazolyl)ethoxy]-2-[(E)-1-(4-iodophenyl)methylidene]-1,2,3,4-tetrahydro-1-naphthalenone MS m/z 471 (M+H$^+$), purity 96.1%.

EXAMPLE 71

2-(E)-1-[4-(Dimethylamino)phenyl]methylidene-6-[2-(1H-1-imidazolylethoxy]-1,2,3,4-tetrahydro-1-naphthalenone MS m/z 388 (M+H$^+$), purity 40.6%.

EXAMPLE 72

2-(E)-1-[4-(tert-Butyl)phenyl]methylidene-6-[2-(1H-1-imidazolyl)ethoxy]-1,2,3,4-tetrahydro-1-naphthalenone MS m/z 417 (M+H$^+$), purity 100%.

EXAMPLE 73

6-[2-(1H-1-Imidazolyl)ethoxy]-2-[(E)-1-(3-methoxyphenyl)methylidene]-1,2,3,4-tetrahydro-1-naphthalenone MS m/z 375 (M+H$^+$), purity 87.8%.

EXAMPLE 74

6-[2-(1H-1-Imidazolyl)ethoxy]-2-[(E)-1-(3-methylphenyl)methylidene]-1,2,3,4-tetrahydro-1-naphthalenone MS m/z 359 (M+H$^+$), purity 86.5%.

EXAMPLE 75

2-(E)-1-[4-(Diethylamino)phenyl]methylidene-6-[2-(1H-1-imidazolyl)ethoxy]-1,2,3,4-tetrahydro-1-naphthalenone, di-trifluoroacetic acid salt A solution of 0.35 g (2.0 mmol) of 4-diethylaminobenzaldehyde and 0.26 g (1.0 mmol) of 6-[2-(1H-1-imidazolyl)ethoxy]-1,2,3,4-tetrahydro-1-naphthalenone in 1.0 mL of a 4% solution of KOH in EtOH was heated at reflux overnight. The solution was diluted with EtOAc and washed with H$_2$O, then saturated NaCl. Drying over MgSO$_4$ and removal of the solvent under pressure left the crude product. Chromatography on silica gel, eluting with a gradient of EtOAc to EtOAc/MeOH (96/4) gave 0.23 g of material of 86% purity. Preparative HPLC gave 60 mg of pure product isolated as the di-trifluoroacetic acid salt. The structure was confirmed by NMR and mass spectroscopy. MS m/z 416 (M+H$^+$).

Calculated for C$_{26}$H$_{29}$N$_3$O$_2$×2.3 C$_2$HO$_2$F$_3$×1.0 H$_2$O (MW 695.80): C, 52.82; H, 4.82; N, 6.04. Found: C, 52.73; H, 4.47; N, 5.88.

EXAMPLE 76

7-[2-(1H-1-Imidazolyl)ethoxy]-2-phenyl-4-chromanone

A solution of 5.0 g (20.8 mmol) of 7-hydroxy-2-phenyl-4-chromanone in 200 mL of THF was treated with 6.22 g (23.7 mmol) of triphenylphosphine and 2.65 g (23.7 mmol) of 2-(1H-1-imidazolyl)-1-ethanol. A solution of 4.13 g (23.7 mmol) of diethyl azodicarboxylate in 25 mL of THF was added dropwise and the solution allowed to stir at room temperature overnight. The solvent was removed under pressure, and the residue taken up in 1N citric acid and washed three times with Et$_2$O. The aqueous phase was adjusted to pH 7 with 50% NaOH and extracted with EtOAc. The EtOAc was washed with saturated NaCl and dried over MgSO$_4$. Treatment with charcoal and removal of the solvent under pressure gave 3.0 g (43% yield) of the product as a white solid, mp 139–140° C. The structure was confirmed by NMR and mass spectroscopy. MS m/z 335 (M+H$^+$).

Calculated for C$_{20}$H$_{18}$N$_2$O$_3$ (MW 334.38): C, 71.84; H, 5.43; N, 8.38. Found: C, 71.60; H, 5.29; N, 8.31.

EXAMPLE 77

7-[2-(1H-1-Imidazolyl)ethoxy]-2-phenyl-4H-4-chromenone

Following the procedure of Example 76, but using 2.0 g (8.4 mmol) of 7-hydroxy-2-phenyl-4H-4-chromenone, there was obtained 0.86 g (31% yield) of the product as a white solid, mp 155–159° C. The structure was confirmed by NMR and mass spectroscopy. MS m/z 333 (M+H$^+$).

Calculated for C$_{20}$H$_{16}$N$_2$O$_3$ (MW 332.36): C, 72.28; H, 4.85; N, 8.43. Found: C, 72.07; H, 4.70; N, 8.36.

EXAMPLE 78

6-[2-(1H-1-Imidazolyl)propoxy]-1,2,3,4-tetrahydro-1-naphthalenone

Step 1: Ethyl 2-(1H-1-Imidazolyl)propanoate

A suspension of 16.0 g (0.4 mol) of NaH-oil (60%) was washed with hexane to remove the oil and then resuspended in 400 mL of THF. This was then treated dropwise with a solution of 27.23 g (0.4 mol) of imidazole in 150 mL of THF and then refluxed for 1hour. This was then treated dropwise with a solution. of 72.4 g (0.4 mol) of ethyl 2-bromopropanoate in 100 mL of THF and the mixture heated at reflux for 2.5 hours. The mixture was filtered and the solvent removed under reduced pressure. The residue was taken up in Et$_2$O and washed with H$_2$O, then saturated NaCl. Drying over MgSO$_4$ and treatment with charcoal gave the crude product. This was triturated with pentane and the pentane removed under reduced pressure to give 38.56 g (57.3% yield) of the product as an oil. The structure was confirmed by NMR and mass spectroscopy. MS m/z 169 (M+H$^+$).

Step 2: 2-(1H-1-Imidazolyl)-1-propanol

A suspension of 16.6 g (0.437 mol) of lithium aluminum hydride in 700 mL of THF was warmed to 40° C. and treated dropwise with 36.8 g (0.219 mol) of ethyl 2-(1H-1-imidazolyl)propanoate and the suspension allowed to stir at room temperature for 2.5 hours. The mixture was decomposed with dilute NaOH, filtered, and the solid washed with THF. The solvent was removed under reduced pressure and the residue distilled at 155–170° C./0.5 mm Hg. There was obtained 18.6 g (67% yield) of the product as an oil. The structure was confirmed by NMR and mass spectroscopy. MS m/z 127 (M+H$^+$).

Step 3: 6-[2-(1H-1-Imidazolyl)propoxy]-1,2,3,4-tetrahydro-1-naphthalenone

Following the procedure of Example 76, but using 1.79 g (14.2 mmol) of 2-(1H-1-imidazolyl)-1-propanol and 2.0 g (12.3 mmol) of 6-[2-(1H-1-imidazolyl)ethoxy]-1,2,3,4-tetrahydro-1-naphthalenone, there was obtained 1.63 g (49% yield) of the product as a white solid, mp 132–135° C. The structure was confirmed by NMR and mass spectroscopy. MS m/z 271 (M+H$^+$).

Calculated for C$_{16}$H$_{18}$N$_2$O$_2$ (MW 270.34): C,71.09; H, 6.71; N, 10.36. Found: C, 70.71; H, 6.70; N, 10.20.

EXAMPLE 79

6-[2-(1H-1-Imidazolyl)propoxy]-2-[(E)-1-(2-thienyl)methylidene]-1,2,3,4-tetrahydro-1-naphthalenone Following the procedure of Example 44, but using 0.73 g (2.7 mmol) of 6-[2-(1H-1-imidazolyl)propoxy]-1,2,3,4-tetrahydro-1-naphthalenone, there was obtained 0.62 g (98.2% yield) of the product as a pale yellow solid, mp 160–162° C. The structure was confirmed by NMR and mass spectroscopy. MS m/z 365 (M+H$^+$).

Calculated for C$_{21}$H$_{20}$N$_2$O$_2$S (MW 364.47): C, 69.21; H, 5.53; N, 7.69; S, 8.80. Found: C, 68.10; H, 5.31; N, 7.42; S, 8.53.

EXAMPLE 80

6-[2-(1H-1-Imidazolyl)-1-phenylethoxy]-1,2,3,4-tetrahydro-1-naphthalenone

Step1: 2-(1H-1-Imidazolyl)-1-phenyl-1-ethanol

A solution of 17.6 g (0. 2 58 mol) of imidazole in 100 mL of absolute EtOH was treated with 0.6 mL (4.0 mmol) of pyridine and refluxed for 25 minutes. This was then treated dropwise with a solution of 31.06 g (0.258 mol) of styrene oxide and the solution heated at reflux overnight. The solvent was removed under reduced pressure and the residue taken up in Et$_2$O and washed with H$_2$O. A solid separated which was collected and dissolved in warm CHCl$_3$/EtOAc. The organic phase was washed with saturated NaCl and dried over MgSO$_4$. Treatment of the filtrate with charcoal, filtering, and concentrating to ⅓ volume caused a solid to separate. There was collected 17.09 g (35% yield) of the product as a white solid, mp 146–148° C. The structure was confirmed by NMR and mass spectroscopy. MS m/z 189 (M+H$^+$).

Step 2: 6-[2H-1-Imidazolyl)-1-phenylethoxy]-1,2,3,4-tetrahydro-1-naphthalenone

Following the procedure of Example 78, Step 3, but using 2.63 g (4.0 mmol) of 2-(1H-1-imidazolyl)-1-phenyl-1-ethanol and 2.0 g (12.3 mmol) of 6-[2-(1-H-1-imidazolyl)ethoxy]1,2,3,4-tetrahydro -1-naphthalenone, there was obtained 3.83 g (93.6% yield) of the product as a glass. The structure was confirmed by NMR and mass spectroscopy. MS m/z 333 (M+H$^+$).

EXAMPLE 81

6-(2-Imidazol-1-yl-1-phenyl-ethoxy)-2-thiophen-2-ylmethylene-3,4-dihydro-2H-naphthalen-1-one Following the procedure of Example 46, Step 11, but using the product of Example 80, there was obtained the product as yellow solid foam. The structure was confirmed by NMR and mass spectroscopy. MS m/z 427 (M+H$^+$).

EXAMPLE 82

2-[6-(2-Imidazol-1-yl-ethoxy)-3,4-dihydro-2H-naphthalen-1-ylideneaminooxy]-N-(1-phenyl-cyclobutylmethyl)-acetamide Following the procedure of Example 55 but using (1-phenylcyclobutyl)-methanamine, there was obtained the product as a white solid foam. The structure was confirmed by NMR and mass spectroscopy. MS m/z 473 (M+H$^+$).

EXAMPLE 83

7-[2-(1H-Imidazolyl)ethoxy]-2,2-dimethyl-4-chromanone

Following the procedure of Example 30 but using 7-hydroxy-2,2-dimethyl-4-chromanone and 1-(2-hydroxyethyl)imidazole, there was obtained the title compound as a solid, mp 84–86° C. The structure was confirmed by NMR and mass spectroscopy. MS m/z 287 (M+H$^+$).

Calculated for C$_{16}$H$_{18}$N$_2$O$_3$ (MW 286.33): C, 67.12; H, 6.34; N, 9.78. Found: C, 67.00; H, 6.19; N, 9.72.

The data in the table below shows the farnesyl protein transferase inhibitory activity of compounds of the present invention.

| Example Number | FTase, IC$_{50}$, μM |
|---|---|
| 1 | 2.0 |
| 2 | 8.4 |
| 3 | 2.4 (n = 1) |
| 4 | 0.078 |
| 5 | 1.37 (n = 1) |
| 6 | 1.26 |
| 7 | 1.7 (n = 1) |
| 8 | 11.9 (n = 1) |

-continued

| Example Number | FTase, IC$_{50}$, μM |
|---|---|
| 9 | 0.24 |
| 10 | 0.37 |
| 11 | 0.12 (n = 4) |
| 12 | 0.60 |
| 13 | 0.29 |
| 14 | 0.089 |
| 15 | 1.3 |
| 16 | 0.11 |
| 17 | 0.1 |
| 18 | 0.32 |
| 19 | 0.70 |
| 20 | 3.1 |
| 21 | 2.8 |
| 22 | 0.37 |
| 23 | 1.6 |
| 24 | 0.88 |
| 25 | 2.5 |
| 27 | 1.79 (n = 3) |
| 28 | 0.17 |
| 29 | 0.088 |
| 30 | 0.89 (n = 1) |
| 31 | 0.59 |
| 32 | 9.1 |
| 33 | 7.3 (n = 1) |
| 34 | 12.2 |
| 35 | 2.0 |
| 36 | 3.5 |
| 37 | 0.49 |
| 38 | 4.3 |
| 39 | 3.1 |
| 40 | 4.7 |
| 41 | 0.19 |
| 42 | 5.9 |
| 43 | 4.4 |
| 44 | 3.6 |
| 45 | 5.8 |
| 46 | 15.4 |
| 47 | 1.3 |
| 48 | 0.4 |
| 50 | 2.6 |
| 51 | 4.4 |
| 52 | 0.22 |
| 53 | 3.0 |
| 54 | 0.34 |
| 55 | 0.60 |
| 56 | 0.36 |
| 57 | 0.42 |
| 58 | 0.17 |
| 59 | 0.21 |
| 60 | 0.18 |
| 61 | 0.57 |
| 62 | 0.54 |
| 63 | 0.89 |
| 64 | 0.57 |
| 65 | 0.63 |
| 66 | 1.84 |
| 67 | 0.71 |
| 68 | 0.59 |
| 69 | 1.30 |
| 70 | 0.32 |
| 71 | 0.11 |
| 72 | 1.20 |
| 73 | 1.14 |
| 74 | 1.89 |
| 76 | 0.12 |
| 77 | 9.3 |
| 78 | 2.6 |
| 79 | 0.23 |
| 80 | 0.073 |
| 81 | 0.037 |
| 82 | 0.42 |
| 83 | 0.90 |

In general, the IC$_{50}$ represents the average of two tests. If otherwise, the number of tests is given in parentheses after the IC$_{50}$ value. For example, n=4, means the average IC$_{50}$ value for four tests. The activities listed for Examples 56–74, which were prepared by a parallel synthesis array, are the result of a single test. The values from this array have also been adjusted to account for the purity of the sample.

What is claimed is:

1. A compound having the Formula I wherein Q is O, —NOR, —N—NRR, —NOCH$_2$CO2R$^a$, —NOCH$_2$C(O)NH(CR$^a$R$^b$)$_{\overline{\alpha}}$—phenyl, —NOCH$_2$C(O)NH(CR$^a$R$^b$)$_\alpha$-substituted phenyl, or —NOCH$_2$C(O)NR$^a$R$^b$;

L is hydrogen, or   ;

each R$^a$ or R$^b$ is independently hydrogen, C$_1$–C$_6$ alkyl, C$_2$–C$_6$ alkenyl, phenyl, or substituted phenyl, or R$^a$ and R$^b$ along with the carbon atom to which they are bonded form a C$_3$–C$_6$ cycloalkyl ring;

each R is independently hydrogen, C$_1$–C$_6$ alkyl, C$_3$–C$_6$ cycloalkyl, benzyl, C$_2$–C$_6$ alkenyl, phenyl, or substituted phenyl;

Each - - - is a bond or absent;

—CR, —C—(CH$_2$)$_{\overline{n}}$—C(O)—NH(CR$^a$R$^b$)$_{\overline{n}}$—phenyl, —C—E', —C—(CH$_2$)$_n$C(O)NH(CR$^a$R$^b$)$_{\overline{n}}$—substituted phenyl, or —C—NHC(O)CH$_2$—pyridyl;

X is CH$_2$O, CH$_2$S, CH$_2$SO, CH$_2$SO$_2$, or CH$_2$NR;

Z is hydrogen when L is

, and

Z is —NRR, —R, —OR, —SR, (CH$_2$)$_n$E, —O(CH$_2$)$_n$E, —NR(CH$_2$)$_n$E, —S(CH$_2$)$_n$E, —N$^1$-piperidinyl, —N$^1$-piperazinyl[N$^4$—R], —N-pyrrolidinyl, —N-morpholino, —N-thiomorpholino, —N-hexahydroazepine, or an amino acid having the structure or  ;

when L is where A is a side chain of the amino acid glycine, alanine, valine, leucine, isoleucine, phenylalanine, proline, serine, threonine, tyrosine, asparagine, glutamine, lysine, arginine, tryptophan, histidine, cysteine, methionine, aspartic acid, or glutamic acid;

E is hydrogen, halogen, —CO$_2$R, —CONRR, —CN, —NO$_2$, C$_1$–C$_6$ perfluoroalkyl, C$_1$–C$_6$ perfluoroalkoxy, acetyl, —OR, —SR, —NRR, —N$^1$-piperidinyl, —N$^1$-piperazinyl[N$^4$—R], —N-pyrrolidinyl, —N-morpholino, —N-thiomorpholino, —N-hexahydroazepine, aryl, heteroaryl, substituted aryl, or substituted heteroaryl;

each E' is independently hydrogen, halogen, —NO$_2$, —NRR, —R, —OR,

—S(CH$_2$)$_n$E, —(CH$_2$)$_n$E, —NHC(O)CH$_2$—pyridyl,

—(CH$_2$)$_n$C(O)NH(CR$^a$R$^b$)$_n$-substituted phenyl, —O—(CH$_2$)$_n$E,

—NR(CH$_2$)$_n$E, —CO$_2$R, —CONRR, —NHCR, —CN,

—(CH$_2$)$_n$C(O)NH(CR$^a$R$^b$)$_{\overline{n}}$—phenyl, C$_1$—C$_6$ perfluoroalkyl, —CR, C$_1$—C$_6$ alkyl, C$_2$—C$_6$ alkenyl, benzyl, substituted benzyl, phenyl, or substituted phenyl;

each n is independently 0 to 5 inclusive;

each α is independently 0, 1, or 2;

each m is independently 0, 2, 3, 4, or 5;

Y is CH$_2$, NR, O, SO, SO$_2$, or S;

A' is aryl, heteroaryl, substituted aryl, substituted heteroaryl, C$_1$–C$_6$ alkyl, C$_1$–C$_6$ substituted alkyl,

,

C$_3$–C$_6$ cycloalkyl or C$_3$–C$_6$ substituted cycloalkyl, provided any substituents are not —NO$_2$;

B is pyrrolyl, substituted pyrrolyl, imidazolyl, substituted imidazolyl, oxazolyl, substituted oxazolyl, thiazolyl, substituted thiazolyl,

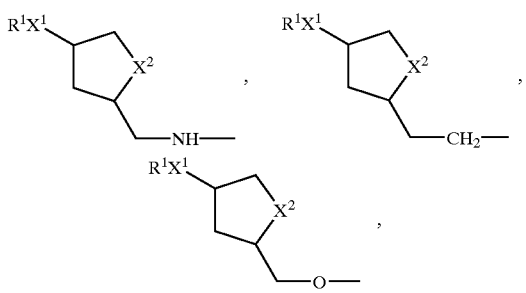

—NR$^1$—(CH$_2$)$_n$—(CHX$^3$)—(CH$_2$)$_n$—SR$^1$,
—S—(CH$_2$)$_n$—(CHX$^3$)—(CH$_2$)$_n$—SR$^1$, or
—(CH$_2$)$_n$—(CHX$^3$)—(CH$_2$)$_n$—SR$^1$;

X$^1$ is S or NR$^1$;

X$^2$ is NR$^1$ or CH$_2$;

R$^1$ is hydrogen or C$_1$–C$_6$ alkyl;

X$^3$ is hydrogen —NR$^1$R$^1$ or —C$_1$–C$_6$ alkyl, and the pharmaceutically acceptable salts, esters, amides, and prodrugs thereof, provided that the compound is not 5-(2-imidazole-1-yl-ethoxy)-indan-1-one.

2. A compound in accordance with claim 1 wherein Q is O.

3. A compound in accordance with claim 1 wherein E' is hydrogen.

4. A compound in accordance with claim 1 wherein P is CH.

5. A compound in accordance with claim 1 wherein Y is O.

6. A compound in accordance with claim 1 wherein L is hydrogen.

7. A compound in accordance with claim 1 wherein B is imidazolyl or substituted imidazolyl.

8. A compound in accordance with claim 1 wherein L is

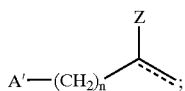

Z is hydrogen; and

A' is phenyl, substituted phenyl, pyridyl, substituted pyridyl, thienyl, substituted thienyl, furyl, substituted furyl, naphthyl, or substituted naphthyl.

9. The compounds:

7-[2-(1H-1-Imidazolyl)ethoxy]-3-[(E)-1-(2-thienyl)methylidene]-1,2,3,4-tetrahydro-4-quinolinone;

7-[2-(1H-1-Imidazolyl)ethoxy]-4H-4-chromenone;

7-[2-(1H-1-Imidazolyl)ethoxy]-4-chromanone; and

7-[2-(1H-1-Imidazolyl)ethoxy]-3-[(E)-1-(2-thienyl)methylidene]-4-chromanone.

10. The compounds:

7-[2-(1H-1-Imidazolyl)ethoxy]-2-phenyl-chromanone;

7-[2-(1H-1-Imidazolyl)ethoxy]-2-phenyl-4H-4-chromenone; and

7-[2-(1H-Imidazolyl)ethoxy]-2,2-dimethyl-4-chromanone.

11. A pharmaceutically acceptable composition that comprises a compound of claim 1.

12. A method of treating or preventing restenosis or atherosclerosis, the method comprising administering to a patient having restenosis or atherosclerosis or at risk of having restenosis or atherosclerosis a therapeutically effective amount of a compound of claim 1.

13. A method of treating cancer, the method comprising administering to a patient having cancer a therapeutically effective amount of a compound of claim 1.

14. A method of treating or preventing restenosis or atherosclerosis or treating cancer, the method of comprising administering to a patient having restenosis or atherosclerosis, or at risk of having restenosis or atherosclerosis, or having cancer a therapeutically effective amount of a compound of Formula I

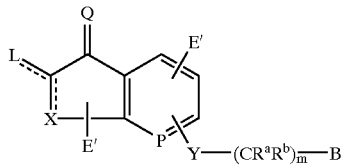

wherein Q is O, —NOR, —N—NRR, —NOCH$_2$CO$_2$R$^a$,

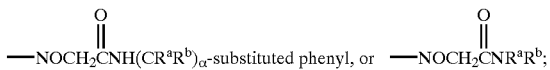

L is hydrogen,

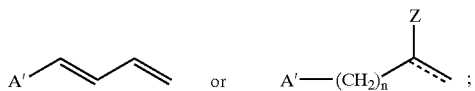

each R$^a$ or R$^b$ is independently hydrogen, C$_1$–C$_6$ alkyl, C$_2$–C$_6$ alkenyl, phenyl, or substituted phenyl, or R$^a$ and R$^b$ along with the carbon atom to which they are bonded form a C$_3$–C$_6$ cycloalkyl ring;

each R is independently hydrogen, C$_1$–C$_6$ alkyl, C$_3$–C$_6$ cycloalkyl, benzyl, C$_2$–C$_6$ alkenyl, phenyl, or substituted phenyl;

Each - - - is a bond or absent;

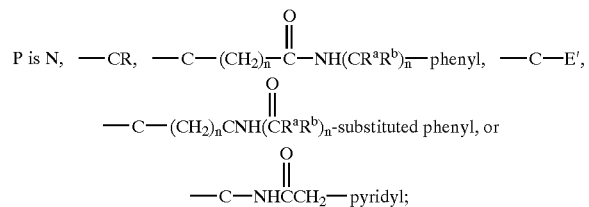

X is CH$_2$O, CH$_2$S, CH$_2$SO, CH$_2$SO$_2$, or CH$_2$NR;

Z is hydrogen when L is

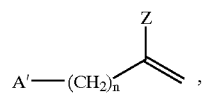

and

Z is —NRR, —R, —OR, —SR, —(CH$_2$)$_n$E, —O(CH$_2$)$_n$E, —NR(CH$_2$)$_n$E, —S(CH$_2$)$_n$E, —N$^1$-piperidinyl, —$N^1$-piperazinyl[$N^4$—R], —N-pyrrolidinyl, —N-morpholino, —N-thiomorpholino, —N-hexahydroazepine, or an amino acid having the structure

when L is

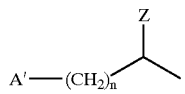

where A is a side chain of the amino acid glycine, alanine, valine, leucine, isoleucine, phenylalanine, proline, serine, threonine, tyrosine, asparagine, glutamine, lysine, arginine, tryptophan, histidine, cysteine, methionine, aspartic acid, or glutamic acid;

E is hydrogen, halogen, —$CO_2R$, —CONRR, —CN, —$NO_2$, $C_1$–$C_6$ perfluoroalkyl, $C_1$–$C_6$ perfluoroalkoxy, acetyl, —OR, —SR, —NRR, —$N^1$-piperidinyl, —$N^1$-piperazinyl[$N^4$—R], —N-pyrrolidinyl, —N-morpholino, —N-thiomorpholino, —N-hexahydroazepine, aryl, heteroaryl, substituted aryl, or substituted heteroaryl;

each E' is independently hydrogen, halogen, —$NO_2$, —NRR, —R, —OR,

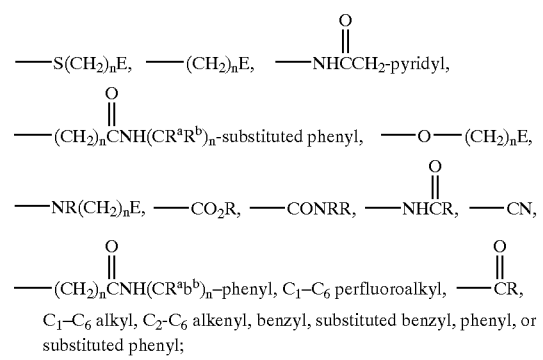

$C_1$–$C_6$ alkyl, $C_2$–$C_6$ alkenyl, benzyl, substituted benzyl, phenyl, or substituted phenyl;

each n is independently 0 to 5 inclusive;
each α is independently 0, 1, or 2;
each m is independently 0, 2, 3, 4, or 5;
Y is $CH_2$, NR, O, SO, $SO_2$, or S;
A' is aryl, heteroaryl, substituted aryl, substituted heteroaryl, $C_1$–$C_6$ alkyl, $C_1$–$C_6$ substituted alkyl,

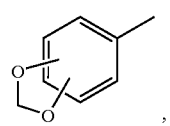

$C_3$–$C_6$ cycloalkyl or $C_3$–$C_6$ substituted cycloalkyl, provided any substituents are not —$NO_2$;

B is pyrrolyl, substituted pyrrolyl, imidazolyl, substituted imidazolyl, oxazolyl, substituted oxazolyl, thiazolyl, substituted thiazolyl,

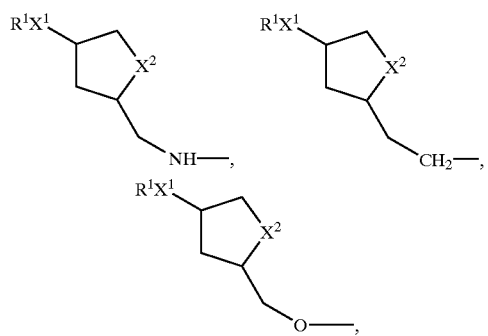

—$NR^1$—$(CH_2)_n$—$(CHX^3)$—$(CH_2)_n$—$SR^1$,
—S—$(CH_2)_n$—$(CHX^3)$—$(CH_2)_n$—$SR^1$, or
—$(CH_2)_n$—$(CHX^3)$—$(CH_2)_n$—$SR^1$;

$X^1$ is S or $NR^1$;
$X^2$ is $NR^1$ or $CH_2$;
$R^1$ is hydrogen or $C_1$–$C_6$ alkyl;
$X^3$ is hydrogen —$NR^1R^1$ or —$C_1$–$C_6$ alkyl, and the pharmaceutically acceptable salts, esters, amides, and prodrugs thereof.

15. A compound having the Formula IV

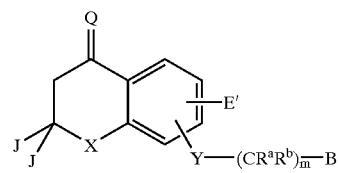

wherein each J is independently $C_1$–$C_6$ alkyl;
Y is $CH_2$, NR, O, SO, $SO_2$, or S;
each m is independently 0, 2, 3, 4, or 5;
each $R^a$ or $R^b$ is independently hydrogen, $C_1$–$C_6$ alkyl, $C_2$–$C_6$ alkenyl, phenyl, substituted phenyl, or $R^a$ and $R^b$ together with the carbon atom to which they are bonded form a $C_3$–$C_6$ cycloalkyl ring;

B is pyrrolyl, substituted pyrrolyl, imidazolyl, substituted imidazolyl, oxazolyl, substituted oxazolyl, thiazolyl, substituted thiazolyl,

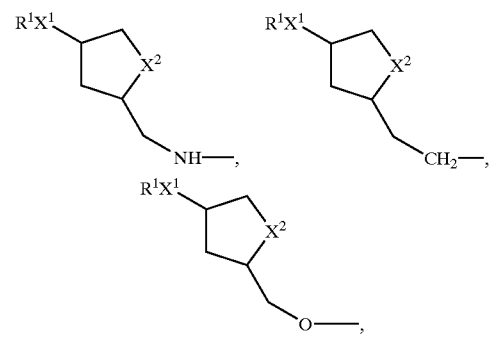

—$NR^1$—$(CH_2)_n$—$(CHX^3)$—$(CH_2)_n$—$SR^1$,
—S—$(CH_2)_n$—$(CHX_3)$—$(CH_2)_n$—$SR^1$, or
—$(CH_2)_n$—$(CHX^3)$—$(CH_2)_n$—$SR^1$;

$X^1$ is S or $NR^1$;

$X^2$ is $NR^1$ or $CH_2$;

$R^1$ is hydrogen or $C_1$–$C_6$ alkyl;

$X^3$ is hydrogen —$NR^1R^1$ or —$C_1$–$C_6$ alkyl;

X is —O—;

Q is O, —NOR, —N—NRR, —NOCH$_2$CO$_2$R$^a$,

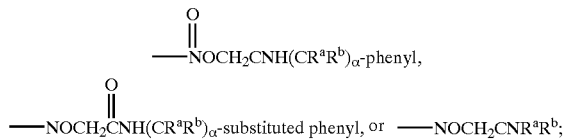

each R is independently hydrogen, $C_1$–$C_6$ alkyl, $C_3$–$C_6$ cycloalkyl, benzyl, $C_2$–$C_6$ alkenyl, phenyl, or substituted phenyl;

each E' is independently hydrogen, halogen, —NO$_2$, —NRR, —R, —OR,

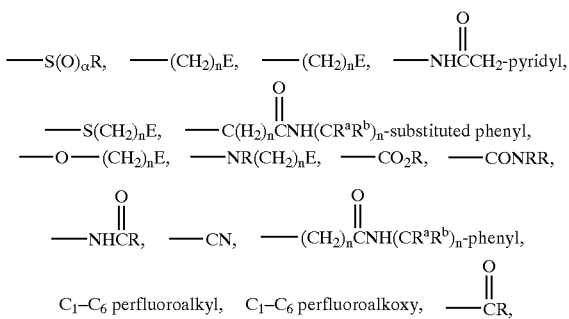

$C_1$–$C_6$ perfluoroalkyl, $C_1$–$C_6$ perfluoroalkoxy, —CR,

-continued $C_2$–$C_6$ alkenyl, benzyl, substituted benzyl, $C_1$–$C_6$ alkyl, phenyl, or substituted phenyl;

each α is independently 0, 1, or 2;

each n is independently 0 to 5;

E is hydrogen, halogen, —CO$_2$R, —CONRR, —CN, —NO$_2$, $C_1$–$C_6$ perfluoroalkyl, $C_1$–$C_6$ perfluoroalkoxy, acetyl, —OR, —SR, —NRR, —N$^1$-piperidinyl, —N$^1$-piperazinyl[N$^4$—R], —N-pyrrolidinyl, —N-morpholino, —N-thiomorpholino, —N-hexahydroazepine, aryl, heteroaryl, substituted aryl, or substituted heteroaryl;

and the pharmaceutically acceptable salts, esters, amides, and prodrugs thereof.

16. A pharmaceutically acceptable composition that comprises a compound of claim 15.

17. A method of treating or preventing restenosis or atherosclerosis, the method comprising administering to a patient having restenosis or atherosclerosis or at risk of having restenosis or atherosclerosis a therapeutically effective amount of a compound of claim 15.

18. A method of treating cancer, the method comprising administering to a patient having cancer a therapeutically effective amount of a compound of claim 15.

* * * * *